US011932906B2

(12) United States Patent
Chen et al.

(10) Patent No.: US 11,932,906 B2
(45) Date of Patent: Mar. 19, 2024

(54) SYSTEM AND METHODS FOR ELECTROKINETIC LOADING OF SUB-MICRON-SCALE REACTION CHAMBERS

(71) Applicant: Quantum-Si Incorporated, Guilford, CT (US)

(72) Inventors: Guojun Chen, Sherborn, MA (US); Jeremy Lackey, Foster City, CA (US); Alexander Goryaynov, New Haven, CT (US); Gerard Schmid, Guilford, CT (US); Ali Kabiri, Guilford, CT (US); Jonathan M. Rothberg, Guilford, CT (US); Todd Rearick, Cheshire, CT (US); Jonathan C. Schultz, Guilford, CT (US); Farshid Ghasemi, Guilford, CT (US); Keith G. Fife, Palo Alto, CA (US)

(73) Assignee: Quantum-Si Incorporated, Branford, CT (US)

( * ) Notice: Subject to any disclaimer, the term of this patent is extended or adjusted under 35 U.S.C. 154(b) by 441 days.

(21) Appl. No.: 17/350,509

(22) Filed: Jun. 17, 2021

(65) Prior Publication Data
US 2021/0310066 A1 Oct. 7, 2021

Related U.S. Application Data

(62) Division of application No. 16/239,789, filed on Jan. 4, 2019, now Pat. No. 11,072,827.

(60) Provisional application No. 62/614,912, filed on Jan. 8, 2018.

(51) Int. Cl.
C12Q 1/6869 (2018.01)
B01L 3/00 (2006.01)
C08L 1/02 (2006.01)
C12Q 1/6806 (2018.01)
G01N 21/64 (2006.01)
G01N 27/447 (2006.01)
G01N 30/86 (2006.01)
G01N 30/88 (2006.01)

(52) U.S. Cl.
CPC ...... *C12Q 1/6869* (2013.01); *B01L 3/502761* (2013.01); *B01L 3/50857* (2013.01); *C08L 1/02* (2013.01); *C12Q 1/6806* (2013.01); *G01N 21/6428* (2013.01); *G01N 21/6454* (2013.01); *G01N 27/44743* (2013.01); *G01N 27/44782* (2013.01); *G01N 30/86* (2013.01); *B01L 2200/0647* (2013.01); *B01L 2300/0645* (2013.01); *B01L 2300/0829* (2013.01); *B01L 2300/0864* (2013.01); *B01L 2400/0415* (2013.01); *B01L 2400/0421* (2013.01); *G01N 27/447* (2013.01); *G01N 30/88* (2013.01)

(58) Field of Classification Search
CPC ............... C12Q 1/6869; C12Q 1/6806; B01L 3/502761; B01L 3/50857; B01L 2200/0647; B01L 2300/0645; B01L 2300/0829; B01L 2300/0864; B01L 2400/0415; B01L 2400/0421; B01L 3/50; B01L 3/5027; B01L 3/508; C08L 1/02; G01N 21/6428; G01N 21/6454; G01N 27/44743; G01N 27/44782; G01N 30/86; G01N 27/447; G01N 30/88; B01J 19/0093
See application file for complete search history.

(56) References Cited

U.S. PATENT DOCUMENTS

| 5,961,924 | A | 10/1999 | Reichert et al. |
| 6,787,308 | B2 | 9/2004 | Balasubramanian et al. |
| 6,917,726 | B2 | 7/2005 | Levene et al. |
| 7,005,050 | B2 * | 2/2006 | Burns ............... G01N 27/44791 204/251 |
| 7,175,811 | B2 | 2/2007 | Bach et al. |
| 7,426,322 | B2 | 9/2008 | Hyde |
| 7,738,086 | B2 | 6/2010 | Shepard et al. |
| 7,746,451 | B1 | 6/2010 | Wilson et al. |
| 7,774,451 | B1 | 6/2010 | Wilson et al. |

(Continued)

FOREIGN PATENT DOCUMENTS

| CN | 101848757 A | 9/2010 |
| CN | 102395424 A | 3/2012 |

(Continued)

OTHER PUBLICATIONS

Invitation to Pay Additional Fees for International Application No. PCT/US2019/012271 dated Jul. 9, 2019.
International Search Report and Written Opinion for International Application No. PCT/US2019/012271 dated Oct. 8, 2019.
Hale, Fibre Optic Sensors using Adiabatically Tapered Single Mode Fibres. Dissertation submitted to the University of Cambridge. Feb. 1994. 209 pages.

(Continued)

*Primary Examiner* — Narayan K Bhat
(74) *Attorney, Agent, or Firm* — Wolf, Greenfield & Sacks, P.C.

(57) ABSTRACT

Apparatus and techniques for electrokinetic loading of samples of interest into sub-micron-scale reaction chambers are described. Embodiments include an integrated device and related apparatus for analyzing samples in parallel. The integrated device may include at least one reaction chamber formed through a surface of the integrated device and configured to receive a sample of interest, such as a molecule of nucleic acid. The integrated device may further include electrodes patterned adjacent to the reaction chamber that produce one or more electric fields that assist loading the sample into the reaction chamber. The apparatus may further include a sample reservoir having a fluid seal with the surface of the integrated device and configured to hold a suspension containing the samples.

17 Claims, 22 Drawing Sheets

(56) References Cited

U.S. PATENT DOCUMENTS

| | | |
|---|---|---|
| 7,820,983 B2 | 10/2010 | Lundquist et al. |
| 7,834,329 B2 | 11/2010 | Lundquist et al. |
| 7,838,847 B2 | 11/2010 | Lundquist et al. |
| 8,053,742 B2 | 11/2011 | Lundquist et al. |
| 8,207,509 B2 | 6/2012 | Lundquist et al. |
| 8,274,040 B2 | 9/2012 | Zhong et al. |
| 8,278,728 B2 | 10/2012 | Murshid |
| 8,465,699 B2 | 6/2013 | Fehr et al. |
| 8,471,219 B2 | 6/2013 | Lundquist et al. |
| 8,471,230 B2 | 6/2013 | Zhong et al. |
| 8,502,169 B2 | 8/2013 | Rigneault et al. |
| 8,618,507 B1 | 12/2013 | Lundquist et al. |
| 9,029,802 B2 | 5/2015 | Lundquist et al. |
| 9,157,864 B2 | 10/2015 | Fehr et al. |
| 9,222,123 B2 | 12/2015 | Zhong et al. |
| 9,222,133 B2 | 12/2015 | Lundquist et al. |
| 9,223,084 B2 | 12/2015 | Grot et al. |
| 9,372,308 B1 | 6/2016 | Saxena et al. |
| 9,587,276 B2 | 3/2017 | Lundquist et al. |
| 9,606,060 B2 | 3/2017 | Chen et al. |
| 9,658,161 B2 | 5/2017 | Saxena et al. |
| 9,666,748 B2 | 5/2017 | Leobandung |
| 9,719,138 B2 | 8/2017 | Zhong et al. |
| 9,765,395 B2 | 9/2017 | Goldsmith |
| 9,885,657 B2 | 2/2018 | Rothberg et al. |
| 9,946,017 B2 | 4/2018 | Saxena et al. |
| 10,018,764 B2 | 7/2018 | Grot et al. |
| 10,090,429 B2 | 10/2018 | Leobandung |
| 10,138,515 B2 | 11/2018 | Fehr et al. |
| 10,280,457 B2 | 5/2019 | Zhong et al. |
| 10,310,178 B2 | 6/2019 | Saxena et al. |
| 10,487,356 B2 | 11/2019 | Lundquist et al. |
| 10,578,788 B2 | 3/2020 | Grot et al. |
| 10,655,172 B2 | 5/2020 | Rank et al. |
| 10,724,090 B2 | 7/2020 | McCaffrey et al. |
| 11,072,827 B2 | 7/2021 | Chen et al. |
| 2002/0182716 A1 | 12/2002 | Weisbuch et al. |
| 2003/0174992 A1 | 9/2003 | Levene et al. |
| 2009/0202985 A1 | 8/2009 | Gulak et al. |
| 2010/0065726 A1 | 3/2010 | Zhong et al. |
| 2011/0223590 A1 | 9/2011 | Chiou et al. |
| 2013/0116153 A1 | 5/2013 | Bowen et al. |
| 2015/0072868 A1 | 3/2015 | Ohlsson et al. |
| 2016/0084761 A1 | 3/2016 | Rothberg et al. |
| 2016/0178570 A1 | 6/2016 | Fife |
| 2017/0146479 A1 | 5/2017 | Levine et al. |
| 2017/0350818 A1 | 12/2017 | Rothberg et al. |
| 2018/0172906 A1 | 6/2018 | Rothberg et al. |
| 2019/0025511 A1 | 1/2019 | Rothberg et al. |
| 2019/0211389 A1 | 7/2019 | Chen et al. |
| 2019/0292590 A1 | 9/2019 | Zhong et al. |

FOREIGN PATENT DOCUMENTS

| | | |
|---|---|---|
| CN | 102686997 A | 9/2012 |
| CN | 104379261 A | 2/2015 |
| CN | 107430016 A | 12/2017 |
| JP | 2013/522605 A | 6/2013 |
| JP | 2016/537999 A | 12/2016 |
| KR | 10-2001-0041147 A | 5/2001 |
| KR | 10/1352144 B1 | 1/2014 |
| KR | 10-2017-0041848 A | 4/2017 |
| KR | 10-2017-0104937 A | 9/2017 |
| TW | 201632261 A | 9/2016 |
| WO | WO 2011/153962 A1 | 12/2011 |
| WO | WO 2016/161400 A1 | 10/2016 |
| WO | WO 2018/099088 A1 | 6/2018 |

OTHER PUBLICATIONS

Mogensen et al., A Microfluidic Device with an Integrated Waveguide Beam Splitter for Velocity Measurements of Flowing Particles by Fourier Transformation. Analytical Chemistry. Sep. 15, 2003;75(18):4931-4936.

Taitt et al., Evanescent wave fluorescence biosensors. Biosens Bioelectron. Jun. 2005;20(12):2470-87. Epub Dec. 8, 2004.

U.S. Appl. No. 16/239,789, filed Jan. 4, 2019, Chen et al.

PCT/US2019/012271, Jul. 9, 2019, Invitation to Pay Additional Fees.

PCT/US2019/012271, Oct. 8, 2019, International Search Report and Written Opinion.

* cited by examiner

SYSTEM AND METHODS FOR ELECTROKINETIC LOADING OF SUB-MICRON-SCALE REACTION CHAMBERS

RELATED APPLICATION DATA

This application claims priority under 35 U.S.C. § 120 and is a divisional of U.S. application Ser. No. 16/239,789, filed Jan. 4, 2019, titled "System and Methods for Electrokinetic Sample Loading," which is incorporated herein by reference in its entirety. U.S. application Ser. No. 16/239,789 claims priority to U.S. provisional application No. 62/614,912 filed Jan. 8, 2018 and titled, "System and Methods for Electrokinetic Sample Loading," which is incorporated by reference herein in its entirety.

FIELD OF THE APPLICATION

The present application relates to integrated devices and related instruments that can perform massively-parallel analyses of samples by providing short optical pulses to tens of thousands of reaction chambers or more simultaneously and receiving fluorescent signals from the reaction chambers for sample analyses. The instruments may be useful for point-of-care genetic sequencing and for personalized medicine.

BACKGROUND

Instruments that are capable of massively-parallel analyses of biological or chemical samples are typically limited to laboratory settings because of several factors that can include their large size, lack of portability, requirement of a skilled technician to operate the instrument, power need, need for a controlled operating environment, and cost. When a sample (e.g., DNA) is to be analyzed using such equipment, a common paradigm is to extract a specimen at a point of care or in the field, send the specimen to the lab and wait for results of the analysis. The wait time for results can range from hours to days.

BRIEF DESCRIPTION OF THE DRAWINGS

Various aspects and embodiments of the application will be described with reference to the following figures. It should be appreciated that the figures are not necessarily drawn to scale. Items appearing in multiple figures are indicated by the same reference number in all the figures in which they appear.

FIG. 2-1 is a schematic of a cross-section view of an integrated device having an electrode configuration for electrokinetic sample loading, according to some embodiments.

FIG. 2-2 is a schematic of a cross-section view of an integrated device having an electrode configuration for electrokinetic sample loading, according to some embodiments.

FIG. 2-3 is a schematic of a cross-section view of an integrated device having an electrode configuration for electrokinetic sample loading, according to some embodiments.

FIG. 2-4 is a schematic of a cross-section view of an integrated device having an electrode configuration for electrokinetic sample loading, according to some embodiments.

FIG. 2-5 is a schematic of a cross-section view of an integrated device having an electrode configuration for electrokinetic sample loading, according to some embodiments.

FIG. 2-6 is a schematic of a cross-section view of an integrated device having an electrode configuration for electrokinetic sample loading with contacts to electrodes formed as part of the integrated device, according to some embodiments.

FIG. 2-7 is a schematic of a cross-section view of an integrated device having an electrode configuration for electrokinetic sample loading with contacts to electrodes formed as part of the integrated device, according to some embodiments.

FIG. 2-8 is a schematic of a cross-section view of an integrated device having an electrode configuration for electrokinetic sample loading with contacts to electrodes formed as part of the integrated device, according to some embodiments.

FIG. 2-9 is a schematic of a cross-section view of an integrated device having an electrode configuration for electrokinetic sample loading with vias to electrodes formed as part of the integrated device, according to some embodiments.

FIG. 3-1A is a schematic of a voltage signal applied to electrodes for electrokinetic sample loading, according to some embodiments.

FIG. 3-1B is a schematic of a current waveform provided to electrodes for electrokinetic sample loading, according to some embodiments.

FIG. 3-2 is a schematic of a voltage signal applied to electrodes for electrokinetic sample loading, according to some embodiments.

FIG. 4-1A, FIG. 4-1B, FIG. 4-1C, and FIG. 4-1D depict structures associated with a method of forming contacts to an electrically conductive layer(s) of an integrated device, according to some embodiments.

FIG. 4-2A, FIG. 4-2B, and FIG. 4-2C depict structures associated with a method of forming contact to electrically conductive layer(s) of an integrated device, according to some embodiments.

FIG. 4-3 depicts steps associated with a method of forming vias to an electrically conductive layer(s) of an integrated device, according to some embodiments.

FIG. 4-4A, FIG. 4-4B, and FIG. 4-4C depict structures associated with a method of forming a perforated dielectric layer, according to some embodiments.

FIG. 5-1A is a block diagram of an integrated device and an instrument, according to some embodiments.

FIG. 5-1B is a schematic of an apparatus including an integrated device, according to some embodiments.

FIG. 5-2 is a schematic of a pixel having a reaction chamber, optical waveguide, and time-binning photodetector, according to some embodiments.

FIG. 5-3 is a schematic of an exemplary biological reaction that may occur within a reaction chamber, according to some embodiments.

FIG. 5-4 is a plot of emission probability curves for two different fluorophores having different decay characteristics.

FIG. 5-5 is a plot of time-binning detection of fluorescent emission, according to some embodiments.

FIG. 5-6A is an exemplary time-binning photodetector, according to some embodiments.

FIG. 5-6B is an exemplary time-binning photodetector, according to some embodiments.

FIG. 5-7A is a schematic illustrating pulsed excitation and time-binned detection of fluorescent emission from a reaction chamber, according to some embodiments.

FIG. 5-7B is a histogram of accumulated fluorescent photon counts in various time bins after repeated pulsed excitation of a sample, according to some embodiments.

FIG. 5-8A, FIG. 5-8B, FIGS. 5-8C, and 5-8D are different histograms that may correspond to the four nucleotides (T, A, C, G) or nucleotide analogs, according to some embodiments.

DETAILED DESCRIPTION

I. Introduction

Figure 1:
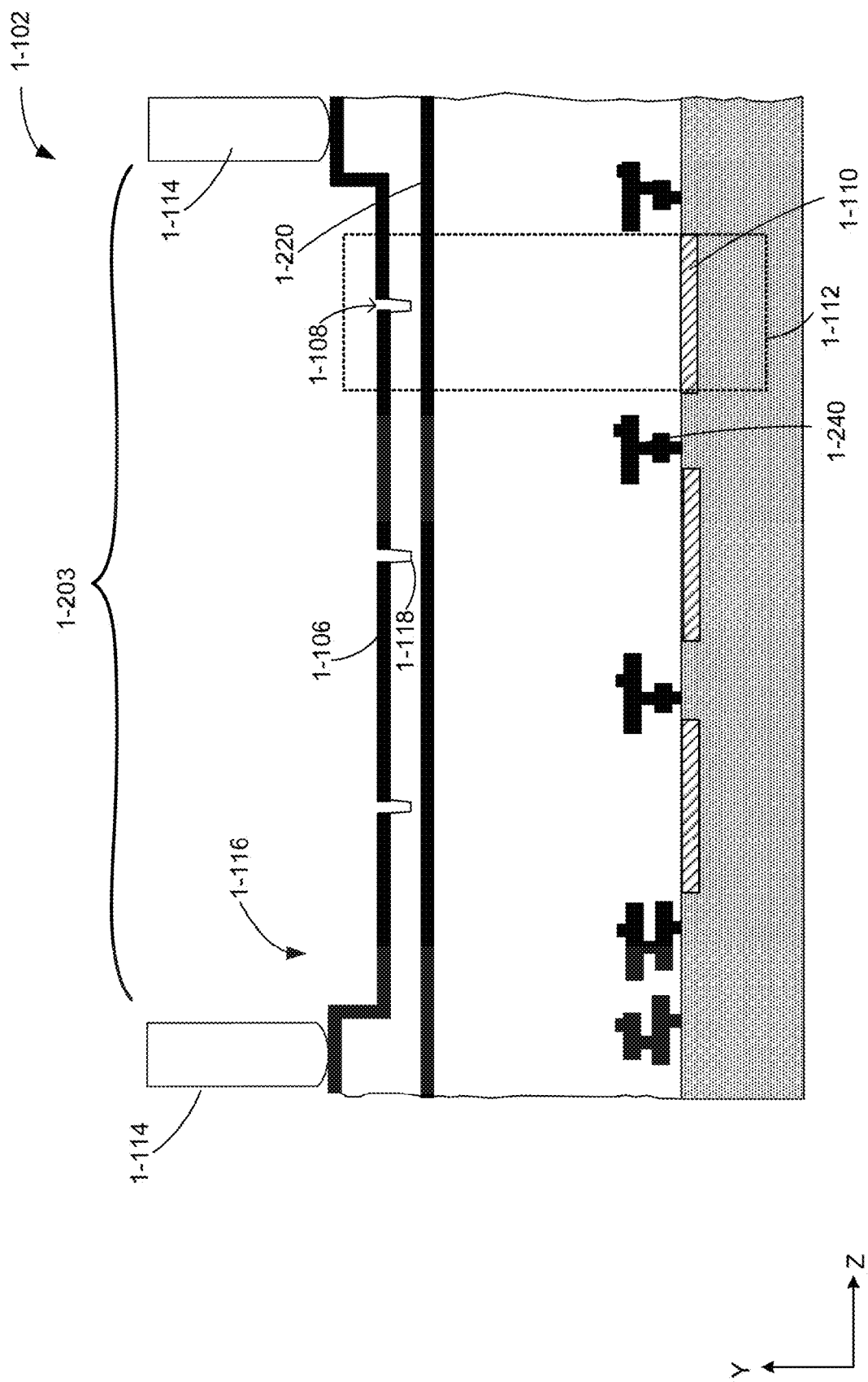
FIG. 1-1 is a schematic of a cross-sectional view of an integrated device, according to some embodiments.

Aspects of the present application relate to integrated devices, instruments and related systems capable of analyzing samples in parallel, including identification of single molecules and nucleic acid sequencing. Such systems may be compact, easy to carry, and easy to operate, allowing a physician or other provider to readily use the system and transport the system to a desired location where care may be needed. Analysis of a sample may include labeling the sample or associated components (e.g., reaction components) with one or more fluorescent markers, which may be used to detect the sample and/or identify single molecules of the sample (e.g., individual nucleotide identification as part of nucleic acid sequencing). A fluorescent marker may become excited in response to illuminating the fluorescent marker with excitation light (e.g., light having a characteristic wavelength that may excite the fluorescent marker to an excited state) and, if the fluorescent marker becomes excited, emit emission light (e.g., light having a characteristic wavelength emitted by the fluorescent marker by returning to a ground state from an excited state). Detection of the emission light may allow for identification of the fluorescent marker, and thus, the sample or a molecule associated with the sample labeled by the fluorescent marker. According to some embodiments, the instrument may be capable of massively-parallel sample analyses and may be configured to handle tens of thousands of samples or more simultaneously.

The inventors have recognized and appreciated that an integrated device, having reaction chambers configured to receive the sample and integrated optics formed on the integrated device, and an instrument configured to interface with the integrated device may be used to achieve analysis of this number of samples. The instrument may include one or more excitation light sources, and the integrated device may interface with the instrument such that the excitation light is delivered to the reaction chambers using integrated optical components (e.g., waveguides, optical couplers, optical splitters) formed on the integrated device. The optical components may improve the uniformity of illumination across the reaction chambers of the integrated device and may reduce a large number of external optical components that might otherwise be needed. Furthermore, the inventors have recognized and appreciated that integrating photodetectors on the integrated device may improve detection efficiency of fluorescent emissions from the reaction chambers and reduce the number of light-collection components that might otherwise be needed.

In the context of single molecule analysis, challenges may arise in separating a sample of interest or molecule of interest (e.g., template nucleic acid) from among other molecules in a suspension for loading in individual reaction chambers. The inventors have recognized and appreciated that isolating a molecule of interest from among other molecules in a suspension may be achieved by forming the reaction chambers of the integrated device to be suitably sized and shaped to allow for isolation of an individual molecule. In this manner, a user may deposit a suspension for analysis on a surface of the integrated device having an array of the reaction chambers such that individual reaction chambers may have a high probability of receiving a single molecule of the suspension through diffusion. In some implementations, the reaction chambers may be suitably sized and shaped such that the distribution of the number of molecules that individual reaction chambers receive may allow a reaction chamber to receive 0, 1, 2, or more molecules. As an example, the distribution of molecules of interest may approximate a Poisson distribution where a fraction (e.g., approximately 35%) of the reaction chambers receive single molecules.

In some implementations of the integrated device, a reaction chamber is positioned relative to a waveguide such that excitation light propagating through the waveguide is coupled to the reaction chamber and illuminates a fluorescent marker used to label the molecule. In addition, the reaction chamber is positioned relative to one or more photodetectors such that light emitted by the fluorescent molecule is detected by the photodetector(s). Challenges may arise in loading molecules into individual reaction chambers such that a molecule is positioned within a reaction chamber to allow for sufficient excitation of a fluorescent marker and/or sufficient optical detection of light emitted from a fluorescent marker. For example, some embodiments of the integrated device include reaction chambers that have a bottom surface recessed from a surface of the integrated device such that individual reaction chambers have a depth on the order of a hundred to several hundred nanometers (e.g., in the range of approximately 100 nm to approximately 500 nm). In such embodiments, a molecule and/or a fluorescent marker used to label a molecule may need to be positioned proximate to the bottom surface to receive excitation light and/or for a photodetector associated with the reaction chamber to receive emission light.

When using such devices for single molecule analysis, one challenge that may arise includes positioning a molecule of interest proximate to the bottom surface of a reaction chamber because separating a molecule of interest from a suspension provided on the surface of the integrated device may involve moving the molecule of interest from within the bulk of the suspension and through the depth of the reaction chamber. The efficiency of loading molecules into reaction chambers may become diffusion limited due to the distances that a molecule may have to move from within the bulk of the suspension to the bottom surface of a reaction chamber. For example, the amount of time needed for loading a molecule into a reaction chamber increases with the distance of molecule needs to move such that loading efficiency may become limited for reaction chambers having large depths. The amount of time needed for loading may depend on the size of the molecule such that larger molecules may take more time than smaller molecules to move by diffusion from the bulk of the suspension to within the reaction chamber. In applications that involve suspensions having low molecule concentrations, the low concentration of a molecule of interest may further increase the amount of time needed to load the molecules than for suspensions with high molecule concentrations. Across an array of reaction chambers, these limitations that arise from relying primarily on diffusion for sample loading may impact the ability to load molecules within a desired number of reaction chambers in the array such that only a portion of the reaction chambers become loaded with a molecule for analysis. The sample loading techniques described herein may overcome these limitations by increasing loading efficiency, including reducing the time for loading a molecule into a reaction chamber, in comparison to relying on diffusion alone. These sample loading techniques may be particularly suited for applications that involve loading large molecules, such nucleic acid molecules, and/or handling suspensions with particularly low concentrations of molecules. In applications that involve nucleic acid molecules, electrokinetic loading may be particularly beneficial for molecules containing more than 10,000 bases, 20,000 bases, or 30,000 bases. Electrokinetic loading may be particularly beneficial when the concentration of nucleic acid in a suspension is less than 100 fM, less than 10 fM, less than 1 fM, or less than 100 pM.

In particular, the inventors have recognized and appreciated that applying an electric field configured to assist loading of a molecule of interest into a reaction chamber may improve sample loading efficiency. Such techniques may be considered as electrokinetic sample loading because the molecule moves in response to the influence of an electric field to a desired location. Using electrokinetic sample loading may involve applying an electrical signal to a set of electrodes such that the molecule of interest moves to a desired location. In applications where the molecule of interest is charged (e.g., has a net positive or negative charge), such techniques may be considered as electrophoretic sample loading because the movement of the molecules may depend both on the applied electric field and the charge of the molecule of interest. In such embodiments, these techniques may be particularly suited for transporting a molecule of interest to a desired location because the electric field may have a stronger influence on the molecule of interest than for uncharged molecules.

Implementing electrokinetic sample loading may involve suitable positioning of one or more electrodes configured to generate an electric field, such as in response to receiving an electrical signal from circuitry, in the vicinity of a reaction chamber such that a molecule of interest moves towards the reaction chamber and/or into the reaction chamber. The inventors have recognized and appreciated that the electric field may be generated using different arrangements of one or more electrodes. In particular, the inventors have further recognized and appreciated that forming an integrated device to include one or more electrically conductive layers configured to act as electrode(s) may provide benefits to improving sample loading across an array of reaction chambers than if only external electrodes were implemented. Incorporating an electrically conductive layer that acts as an electrode in an integrated device may allow for improved manipulation of an electric field (e.g., electric field strength, directionality) than by using external electrodes alone. In particular, such an implementation may allow for generation of an electric field that more specifically targets moving molecules from the bulk of a suspension towards and/or into individual reaction chambers than through utilization of external electrodes. As an example, the electrically conductive layer(s) of an integrated device may act to generate an electric field having a suitably high strength at or proximate to a surface of the integrated device and/or a bottom surface of a reaction chamber (e.g., a surface recessed from a surface of the integrated device), which may improve loading of a molecule. As another example, an integrated device may include electrically conductive layer(s) that act as electrode(s) for individual reaction chambers of the integrated device such that the electric field for different reaction chambers may be individually controlled. As yet another example, an integrated device may include electrically conductive layers where one set of layers are configured to move a molecule of interest from within the bulk of the suspension towards the reaction chambers and another set of layers are configured to move the molecule of interest into the reaction chamber. In some instances, the generated electric field may move the molecule of interest from within the bulk of a suspension (e.g., in a reservoir positioned over the integrated device) towards a reaction chamber.

In addition, incorporating electrically conductive layer(s) into an integrated device for the purpose of electrokinetic sample loading may provide the benefit of improving the feasibility of implementing an electrokinetic process as part of loading the sample during use because it reduces, and in some instances removes, the step of positioning an electrode external to the integrated device as part of loading a sample. Instead, a user may simply deposit a suspension on a surface of the integrated device and operate circuitry coupled to the electrically conductive layer(s) to control generation of an electric field. In some cases, operation of the circuitry may be automated (e.g., initiate automatically after loading a chip into an instrument and terminate automatically in response to feedback signals from the chip). Such a process may improve the amount of time associated with sample loading and performing analysis of a sample. In addition, such implementations may improve the user's overall experience with using the integrated device and associated instrument to conduct the analysis by simplifying the sample loading process.

According to the techniques described herein, different configurations of one or more electrically conductive layers of an integrated device may be used to provide one or more of these benefits. In some embodiments of the integrated device, electrically conductive layer(s) formed in an integrated device may be formed at or proximate to a surface of the integrated device. In some embodiments of the integrated device, some or all of the reaction chambers may be formed through the electrically conductive layer(s) of the integrated device such that individual reaction chambers form openings or discontinuities within the electrically conductive layer(s). In some embodiments, a reaction chamber of an integrated device may be separated from an electrically conductive layer of the integrated device by dielectric material. In some embodiments, an integrated device may include a circuit, such as a circuit coupled to and configured to control a photodetector, formed of the electrically conductive layer(s) that are also configured to generate an electric field to assist with electrokinetic sample loading, thereby serving a dual purpose for an integrated circuit or integrated device and for electrokinetic sample loading. In some configurations, an electric field that assists with sample loading may be generated by using the electrically conductive layer(s) in the integrated circuit or integrated device as one electrode and another electrode that is separate from the integrated device.

In some embodiments, electrically conductive layer(s) of an integrated device may be configured to form both a first electrode and a second electrode used to assist loading a molecule into one or more reaction chambers of the integrated device. Dielectric material may be formed in the integrated device to electrically isolate the first and second electrodes to generate an electric filed, but limit current flow, between the first and second electrodes. In some embodiments, the same set of electrically conductive layer(s) within the integrated device may be used to form both the first electrode and the second electrode. In such embodiments, the first electrode and the second electrode may be positioned relative to the reaction chamber to generate an electric field laterally over the reaction chamber. In some embodiments, a first electrically conductive layer may form a first electrode and a second electrically conductive layer may form a second electrode where the first and the second electrically conductive layers are separated by dielectric material. In some embodiments, one or more sidewalls of reaction chamber may be electrically conductive and electrically coupled to one or more electrically conductive layers of the integrated device. The electrically conductive sidewall(s) may allow for generation of an electric field within the reaction chamber that acts to assist a molecule to move within the reaction chamber, and in some instances towards a bottom surface of the reaction chamber.

To provide electrical signals to the electrically conductive layer(s) of an integrated device, an apparatus according to the techniques described herein may include circuitry configured to electrically couple to the electrically conductive layer(s) where the circuitry is configured to provide electrical signals to the electrically conductive layer(s) to generate an electric field. In some embodiments, some or all of the circuitry may be external to the integrated device. In some instances, the integrated device may be configured to interface with the circuitry such that the circuitry may be electrically coupled through one or more electrical connections to assist with sample loading and disconnected or disabled once a desired amount of sample loading is achieved. Some embodiments of the integrated device may include some or all of the circuitry, such as one or more integrated circuits formed in the integrated device and electrically coupled to the electrically conductive layer(s) of the device. In some instances, the circuitry may be located both on the integrated device and external to the integrated device. Regardless of the configuration of the circuitry, the circuitry may be configured to apply a suitable electrical signal to the electrically conductive layer(s) and/or external electrode. In some embodiments, the circuitry may be configured to generate a time-varying voltage signal and apply the time-varying voltage signal to the electrically conductive layer(s). Applying the time-varying voltage signal may generate an electric field that varies over time, which may assist with loading of a molecule. A molecule moving under the influence of an electric field may have reduced movement or become immobilized due to a volume that the molecule occupies in the suspension and how the volume constrains the ability of the molecule to move towards and/or into a reaction chambers. Applying a time-varying voltage may assist with reducing or preventing immobilization of the molecule by allowing the molecule to be under the influence of the different types of electric fields, which may allow the molecule to reposition or rearrange itself. For example, having time during a sample loading process where a molecule is not primarily under the influence of an electric field and diffusion dominates the molecule's movement may allow the molecule to reposition or rearrange itself, which may assist with loading the molecule into a reaction chamber when a subsequent electric field is generated. In some instances, the circuitry may be configured to generate a voltage signal having two or more periodic waves with different frequencies and apply the signal to the electrically conductive layer(s).

Other techniques to assist with sample loading may be used in combination with the electrokinetic sample loading techniques described herein. Some techniques may include introducing one or more agents to a suspension prior to or after depositing the suspension on a surface of an integrated device that act to assist with loading a sample of interest (e.g., a molecule of interest) into a reaction chamber of the integrated device. Such agent(s) may impact the arrangement of the molecule such that it may be more suitable for loading into a reaction chamber. One type of agent is a condensing agent configured to reduce the volume a molecule of interest occupies in a suspension, which may be considered the pervaded volume of the molecule. By introducing a condensing agent, the molecule may have a smaller pervaded volume than if the condensing agent was absent and the molecule may more readily load into a reaction chamber because of its smaller pervaded volume. Another type of agent is a crowding agent configured to reduce the volume accessible to a molecule in the suspension. In some embodiments, a crowding agent may increase the concentration of a molecule of interest proximate to a surface of the integrated device by excluding the molecule of interest from the bulk of the suspension. Examples of suitable condensing agents and crowding agents are described further herein and in U.S. patent application Ser. No. 15/847,001, filed Dec. 19, 2017, titled "LOADING MOLECULES INTO REACTION CHAMBERS FOR ANALYSIS," which is incorporated by reference in its entirety.

II. Electrokinetic Sample Loading

A cross-sectional schematic of integrated device 1-102 illustrating a row of pixels 1-112 is shown in FIG. 1-1. Pixels 1-112 are formed in pixel region 1-203 of integrated device 1-102, where individual pixels 1-112 include a reaction chamber 1-108 and photodetector region having one or more photodetectors 1-110. Reaction chambers 1-108 may be formed through surface 1-116 of integrated device 1-102, and in some embodiments through electrically conductive layer(s) 1-106. In some embodiments, electrically conductive layer(s) 1-106 may form surface 1-116 of integrated device 1-102. In some embodiments, surface 1-116 of integrated device 1-102 may include dielectric material. Although not shown in FIG. 1-1, layer(s) of dielectric material may be formed over electrically conductive layer(s) 1-106, forming some or all of surface 1-116. In some embodiments of the integrated device, openings within the layer(s) of dielectric material may expose a surface of electrically conductive layer(s) 1-106 and a reaction chamber may be formed through the exposed surface. The resulting configuration may allow for generation of an electric field having a desired electric field strength concentrated proximate to the reaction chamber.

As shown in FIG. 1-1, pixel region 1-203 may include a recessed region, which may be considered as a trench region. Some embodiments may include sample reservoir 1-114 positioned around some or all of pixel region 1-203, such as by being positioned around the trench region as shown in FIG. 1-1. Sample reservoir 1-114 may form a fluid seal with surface 1-116 of integrated device 1-102 such that a suspension containing at least one sample of interest and/or other components (e.g., crowding agents, condensing agents) may be retained within a region over pixel region 1-203. Although FIG. 1-1 only shows a cross-sectional view of sample reservoir 1-114, it should be appreciated that, in some embodiments, sample reservoir 1-114 may extend in the dimension perpendicular to the view shown in FIG. 1-1 so that sample reservoir 1-114 forms an enclosed region surrounding pixel region 1-203. In some embodiments, sample reservoir 1-114 may be formed on integrated device 1-102 as part of a packaging process of integrated device 1-102. In such embodiments, a user may simply deposit a suspension for analysis within sample reservoir 1-114 as it is already positioned to surround pixel region 1-203. In some embodiments, sample reservoir 1-114 may be detachably coupled to integrated device 1-102. In such embodiments, a user may position sample reservoir 1-114 on integrated device 1-102 and deposit a suspension containing at least one sample of interest for analysis within sample reservoir 1-114 prior to sample analysis. Although only three pixels 1-112 are shown in FIG. 1-1, it should be appreciated that any suitable number of pixels may be positioned within a row of pixels. In addition, integrated device 1-102 may have any suitable number of rows of pixels, forming a pixel array with an array of reaction chambers formed through surface 1-116 of integrated device 1-102. Sample reservoir 1-114 may be suitably sized and shaped to accommodate any suitable number of reaction chambers 1-108 formed as part of integrated device 1-102.

As part of loading the sample, molecules of interest may enter reaction chambers 1-108 and, in some embodiments, may move towards a bottom surface 1-118 positioned proximate to waveguide 1-220. In embodiments that include sample reservoir 1-114, loading a molecule of interest may include using techniques that move the molecule of interest from within the bulk of a suspension deposited within sample reservoir 1-114 towards surface 1-116 of integrated device 1-102. Excitation light propagating along waveguide 1-220, such as along the z-direction shown in FIG. 1-1, may illuminate a molecule of interest and/or a fluorescent marker labeling the molecule of interest positioned within reaction chamber 1-108 by coupling (e.g., evanescently coupling) a portion of the excitation light from waveguide 1-220 to reaction chamber 1-108. In some cases, a bottom of the reaction chamber is located within one micron of the waveguide 1-220. The molecule of interest and/or the fluorescent marker labeling the molecule of interest may emit emission light in response to receiving the excitation light, and photodetector(s) 1-110 in the same pixel as the reaction chamber 1-108 may receive the emission light. In some cases, metal layers 1-240 may comprise circuitry for an integrated device 1-102, for example as control circuitry for photodetector(s) 1-110.

Figures 1, 2:
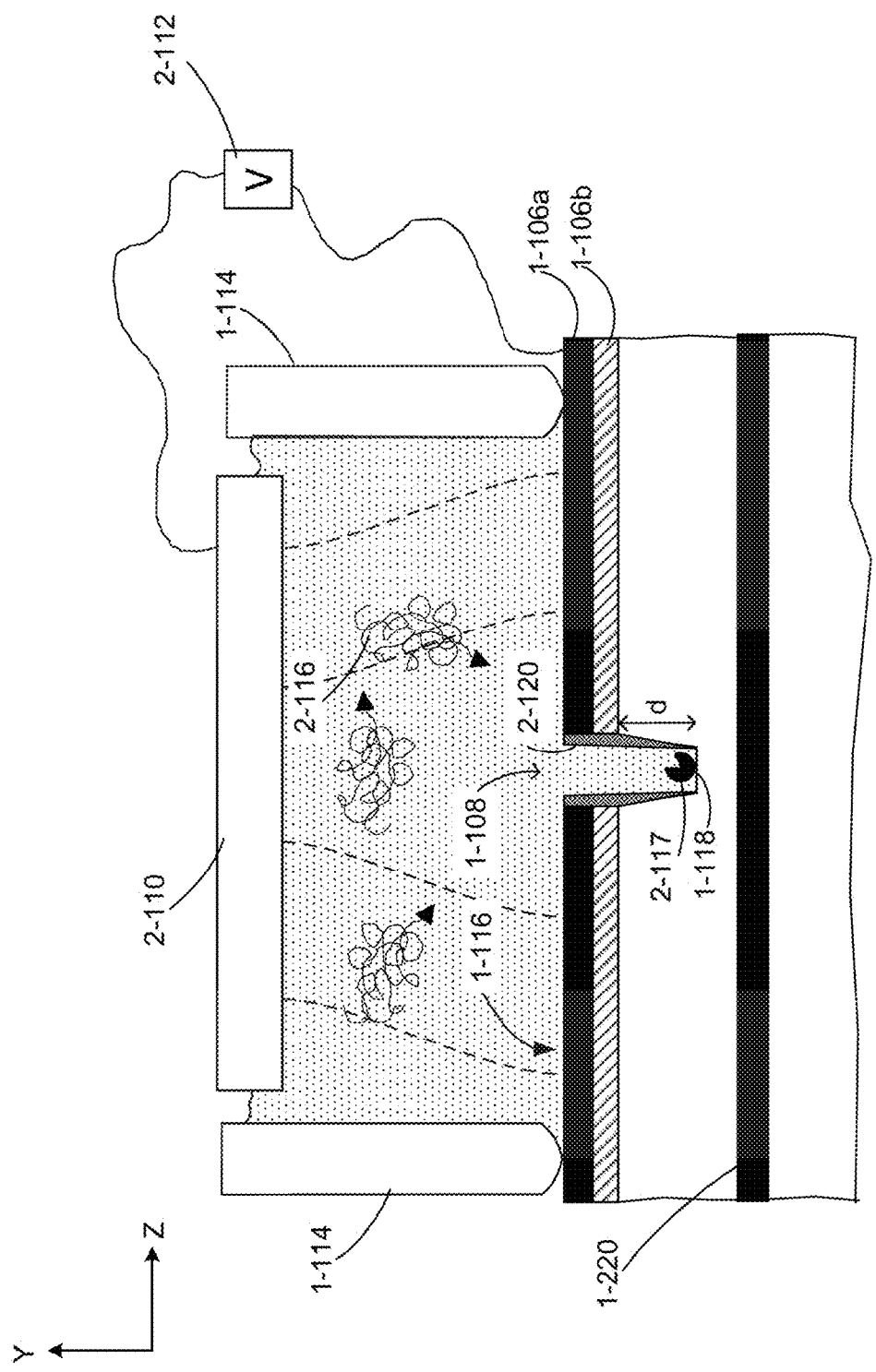
Figure 2:
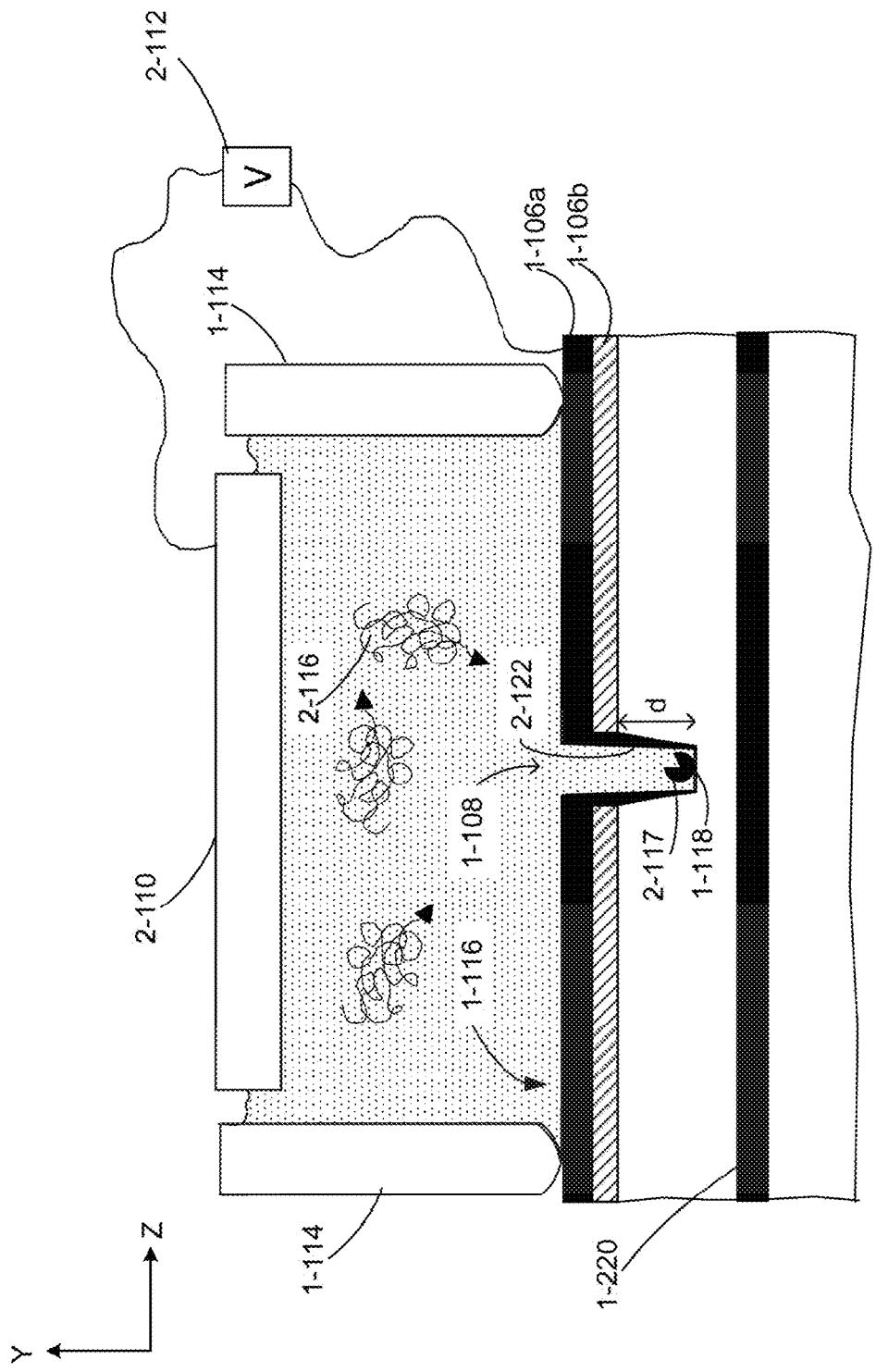

According to the techniques described herein, loading of a sample may include using electrokinetic sample loading techniques where the integrated device includes electrically conductive layer(s) formed into one or more electrodes configured to generate an electric field that operates to assist with loading a molecule of interest, for example, into a reaction chamber. In some embodiments, the integrated device may include a substrate having electrically conductive layer(s) and reaction chamber(s) of the integrated device may be formed in a surface of the substrate. FIG. 2-1 shows a schematic of a region of integrated device that includes a single reaction chamber 1-108. Sample reservoir 1-114 is shown around the reaction chamber, but it should be appreciated that more than one reaction chamber may be positioned on surface 1-116 of the integrated device and sample reservoir 1-114 may be positioned around the multiple reaction chambers. As shown in FIG. 2-1, a suspension retained within sample reservoir 1-114 may include molecules of interest 2-116 (e.g., template nucleic acid). In some embodiments, a molecule of interest 2-116 may preferentially bind or otherwise interact with a target 2-117 located at a bottom surface 1-118 of reaction chamber 1-108. In some embodiments, target 2-117 may include biotin, and a molecule of interest may include a region that preferentially binds to biotin, such as streptavidin. In embodiments where molecules of interest 2-116 are template nucleic acids, target 2-117 may include a polymerase, which may be immobilized on bottom surface 1-118. The polymerase may interact with a template nucleic acid within the reaction chamber such that the template nucleic acid is positioned in proximity to bottom surface 1-118.

As shown in FIG. 2-1, an integrated device may include electrically conductive layers 1-106a and 1-106b where reaction chamber 1-108 is formed through both layers 1-106a and 1-106b. Electrically conductive layers 1-106a and 1-106b may form one or more electrodes and may be configured to generate an electric field that operates to assist loading molecule of interest 2-116 into reaction chamber 1-108. One or both of electrically conductive layers 1-106a and 1-106b may electrically couple to circuitry 2-112. In the embodiment shown in FIG. 2-1, circuitry 2-112 is also configured to electrically couple to an external electrode 2-110, which is positioned separate from the integrated device and over surface 1-116 of the integrated device. As shown in FIG. 2-1, external electrode 2-110 may be separate from sample reservoir 1-114. In some embodiments, external electrode 2-110 may be integrated with sample reservoir 1-114 such that external electrode 2-110 and sample reservoir 1-114 are mechanically coupled. In other embodiments, external electrode 2-110 may be configured to be removably attached to sample reservoir 1-114 such that a user operating the system may attach and detach external electrode 2-110 to an interface of the sample reservoir 1-114. As shown in FIG. 2-1, external electrode 2-110 is positioned in contact with the fluid suspension within sample reservoir 1-114. It should be appreciated that some applications of the integrated device may involve a different placement of external electrode 2-110 relative to the suspension located within sample reservoir 1-114. In some embodiments, external electrode 2-110 may be positioned over the suspension such that external electrode 2-110 does not contact the suspension. In other embodiments, external electrode 2-110 may be submerged within the suspension.

Circuitry 2-112 is configured to apply electrical signal(s) to one or both of layers 1-106a and 1-106b and electrode 2-110 to generate the electric field that assists with loading molecule of interest 2-116 into reaction chamber 1-108. The electric field (depicted by the dashed lines) generated by the configuration shown in FIG. 2-1 may be configured to move a molecule of interest 2-116 towards surface 1-116 of the integrated device. The direction of the electric field can be controlled by the polarity of the electric signal applied between the electrode 2-110 and conductive layer(s) 1-106a, 1-106b. Some configurations may allow for an electric field to be generated in the vicinity of reaction chamber 1-108 where the electric field has a higher strength at surface 1-116 than at a distance distal from surface 1-116, such as within the bulk of the suspension deposited on surface 1-116. Molecules of interest 2-116 may move towards a region under the influence of the electric field such that the configuration shown in FIG. 2-1 drives electrokinetic movement of molecules towards surface 1-116, which may increase the total concentration of molecules at surface 1-116.

Circuitry 2-112 may be external to the integrated device, such as an external controller configured to provide a voltage signal to electrically conductive layers 1-106a and 1-106b. In some embodiments, circuitry 2-112 may be integrated as part of the integrated device. For example, electrical routing may be formed within the integrated device to electrically couple with one or both of layers 1-106a and 1-106b. Any suitable electrically conductive material may be used to form electrically conductive layers 1-106a and 1-106b, including titanium nitride (TiN), titanium, and aluminum (Al). In some embodiments, electrically conductive layer 1-106a, which forms surface 1-116, may include titanium nitride (TiN) and electrically conductive layer 1-106b may include aluminum (Al). In other embodiments, electrically conductive layer 1-106a may include aluminum (Al) and electrically conductive layer 1-106b may include titanium nitride (TiN). In some embodiments, an electrically conductive layer positioned proximate to a waveguide of the integrated device, such as waveguide 1-220, may act to reflect light propagating along the waveguide, which may improve optical properties of the integrated device, including increasing the amount of light propagating along the waveguide because light may be reflected back towards the waveguide.

Reaction chamber 1-108 may have any suitable depth. Since having a conductive layer, such as a metal layer, proximate to the bottom surface of a reaction chamber may impact optical properties of the integrated device, including optical properties associated with optical coupling of excitation light to the reaction chamber and with optical detection of light emitted from the reaction chamber, the depth of reaction chamber 1-108 may allow for desired optical properties of the integrated device. In some instances, an electrically conductive layer may act as a reflector for light emitted from the reaction chamber, which may improve collection of emission light by a photodetector of the integrated device. Some embodiments relate to relative positioning of the bottom surface from one or more electrically conductive layers to allow for desired optical properties of the integrated device. In some instances, the distance d between bottom surface 1-118 and electrically conductive layer(s) 1-106 may be in the range of 100 nm and 700 nm, or any value or range of values in that range. In some embodiments, distance d may be less than 400 nm.

In some embodiments, reaction chamber 1-108 may have one or more sidewalls 2-120, which may be formed of a suitable spacer material (e.g., titanium oxide ($TiO_2$)). The spacer material of sidewalls 2-120 may differ from the bottom surface 1-118 to prevent or reduce interaction of a molecule of interest with sidewalls 2-120 in comparison with the bottom surface 1-118 such that the molecule of interest preferentially binds or interacts with the bottom surface 1-118 over the sidewalls 2-120. Such a configuration may allow for selective binding, or other type of interaction, of a molecule of interest with bottom surface, which may further assist with suitable loading of a molecule of interest into a reaction chamber.

In some embodiments, one or more sidewalls of a reaction chamber may include electrically conductive material(s), where the sidewall(s) are electrically coupled to the electrically conductive layer(s) of the integrated device. FIG. 2-2 illustrates a cross-sectional schematic of an integrated device similar to that shown in FIG. 2-1 having electrically conductive sidewall(s) 2-122 of reaction chamber 1-108. Sidewall(s) 2-122 may electrically couple to electrically conductive layer(s) 1-106 such that applying electrical signals to electrically conductive layer(s) allows sidewall(s) 2-122 to also receive electrical signals and participate in generating an electric field. In some embodiments, sidewall(s) 2-122 may include an electrically conductive material that is also used to form one of the electrically conductive layers, such as electrically conductive layer 1-106a, as shown in FIG. 2-2. Any suitable electrically conductive material may be used to form electrically conductive sidewall(s) 2-122, including titanium nitride (TiN), titanium (Ti), tantalum (Ta), tantalum nitride (TaN), and tungsten (W). Using an integrated device having electrically conductive sidewall(s) of a reaction chamber may generate an electric field within reaction chamber 1-108, and in some embodiments may generate an electric field having a high strength near the bottom surface 1-118 of the reaction chamber 1-108. Such a configuration of an integrated device may increase movement of a molecule of interest towards the bottom surface 1-118 of reaction chamber 1-108.

Some embodiments relate to an integrated device that includes electrically conductive layer(s) 1-106 configured to form multiple electrodes in an integrated device. In such embodiments, external circuitry may electrically couple to two or more electrodes formed in the integrated device. These types of configurations may be used alone or in combination with an external electrode. In some embodiments, electrically conductive layer(s) may be configured to form a first electrode and a second electrode, where the first electrode and the second electrode are configured to receive electrical signal(s) to generate an electric field for electrokinetic sample loading. Such configurations may allow for electrokinetic sample loading without the use of an external electrode, which may improve ease of use for a user performing sample analysis. In embodiments where an external electrode is used in combination with a set of electrodes formed from electrically conductive layer(s), circuitry electrically coupled to the set of electrodes and to the external electrode may be configured to apply different electrical signals between different combinations of the electrodes, which may allow for improved loading of molecules into individual reaction chambers.

Figures 2, 3:
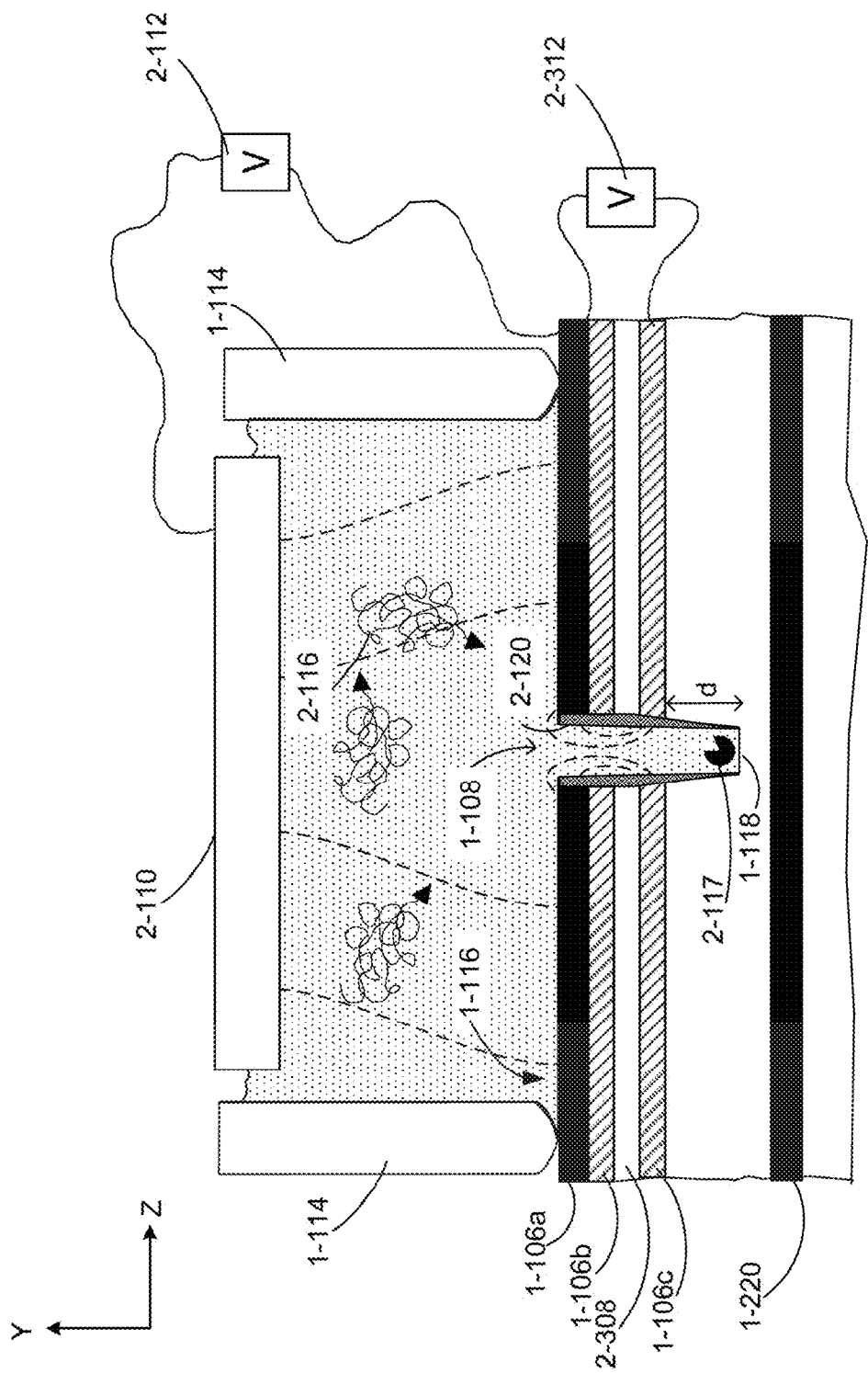

According to some embodiments, an integrated device may include multiple electrically conductive layers 1-106 configured to form two of more electrodes. The electrically conductive layers may be separated by dielectric material, which may reduce or prevent electrical current between the layers, allowing for electrical signals to be applied to the layers to generate an electrical field. FIG. 2-3 shows an exemplary configuration where electrically conductive layers form two electrodes as part of an integrated device. The integrated device shown in FIG. 2-3 includes electrically conductive layers 1-106a, 1-106b, and 1-106c where dielectric layer 2-308 is between electrically conductive layers 1-106b and 1-106c. In such a configuration, electrically conductive layers 1-106a and 1-106b may be considered to form a first electrode and electrically conductive layer 1-106c may be considered to form a second electrode. The two electrodes may be positioned relative to reaction chamber 1-108 to generate an electric field in the vicinity of reaction chamber 1-108 in response to the two electrodes receiving electrical signals from circuitry 2-312. It should be appreciated that any suitable number of electrically conductive layers may form two electrodes as long as there is dielectric material positioned between a first set of electrically conductive layers and a second set of electrically conductive layers to form the first and second electrodes.

As shown in FIG. 2-3, reaction chamber 1-108 is formed through dielectric layer 2-308 such that dielectric layer 2-308 has an opening that overlaps with reaction chamber 1-108. In some embodiments, the reaction chamber 1-108 may have tapered sidewalls such that a dimension of the opening of dielectric layer 2-308 forming reaction chamber 1-108 is smaller than a dimension of an opening of reaction chamber 1-108. For example, a cross-sectional dimension (e.g., along the z-direction as shown in FIG. 2-3) of the opening of dielectric layer 2-308 is smaller than a cross-sectional dimension (e.g., along the z-direction as shown in FIG. 2-3) of the opening of reaction chamber 1-108.

Examples of suitable dielectric material used to separate two electrically conductive layers in an integrated device includes silicon dioxide ($SiO_2$), titanium dioxide ($TiO_2$), tantalum oxide ($TaO_5$), hafnium oxide ($HfO_2$), and aluminum oxide ($Al_2O_3$).

As shown in FIG. 2-3, reaction chamber 1-108 is formed through electrically conductive layers 1-106a, 1-106b, and 1-106c. For an array of reaction chambers of an integrated device, individual reaction chambers may be formed through each of electrically conductive layers 1-106a, 1-106b, and 1-106c. The depth of reaction chamber 1-108 in these embodiments may depend on the relative depths of the electrically conductive layers. In some embodiments, distanced is between bottom surface 1-118 of reaction chamber 1-108 and the electrically conductive layer most proximate to bottom surface 1-118, which in the integrated device shown in FIG. 2-3 is electrically conductive layer 1-106c. In the embodiment shown in FIG. 2-3, reaction chamber 1-108 has sidewalls 2-120, which may include spacer material with limited or no electrical conductivity to prevent or limit electrical shorting between layers 1-106a, 1-106b and layer 1-106c.

In some embodiments, an integrated device may include an array of electrodes formed of electrically conductive layer(s) where individual electrodes in the array correspond to individual reaction chambers. In such embodiments, a first reaction chamber of the integrated device may correspond to a first electrode in the array and a second reaction chamber of the integrated device may correspond to a second electrode in the array. The first and second electrodes may be separated by dielectric material. Circuitry may apply electrical signals to individual electrodes in the array, which may allow for individual control of electric fields generated for different reaction chambers. Such a configuration may improve loading of molecules into reaction chambers because individual reaction chambers may be monitored to determine whether a molecule of interest is loaded for analysis and, if necessary, modifying the electrical signals applied to the electrode that corresponds to the reaction chamber to assist with sample loading. Additionally, in some cases, the applied electrical signals may be turned off, reduced, reversed, or reversed and reduced after the reaction chamber has been loaded with a sample.

Figures 2, 3, 4:
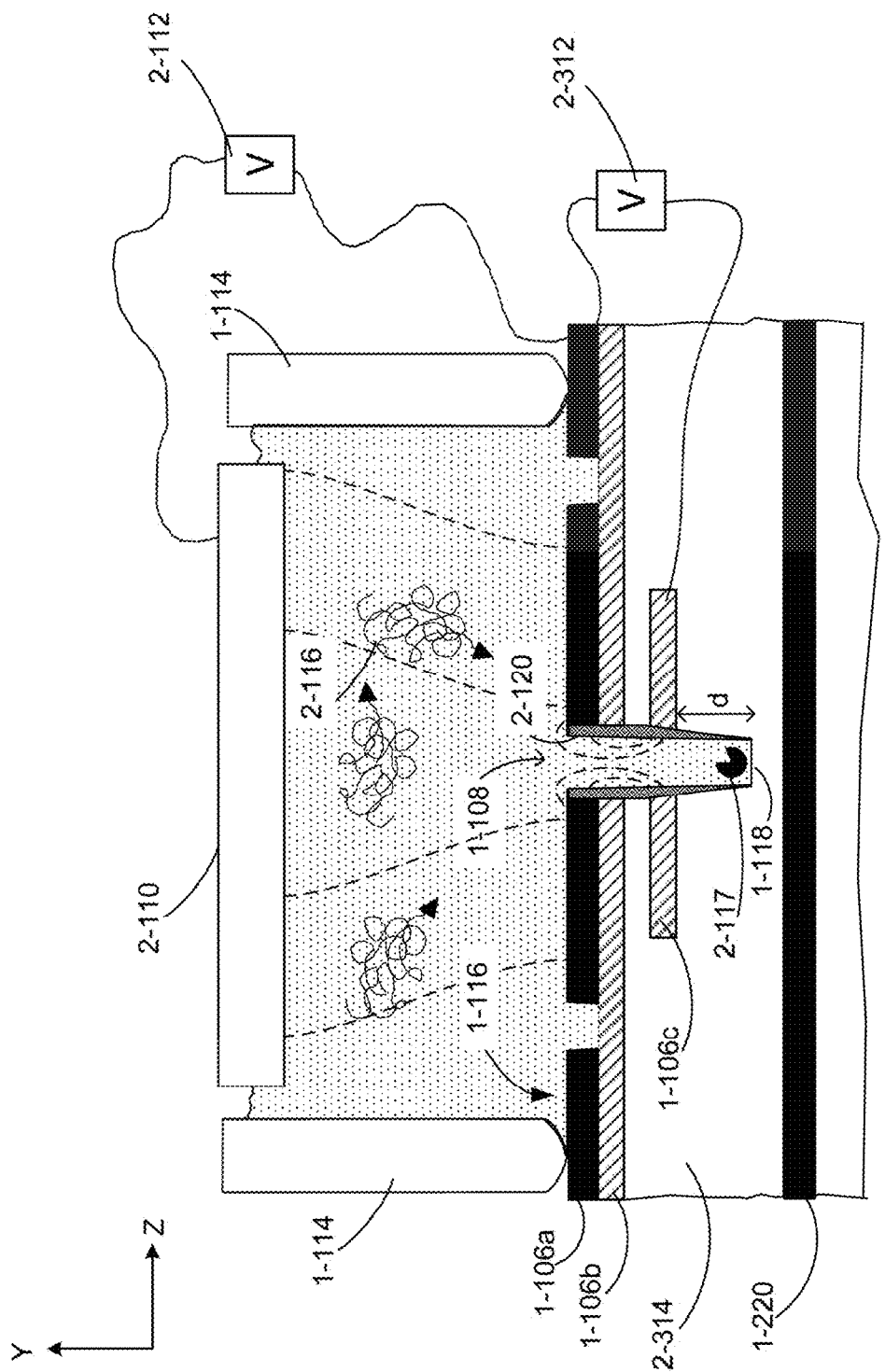

FIG. 2-4 illustrates a cross-sectional schematic of an integrated device where electrically conductive layers 1-106a and 1-106c are sized and shaped, at least in part, to form electrodes that correspond to the depicted reaction chamber 1-108. Circuitry 2-312 may electrically couple to electrically conductive layers 1-106a and 1-106c, e.g., with interconnects that are located out of the plane of the drawing, and may be configured to apply electrical signals to layer 1-106c and layers 1-106a, 1-106b. Although only one reaction chamber is shown in FIG. 2-4, it should be appreciated that within an array of reaction chambers of an integrated device, regions of electrically conductive layers 1-106a and/or 1-106c can be patterned and positioned to form electrodes that correspond to individual reaction chambers. For example, an electrically conductive layer(s) 1-106a and/or 1-106c can be patterned to form an isolated electrode surrounding or partially surrounding a reaction chamber. In top view, such an electrode may appear annular. The electrodes formed by electrically conductive layer 1-106c may be separated by dielectric material 2-314. As shown in FIG. 2-4, the individual reaction chambers may be formed through the discrete regions of electrically conductive layer 1-106c. For example, a first reaction chamber in the array may be formed through a first region of electrically conductive layer 1-106c and a second reaction chamber in the array may be formed through a second region of electrically conductive layer 1-106c where the first and second regions are separated by dielectric material. As another example, FIG. 2-9 shows an integrated device having multiple discrete electrically conductive layers 1-106c1 and 1-106c2 where a first reaction chamber is formed through layer 1-106c1 and a second reaction chamber is formed through layer 1-106c2. As shown in FIG. 2-9, layers 1-106c1 and 1-106c2 are separated by a region of dielectric material 2-614. In some embodiments, layers 1-106c1 and 1-106c2 are formed by depositing a layer of a suitable electrically conductive material and etching portions of the layer to form layers 1-106c1 and 1-106c2.

In some embodiments, sample loading using the integrated devices shown in FIG. 2-3 and FIG. 2-4 may include using external electrode 2-110 in addition to the two electrodes formed by electrically conductive layers 1-106a, 1-106b, and 1-106c. Circuitry configured to apply electrical signals to the electrically conductive layer(s) and the external electrode may include first circuitry 2-112 configured to apply electrical signals to the external electrode and one of the electrodes formed by electrically conductive layer(s) and second circuitry 2-312 configured to apply electrical signals to the two electrodes formed by electrically conductive layer(s). As shown in FIG. 2-3 and FIG. 2-4, circuitry 2-112 is electrically coupled to external electrode 2-110 and electrically conductive layer(s) 1-106a, 1-106b, and circuitry 2-312 is electrically coupled to electrically conductive layer 1-106c and electrically conductive layer(s) 1-106a, 1-106b. Example electric field lines are depicted as dashed lines in FIG. 2-3 and FIG. 2-4. According to some embodiments, the electrodes can be patterned to produce an electric field that has an increased intensity in a first region within 500 nm, for example, of an opening to the reaction chamber compared to a second region outside the first region. In some cases, the first region may have a radius larger or smaller than 500 nm, for example, between 100 nm and 2 microns.

As part of a sample loading process, operation of circuitry may include circuitry 2-112 and circuitry 2-312 applying different electrical signals to the electrodes coupled to circuitry 2-112 and circuitry 2-312. For example, electrical signals applied by circuitry 2-112 may assist with moving a molecule of interest towards surface 1-116 of the integrated device while electrical signals applied by circuitry 2-312 may assist with moving a molecule of interest into reaction chamber 1-108. Electrical signals applied by circuitry 2-112 and circuitry 2-312 may be applied simultaneously, according to some embodiments. In some embodiments, electrokinetic sample loading may proceed by applying electrical signals using circuitry 2-112 over a first duration of time and applying electrical signals using circuitry 2-312 over a second duration of time subsequent to the first duration of time.

In some implementations of electrokinetic sample loading, circuitry 2-112 may apply a first electrical signal between external electrode 2-110 and electrically conductive layer(s) 1-106a, 1-106b, and circuitry 2-312 may apply a second electrical signal different than the first electrical signal between electrically conductive layer 1-106c and electrically conductive layer(s) 1-106a, 1-106b. Circuitry 2-112 and circuitry 2-312 may apply the first electrical signal and the second electrical signal simultaneously, according to some embodiments. In other embodiments, circuitry 2-112 may apply the first electrical signal over a first duration of time and circuitry 2-312 may apply the second electrical signal over a second duration of time subsequent to the first duration of time. In this manner, applying the first electrical signal may move molecules of interest towards surface 1-116, and the combination of the first duration of time and the first electrical signal may allow for a desired concentration of molecules proximate to surface 1-116 to be achieved. Subsequent application of the second electrical signal may move molecules of interest into reaction chambers, and the combination of the second electrical signal and the second duration of time may allow for a desired amount of reaction chambers to become loaded with a molecule of interest.

Some embodiments relate to an integrated device that includes electrodes formed from the same set of electrically conductive layer(s), where the electrodes may be configured to receive electrical signals and generate an electric field to assist with loading of a molecule of interest into a reaction chamber. The electrodes may be formed by etching a region of the set of electrically conductive layer(s) to form two or more separate regions of the set of electrically conductive layers. FIG. 2-5 illustrates a cross-sectional schematic of an integrated device where electrically conductive layer(s) 1-106a and 1-106b form different electrodes. In particular, region 2-502 of electrically conductive layer(s) 1-106a and 1-106b has been etched to form a first electrode 2-520 and a second electrode 2-522. Circuitry 2-512 may be configured to electrically couple to first electrode 2-520 and second electrode 2-522, which may generate an electric field. First electrode 2-520 and second electrode 2-522 may be positioned relative to reaction chamber 1-108 to generate an electric field laterally over reaction chamber 1-108 upon application of electrical signals from circuitry 2-512. In such embodiments of the integrated device, surface 1-116 of the integrated device may have multiple electrodes arranged to correspond to one or more reaction chambers of the integrated device. Although an external electrode is not shown in FIG. 2-5, some embodiments may involve applying electrical signals to an external electrode positioned over reaction chambers and one or both of first electrode and 2-520 and second electrode 2-522. In some cases, region 2-502 may be etched all or nearly all the way around the reaction chamber 1-108 to form an annular shaped electrode.

Some embodiments relate to using circuitry of the integrated device, such as control circuitry associated with photodetectors of the integrated device, as one or more electrodes for electrokinetic sample loading. FIG. 2-6 illustrates a cross-section schematic of an integrated device where metal layer(s) 1-240 have been formed as part of the integrated device (e.g., as part of detection circuitry located below the reaction chambers 1-108). In some embodiments, at least a portion of the circuitry may be configured to receive electrical signals for generating an electric field to assist with electrokinetic sample loading of molecules into reaction chambers. For example, prior to or intermittently during operation of the detection circuitry, at least some of the metal layer(s) 1-240 can be biased with a signal used for sample loading. As shown in FIG. 2-6, metal layer(s) 1-240 formed within the integrated device are electrically coupled to photodetectors 1-110 to provide control signals to photodetectors 1-110 and/or receive readout signals from photodetectors 1-110. The integrated device may include a semiconductor (e.g., complementary metal-oxide-semiconductor (CMOS)) region 2-640, which may include metal layer(s) 1-240. Optical structures of the integrated device, including waveguide 1-220, may be formed within dielectric material 2-614 where reaction chamber 1-108 and semiconductor region 2-640 are separated by dielectric material 2-614.

Some embodiments relate to techniques for forming contacts with electrically conductive layer(s) of an integrated device that act as electrode(s) for electrokinetic sample loading. Forming the contacts and electrical connections between the contacts and electrically conductive layer(s) of the integrated device may occur as part of packaging of the integrated device. A packaging process of the integrated device may include adhering the integrated device to a printed circuit board. Conductive contacts on the package (e.g., printed circuit board) contact electrode(s) formed as part of the integrated device. In some embodiments, the conductive contacts of the package may receive electrical signals from an instrument, which may include circuitry configured to generate and apply electrical signals to the electrode(s) of the integrated device. In some embodiments, the conductive contacts of the package may contact a substrate of the integrated device (e.g., semiconductor die), which may include circuitry configured to generate and apply electrical signals to the electrode(s) of the integrated device. Additionally or alternatively, wire bonding may be used to electrically couple electrically conductive layer(s) of the integrated device to a part of a package of the integrated device and/or a substrate of the integrated device. Some embodiments may involve complementary-metal-oxide-semiconductor (CMOS) processing techniques to form an access region to electrically connect with an electrically conductive layer of the integrated device.

As shown in FIG. 2-6, semiconductor region 2-640 may be formed on substrate 2-602, such as a silicon die substrate. In some embodiments, substrate 2-602 may be attached to printed circuit board substrate 2-606 via bonding 2-604 (e.g., adhesive bonding). Contacts 2-608 and 2-610 may be formed on printed circuit board substrate 2-606. As shown in FIG. 2-6, contact 2-608 may electrically couple to metal layer(s) 1-240, such as by wire bonding contact 2-608 to metal layer(s) 1-240. Contact 2-610 may electrically couple to electrically conductive layer 1-106b. As shown in FIG. 2-6, a region of the integrated device is etched to form recessed region 2-612 to access metal layer(s) 1-240. Recessed region 2-612 and wire bonding to contacts 2-606 and 2-610 may occur as part of the packaging process of integrated device.

In some embodiments, a recessed region to access metal layer(s) may be formed and electrically conductive layer(s) may be formed over the recessed region to electrically connect a metal layer with the electrically conductive layer(s). The metal layer may be wire bonded to a contact, such as a contact on a printed circuit board substrate. As an example, FIG. 2-7 illustrates recessed region 2-612 to access metal layer 1-240a and electrically conductive layer 1-106b formed within recessed region and in contact with metal layer 1-240a. Recessed region 2-612 also contacts metal layer 1-240a and can allow for wire bonding with contact 2-608 of printed circuit board substrate 2-606.

In some embodiments, packaging component(s) may be used to form electrical connections between electrically conductive layer(s) of integrated device and metal layer(s) within a semiconductor region of the integrated device as part of forming an electrical contact with electrically conductive layer(s). For example a wire bond may pass over an electrically conductive layer and a component of the package may press the wire bond into contact with the electrically conductive layer, which may be considered as a "wire bond bridge." As shown in FIG. 2-8, package component 2-802 presses wire bond 2-804 into contact with electrically conductive layer 1-106a, forming a wire bond bridge. Wire bond 2-804 is in electrical contact with metal layer(s) 1-240, forming an electrical connection to contact 2-608.

Some embodiments relate to integrated devices having via structures electrically coupling conductive layer(s) in the integrated device to circuitry located within a semiconductor region of the integrated device. The circuitry in the integrated device may be configured to generate and apply electrical signals to the electrically conductive layer(s) through the via structures. FIG. 2-9 shows an exemplary cross-sectional schematic of an integrated device having conductive via 2-910 formed to electrically couple conductive layer 1-106*c*1 to metal layer 1-240*a*, which is positioned in semiconductor region 2-640. Similarly, via 2-920 is shown in FIG. 2-9 to electrically couple conductive layer 1-106*c*2 to metal layer 1-240*b*. For illustrative purposes, waveguide 1-220 is shown with dotted lines in FIG. 2-9 to indicate the relative positioning of waveguide 1-220 with other structures of the integrated device, but is not included in the plane shown in FIG. 2-9 as conductive vias 2-910 and 2-920 are located away from waveguide 1-220 so they do not intrude upon the waveguide structure. Although the electrode configuration shown in FIG. 2-9 is similar to the configuration shown in FIG. 2-4 in that there is an electrically conductive layer corresponding to individual reaction chambers, it should be appreciated that such via structures may be implemented to electrically connect an electrically conductive layer forming an electrode that may assist with sample loading across multiple reaction chambers.

Regardless of the configuration of electrodes used for electrokinetic sample loading, the electrical signals generated by circuitry coupled and applied to the electrodes may have any suitable parameters (e.g., amplitude, temporal profile, duty cycle, frequency) for achieving loading of molecules into reaction chambers 1-108. In some embodiments, parameters of the applied electrical signals may be selected to achieve a desired level of efficiency in loading molecules across an array of reaction chambers. For example, parameters of the electrical signals may be selected to reduce the amount of time needed to achieve sample loading for a particular number, percentage, or ratio of reaction chambers in an array of reaction chambers compared to when the electrical signals are not applied during loading of the reaction chambers 1-108. Some embodiments involve circuitry generating and applying a time-varying voltage signal to electrically conductive layer(s), and in some embodiments, to an external electrode. In some cases, DC or exponentially decaying signals may be used.

Figures 1A, 3:
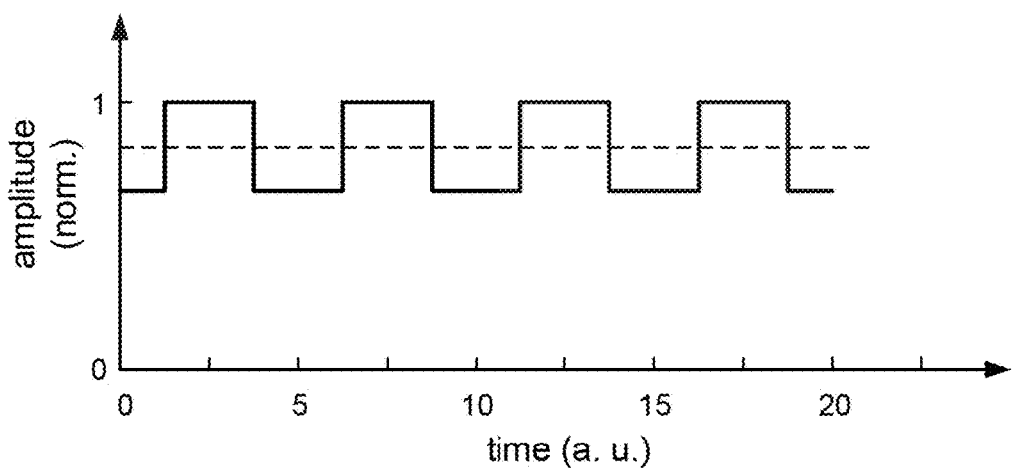
Figures 1B, 3:
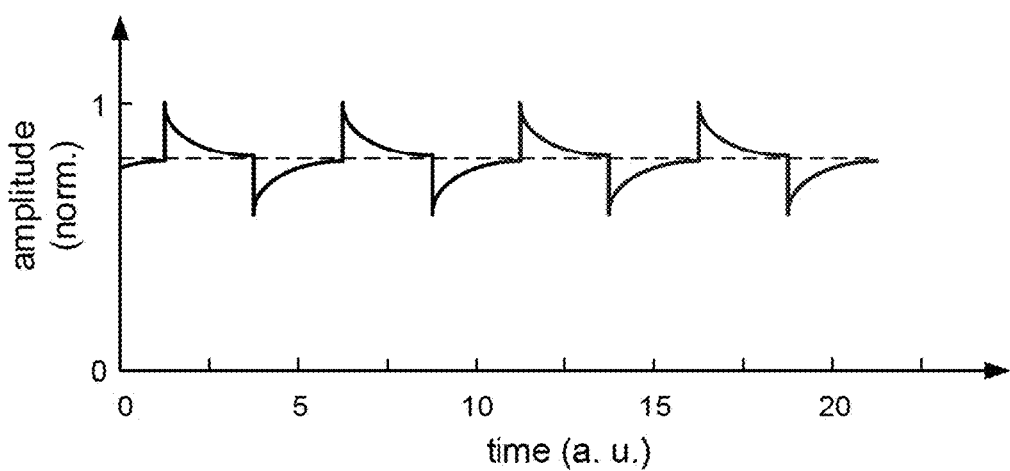
Figures 2, 3:
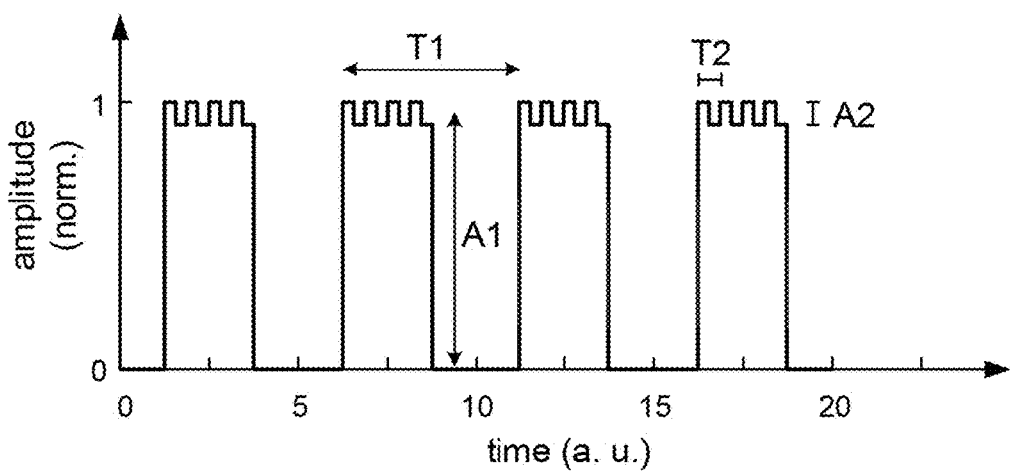

FIG. 3-1A depicts an example time-varying voltage signal having a square waveform that may be applied to an electrode of a reaction chamber 1-108, according to some embodiments. In some embodiments, an applied waveform may have a DC offset, indicated by the dashed lines in FIG. 3-1A and FIG. 3-1B. The DC offset can provide an electric field near the reaction chamber 1-108 that draws a sample toward the reaction chamber. FIG. 3-1B depicts an example current response to the square waveform. Application of such a time-varying voltage signal may allow for unidirectional movement of a molecule of interest towards a surface of an integrated device, and in some instances, into a reaction chamber. It should be appreciated that other types of time-varying electrical signals may be implemented for electrokinetic sample loading, including time-varying voltage signals having a sinusoidal waveform, a sawtooth waveform, and triangle waveform. A peak voltage of an applied waveform may be between 50 millivolts and 5 volts. In some implementations, improved performance is obtained when a peak voltage of an applied waveform is between 0.5 volt and 1 volt. A frequency of an applied waveform may be between 0.1 Hz and 10 kHz. In some embodiments, the applied voltage and frequency can be within 10% of the end values in these ranges.

In some embodiments, the time-varying voltage signal applied to electrodes for electrokinetic sample loading may include a combination of multiple periodic waves (e.g., superposition or multiplication of two or more waveforms). One or more of the applied waveforms can include a DC bias in some cases. The time-varying voltage signal may include a first periodic wave with a first frequency and a first amplitude in addition to a second periodic wave with a second frequency and a second amplitude. The first and second frequencies may differ, and in some embodiments, the first frequency is less than the second frequency. Similarly, the first amplitude and the second amplitude may differ, and in some embodiments, the first amplitude is greater than the second amplitude. FIG. 3-2 depicts a combination, time-varying voltage signal comprising a first square waveform having a period T1 and amplitude A1 and a second square waveform having a second period T2 and amplitude A2. As shown in FIG. 3-2, period T1 is greater than period T2, and amplitude A1 is greater than amplitude A2. Although combined square waveforms are shown, any combination of other waveforms (sinusoidal, triangle, sawtooth, exponential decay, etc.) may be used in some embodiments, Further, combined waveforms can be of different types (e.g., square wave and sinusoidal wave).

According to some implementations, electrodes for all reaction chambers may be connected together such that an applied signal produces a corresponding electric field at all reaction chambers on an integrated device. In some cases, there may be a plurality of electrodes that are isolated from each other for receiving applied signals to produce electric fields at the reaction chambers 1-108. In such cases, a first set of electrodes may create a first electric field for a first group of reaction chambers, a second set of electrodes may create a second electric field for a second group of reaction chambers, and so forth. In some cases, different signals may be applied to create different electric fields for the different groups of reaction chambers. Alternatively or additionally, signals may be applied at different times to load groups of reaction chambers at different times. In some implementations, biasing circuitry can be arranged similar to read-out circuitry for photodetector arrays, so that electrodes for reaction chambers may be individually addressed to create an electric field at each reaction chamber 1-108 (or row of reaction chambers, or column of reaction chambers) independently of all other reaction chambers.

During use of the integrated device for sample analysis, a user may introduce a suspension (e.g., pipetting a particular suspension volume) having molecules of interest proximate to a surface of the integrated device. For example and referring again to FIG. 1-1, a user may deposit the suspension on surface 1-116 and/or within pixel region 1-203 of the integrated device. The recessed pixel region 1-203 and/or sample reservoir 1-114 may act to retain the suspension proximate to the surface, such that the suspension does not substantially flow from the pixel region 1-203 where the reaction chambers are located. Electrokinetic sample loading, according to the techniques described herein, may be used to load molecules of interest from a deposited suspension into individual reaction chambers. Such techniques may include applying electrical signal(s) to a first and second electrode to generate an electric field that operates to assist loading a molecule of interest into a reaction chamber of the integrated device. One or both of the first and the second electrodes may include electrically conductive layer(s) of the integrated device. The electric field may be generated in a vicinity of a surface of the integrated device and configured to move the molecule of interest in a direction towards a bottom surface of the reaction chamber. In some embodiments, the generated electric field may be configured to separate the molecule of interest from other components in the suspension (e.g., sample debris, crowding agents, condensing agents). In some embodiments, introducing the suspension on the surface of the integrated device may include introducing a crowding agent and/or a condensing agent in combination with the sample. Additional details on crowding agents and condensing agents are described herein including in Section III below.

Some embodiments may involve modulating the electrical signal applied to the electrodes using information identifying whether molecules have been loaded into individual reaction chambers of the integrated device. For example, individual molecules may be labeled with one or more fluorescent markers, which may be used for identifying whether a molecule is loaded in a reaction chamber by illuminating the reaction chamber with light that excites the fluorescent marker(s) and using photodetector(s) corresponding to the reaction chamber to detect any light emitted from the reaction chamber, which may include light emitted by the fluorescent marker(s), in response to the illuminating the reaction chamber. Using this feedback information, individual reaction chambers may be monitored during electrokinetic sample loading to determine whether molecules have been loaded into individual reaction chambers.

In some applications, this feedback information may inform when to change the type of electrical signal that is applied to the electrodes during the sample loading process. For example, an electrical signal used for loading molecules may be applied initially to the electrodes to allow for loading of the molecules into individual reaction chambers and a different electrical signal may be applied to the electrodes in response to receiving feedback information identifying that a desired number of reaction chambers have been loaded with a molecule. The electrical signal applied in response to receiving the feedback information may be configured to generate an electric field that acts to reduce movement of molecules into individual reaction chambers and/or reduce movement of a loaded molecule out of the reaction chamber in which it is loaded. Such an electrical signal may be considered as a "reverse electrical signal" because it acts to prohibit or reduce further loading of molecules into reaction chambers. Such techniques may further improve loading of molecules into reaction chambers by allowing for active monitoring of the reaction chambers and modifying the electrical signals applied to the electrodes to account for this feedback information.

In embodiments where an electric signal is applied to electrodes such that an electric field is generated for a group of reaction chambers, feedback information may include information from monitoring across the group of reaction chambers and may provide an indication of a number of reaction chambers in the group that are loaded with a molecule. In such embodiments, the reverse electrical signal may be applied to the electrodes in response to receiving an indication that the number of reaction chambers in the group that are loaded with a molecule is equal to or above a threshold number of reaction chambers that are loaded with a molecule.

In embodiments where electrical signals are applied to electrodes such that the electric field associated with individual reaction chambers can be modulated, such as in the embodiments of the integrated devices shown in FIG. 2-4, FIG. 2-7, and FIG. 2-9, feedback information may include information associated with whether particular reaction chambers are loaded with a molecule. In such embodiments, a reverse electrical signal may be applied to electrodes associated with individual reaction chambers that have been identified as being loaded with a molecule based on the feedback information. In this manner, different electric fields may be generated proximate to different reaction chambers such that reaction chambers that have yet to be loaded with a molecule have an electric field configured to assist with sample loading while those reaction chambers that have been identified as having a loaded molecule have an electric field to reduce or prevent additional molecules from entering the reaction chamber.

An aspect of performance of the integrated device may relate to the diffusion of components in a suspension in/out of the reaction chamber during operation of the integrated device (e.g., during analyses of samples). As an example, a DNA complex that is retained in a reaction chamber 1-108 can be quite large (have a large pervaded volume), and the replication product is growing in size during a sequencing run. In some cases, a large DNA complex may occupy much of the volume of the reaction chamber, and thereby limit the diffusion rate of fluorescently-labeled nucleotides to the bottom of the reaction chamber. A reduced diffusion rate of the labeled nucleotides can limit the sequencing speed (and fluorescent pulse rate) as well as the sequencing read length. To improve the diffusion rate, electrical signals may be applied to the electrodes during a sequencing run, for example, to pull at least one untethered end of the DNA out of the reaction chamber. This would be done in a way that is similar to the "reverse electrical signal" described above except that such a signal would be applied during sequencing or sample analysis when molecules or proteins having large pervaded volumes are retained in reaction chambers. In some cases, a signal applied to the electrodes during sample analysis may be pulsed periodically to pull the sample at least partly out of the well. Such a signal may be applied to electrodes of reactions chambers individually for each chamber, applied to groups of chambers, or applied to all or nearly all reaction chambers on a chip.

Circuitry configured to apply electrical signals to the electrodes used for electrokinetic sample loading may apply different types of signals. In some embodiments, the circuitry may apply a first electrical signal configured to move a molecule of interest towards a surface of the integrated device, and apply a second electrical signal configured to move the molecule of interest within the reaction chamber. In some instances, the first electrical signal is applied to a first electrode and a second electrode, and the second electrical signal is applied to the second electrode and a third electrode.

As discussed above in connection with the different electrode configurations, circuitry may apply electrical signals to any suitable combination of electrodes, including electrodes formed of electrically conductive layer(s) as well as external electrodes. In some embodiments, circuitry may be configured to apply electrical signals to a first electrode that includes a first subset of electrically conductive layer(s) and a second electrode that includes a second subset of electrically conductive layer(s) that is separated from the first subset by dielectric material. In some embodiments, circuitry may be configured to apply electrical signals to a first electrode and a second electrode formed of the same electrically conductive layer(s). In such embodiments, the first electrode includes a first region of the electrically conductive layer(s) and the second electrode includes a second region of the electrically conductive layer(s) where the first and the second regions are separated by dielectric material. In some embodiments, circuitry may be configured to apply electrical signals to a first electrode that includes electrically conductive layer(s) and a second electrode external to the integrated device.

Fabrication of the electrically conductive layer(s) to be formed as electrodes of an integrated device may use any suitable silicon-based fabrication processing (e.g., complementary metal-oxide-semiconductor (CMOS) processing). In embodiments that implement a wire bond contact, such as wire bond contact of electrically conductive layer 1-106*b* to contact 2-610 shown in FIG. 2-6, fabrication may include formation of a metal layer in contact with an electrically conductive layer and exposing the metal layer to form a wire bond contact. The metal layer may have a thickness in the range of 100 nm to 800 nm, or any value or range of values in that range. The thickness of the metal layer may allow for a robust contact region for wire bonding or an electrically conductive layer formed over the metal layer.

Figures 1A, 4:
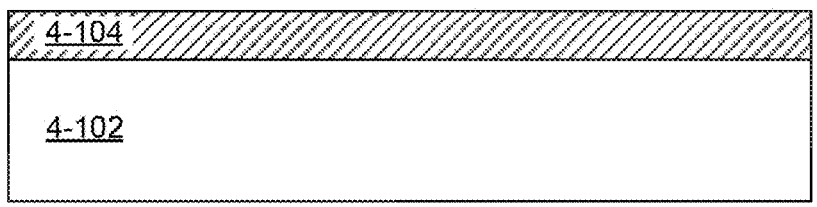
Figures 1B, 4:
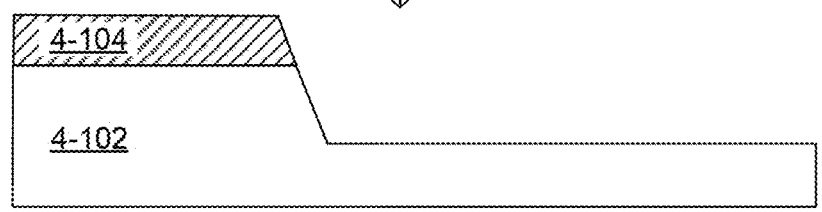
Figures 1C, 4:
Figures 1D, 4:
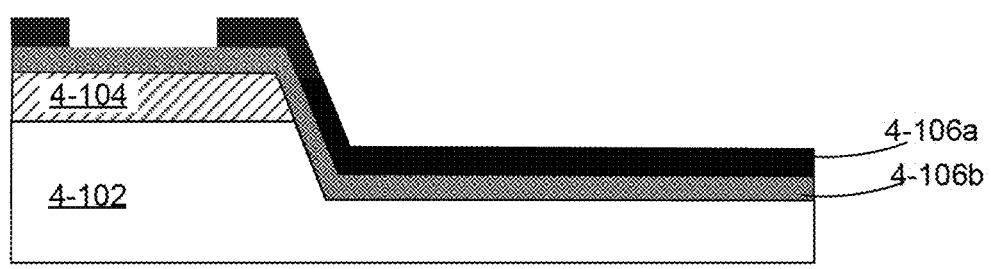

FIGS. 4-1A through FIG. 4-1D show structures associated with an exemplary process for forming a metal layer for a wire bond contact to an electrically conductive layer used to form an electrode in an integrated device. The first step shown in FIG. 4-1A includes forming a metal layer 4-104 (e.g., aluminum (Al)) over dielectric layer 4-102. Metal layer 4-104 may have a thickness in the range of 100 nm to 800 nm, or any value or range of values in that range. Although not shown in FIG. 4-1A, some embodiments may involve forming one or more adhesion layers (e.g., titanium, titanium nitride) underneath metal layer 4-104. The second step shown in FIG. 4-1B includes etching a portion of metal layer 4-104 into dielectric layer 4-102, which may form a region of the resulting integrated device having reaction chambers, such as pixel region 1-203 shown in FIG. 1-1. The third step shown in FIG. 4-1C includes forming electrically conductive layers 4-106*a* and 4-106*b* over etched metal layer 4-104 and dielectric layer 4-102. In some embodiments, electrically conductive layer 4-106*b* includes aluminum and electrically conductive layer 4-106*a* includes titanium nitride. The fourth step shown in FIG. 4-1D includes etching a portion of electrically conductive layer 4-106*a* over metal layer 4-104 to expose electrically conductive layer 4-106*b*. Etching electrically conductive layer 4-106*a*, and other etching steps described herein, may include using any suitable lithography and etching techniques. For example, a resist may be applied and patterned to mask regions that are not etched, and the resist can be removed after the etching is completed.

Figures 2A, 4:
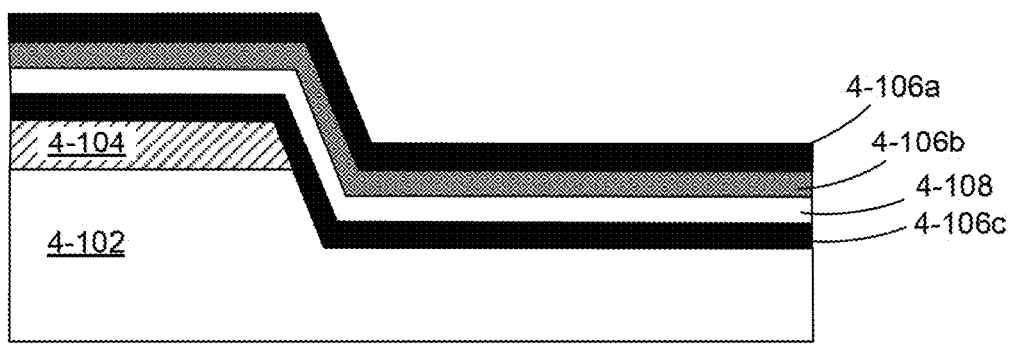
Figures 2B, 4:
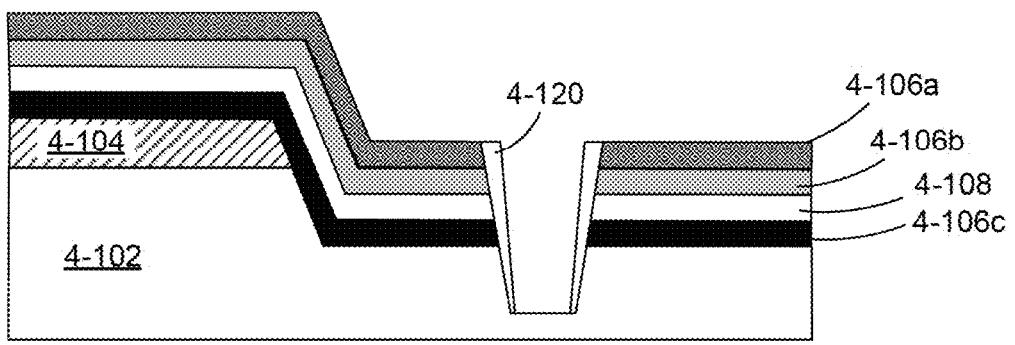
Figures 2C, 4:
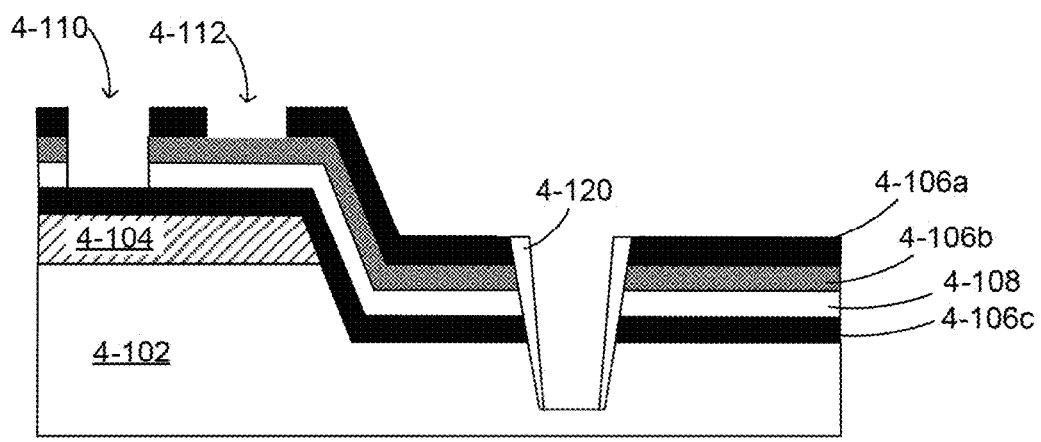
Figures 3, 4:
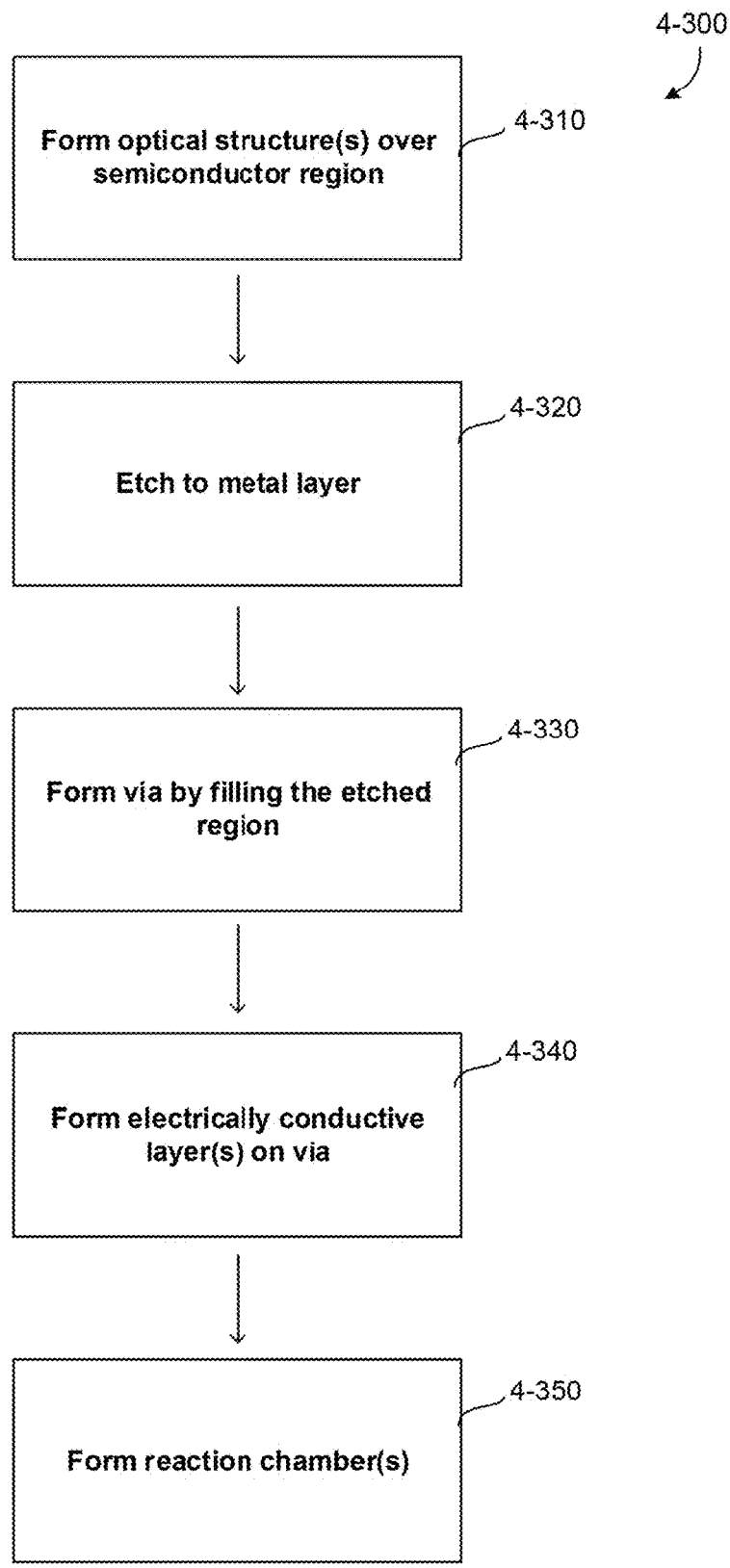

FIGS. 4-2A through FIG. 4-2C show structures associated with an exemplary process for forming contacts to electrically conductive layers that may act as electrodes in an integrated device. The first step shown in FIG. 4-2A may occur after etching a metal layer 4-104 and dielectric material 4-102, such as shown in FIG. 4-1B, and comprise forming electrically conductive layer 4-106*c*, dielectric layer 4-108, electrically conductive layer 4-108*b*, and electrically conductive layer 4-106*a* over the etched metal layer 4-104 and dielectric material 4-102. The second step shown in FIG. 4-2B includes etching through layers 4-106*a*, 4-106*b*, 4-108, and 4-106*c* and dielectric material 4-102 to form a reaction chamber. This step may also include forming sidewall(s) 4-120 on the sides of the etched reaction chamber. The third step shown in FIG. 4-2C includes etching contact opening 4-110 through layers 4-106*a*, 4-106*b*, and 4-108 over metal layer 4-104 to expose electrically conductive layer 4-106*c*. This step may also include etching contact opening 4-112 through layer 4-106*a* to expose electrically conductive layer 4-106*b*. The resulting integrated device may have a configuration similar to that shown in FIG. 2-3. It may be appreciated that sub-steps (e.g., resist deposition, patterning, removal, cleaning, additional etching, etc.) may be carried out to obtain the structures shown in FIG. 4-1A through FIG. 4-1D, FIG. 4-2A through FIG. 4-2C, and FIG. 4-4A through FIG. 4-4C.

Some embodiments relate to fabrication of one or more via(s) within an integrated device to connect electrically one or more conductive layer(s) to one or more metal layer(s), which may be formed as part of a semiconductor region. Individual vias may be formed prior to formation of the electrically conductive layer(s) that electrically couples to a via. FIG. 4-3 illustrates steps of an exemplary method 4-300 of forming via(s) during fabrication of an integrated device, such as the integrated device shown in FIG. 2-9. In step 4-310, optical structure(s) (e.g., waveguides) of the integrated device are formed over a semiconductor region of the integrated device. With reference to FIG. 2-9, step 4-310 may include forming waveguide(s) 1-220 in dielectric material 2-614 over semiconductor region 2-640, which includes metal layers 1-240*a* and 1-240*b*. In some embodiments, step 4-310 may include one or more steps of chemical-mechanical planarization (CMP) processing to form a planarized surface for dielectric material 2-614 (e.g., as the dielectric material 2-614 is built up and integrated structures formed). In embodiments where the integrated device includes a recessed or trench region, such as the recessed region 2-905 within pixel region 1-203 shown in FIG. 2-9, the recessed region 2-905 may be formed in step 4-310 after dielectric deposition and CMP steps, for example.

The method 4-300 may can comprise step 4-320, which includes etching vias through to access metal layer(s) in the semiconductor region. The etching performed in step 4-320 may include etching through dielectric material, such as dielectric material 2-614, and/or some of the material in semiconductor region 2-640 shown in FIG. 2-9, to form openings that access the metal layers. The method 4-300 can further comprise step 4-330, which includes forming a conductive via 2-910, 2-920 by filling the etched openings with electrically conductive material(s). An example of a suitable material used to fill the etched openings is tungsten. Step 4-330 may include any suitable metallization processing techniques, including chemical vapor deposition (CVD). In some embodiments, chemical-mechanical planarization (CMP) processing may be used following deposition of the electrically conductive material(s) in the etched openings to remove excess metal deposition and to form a planarized surface over the waveguide leaving conductive plugs (also referred to as conductive vias) filling the etched openings. In some embodiments, lithography and etching techniques may be used following deposition of the electrically conductive material(s) in the etched openings to remove residual material over the waveguide, which may otherwise impact optical performance of the waveguide and/or other optical structures of the resulting integrated device.

The method 4-300 can further comprise step 4-340, which includes forming the electrically conductive layer(s) 1-106*c*1, 1-106*c*2 on the conductive via(s) 2-910, 2-920, for example. The electrically conductive layer(s) may be formed using a suitable deposition process, including chemical vapor deposition (CVD). Referring to FIG. 2-9, electrically conductive layers 1-106*c*1 and 1-106*c*2 may be formed at step 4-340. The method 4-300 can further comprise step 4-350, which includes forming additional layers, including electrically conductive layer(s) 1-106a, 1-106b and dielectric layer(s), over the electrically conductive layer(s) formed in step 4-340, and forming reaction chamber(s) through the deposited layers. In some cases, the recessed region 2-905 can be etched in one or more dielectric layers that have been deposited over electrically conductive layer(s) 1-106a, 1-106b. Examples of suitable dielectric materials that may be formed over the electrically conductive layer(s) include silicon dioxide ($SiO_2$), titanium dioxide ($TiO_2$), tantalum oxide ($TaO_5$), hafnium oxide ($HfO_2$), and aluminum oxide ($Al_2O_3$).

Referring to FIG. 2-9, dielectric material 2-614 and electrically conductive layers 1-106a, 1-106b may be formed over electrically conductive layers 1-106c1 and 1-106c2. Forming reaction chamber(s) 1-108 may include a multi-step etch process through one or more electrically conductive layers and dielectric layer(s). As shown in FIG. 2-9, reaction chambers 1-108 are formed through electrically conductive layers 1-106a, 1-106b, and 1-106c1, 1-106c2 and into dielectric material 2-614. In some embodiments, step 4-350 may include forming spacer material on the sidewall(s) of the reaction chamber(s). For example, spacer material on sidewalls 2-120 as shown in FIG. 2-9 may be formed in step 4-350.

Figures 4, 4A:
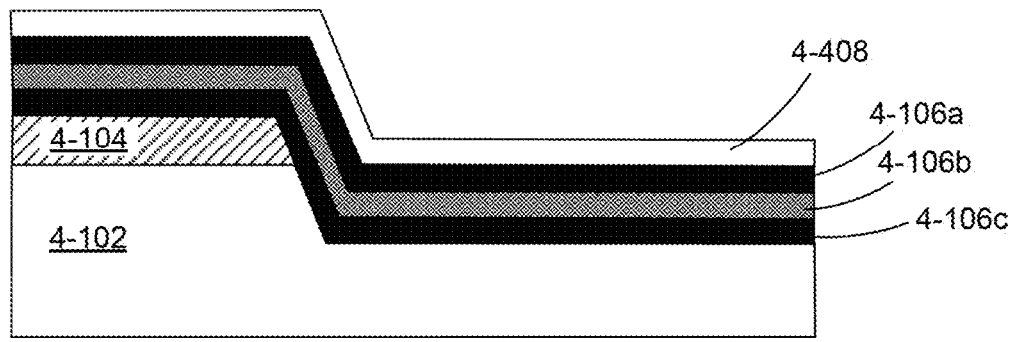
Figures 4, 4B:
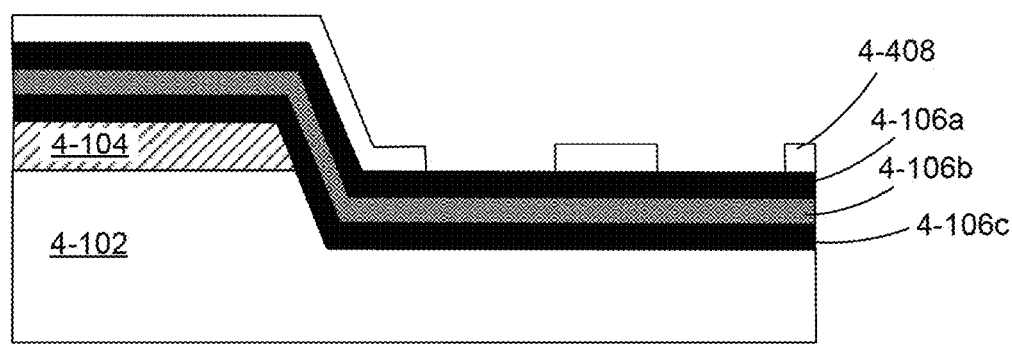
Figures 4, 4C:
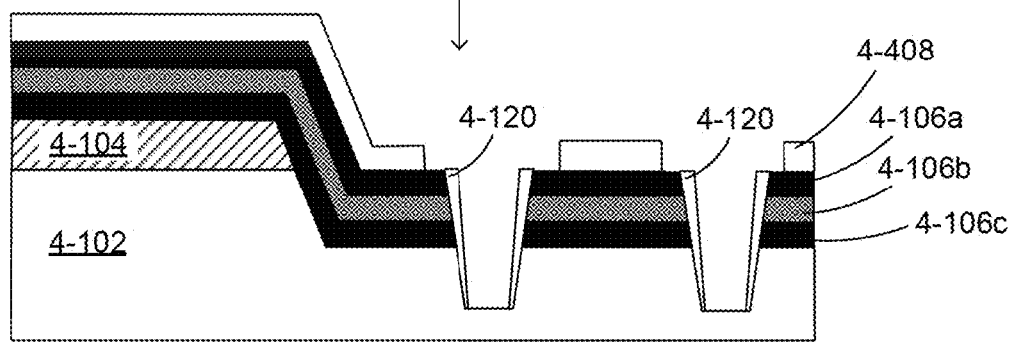

Some embodiments of an integrated device may have a surface 1-116 formed, at least partially, of dielectric material. In some embodiments, one or more layers of dielectric material may be formed over the electrically conductive layer(s) and regions of the one or more layers may be removed to correspond to positions of individual reaction chambers. In this manner, the resulting surface of the integrated device may be considered to have a "perforated dielectric layer." Such a configuration of an integrated device may allow for generating an electric field having a particularly high electric field proximate to the reaction chambers. FIG. 4-4A through FIG. 4-4C show structures associated with an exemplary process for forming a perforated dielectric layer. The first step shown in FIG. 4-4A may occur after etching a metal layer 4-104 and dielectric material 4-102, such as shown in FIG. 4-1B, and comprise forming electrically conductive layer 4-106c, electrically conductive layer 4-108b, electrically conductive layer 4-106a, and dielectric layer 4-408 over the etched metal layer 4-104 and dielectric material 4-102. The second step shown in FIG. 4-4B includes etching through dielectric layer 4-408 in regions to expose electrically conductive layer 4-106a. Etching dielectric layer 4-408 may include using any suitable lithography and etching techniques. The third step shown in FIG. 4-4C includes etching through layers 4-106a, 4-106b, 4-108, and 4-106c to form individual reaction chambers at locations corresponding to the exposed regions of electrically conductive layer 4-106a. This step may also include forming sidewall(s) 4-120 on the sides of the etched reaction chamber. Although only one dielectric layer is shown as dielectric layer 4-408, it should be appreciated that any suitable number of layers of dielectric material may be formed over the electrically conductive layer(s). Examples of dielectric materials that may be used to form dielectric layer 4-408 include silicon dioxide ($SiO_2$), titanium dioxide ($TiO_2$), tantalum oxide ($TaO_5$), hafnium oxide ($HfO_2$), aluminum oxide ($Al_2O_3$), and other metal oxides.

III. Additional Sample Loading Techniques

Among other aspects, the present application describes devices and methods for loading a sample of interest into a reaction chamber. In some aspects, techniques described herein involve steps of contacting a suspension containing samples (e.g., molecules, proteins, or particles of interest) to a surface 1-116 of an integrated device comprising at least one reaction chamber having a bottom surface distal to the surface of the integrated device. A suspension may comprise a liquid solution that contains a plurality of samples that is placed in recessed region 2-905. In some cases, a suspension may comprise a liquid in which the samples are dissolved. In some cases, a suspension may comprise a liquid in which the samples are dispersed. The term "suspension" is used herein to refer to either type of sample mixture. A suspension can further include reaction components that participate in a reaction that takes place in a reaction chamber. In some embodiments, the suspension may be contacted with a crowding agent that further directs the samples toward the bottom surface of the reaction chamber. In some embodiments, the suspension may be contacted with a condensing agent that condenses (e.g., compacts) the samples. In some embodiments, the bottom surface of the reaction chamber comprises a coupling moiety configured to bind the sample of interest, under conditions suitable to permit binding of the sample to the coupling moiety, thereby coupling the sample to the bottom surface of the reaction chamber.

In some aspects, devices and methods described herein may be useful in techniques that allow for the detection of an individual sample in a suspension. The individual sample may be, by way of example and not limitation, an amino acid, a polypeptide, a nucleotide, and/or a nucleic acid. For example, in some embodiments, devices and methods provided in the present application may be used in conjunction with single molecule nucleic acid sequencing technologies. Single molecule nucleic acid sequencing allows for the determination of a sequence of a single template nucleic acid molecule by monitoring, in real time, the extension of a nucleic acid molecule that is complementary to the template nucleic acid.

In certain techniques, single molecule nucleic acid sequencing is performed by isolating single sequencing templates within each of a plurality of reaction chambers. In many applications, however, the total volume of these reaction chambers relative to the total suspension volume is considerably low. Additionally, the concentration of sequencing template in a suspension that is required to minimize multiple templates in single reaction chambers is often so low that the kinetics of loading the sequencing templates into the reaction chambers can severely limit the amount of successfully loaded and sufficiently active complexes.

In certain techniques, it is preferable for a single reaction chamber to comprise a single sample of interest (e.g., a single sequencing template). Accordingly, in some embodiments, when loading a suspension that comprises, for example, a sequencing template, onto an integrated device comprising an array of reaction chambers, care must be taken to avoid oversaturating the integrated device with a high concentration of the sequencing template. It is often advisable, in such instances, to load suspensions having a dilute concentration of sequencing template.

Without wishing to be bound by theory, it is postulated that the distribution of sequencing templates in a suspension of dilute concentration across an array of reaction chambers is best modeled by a Poisson distribution. This discrete probability distribution predicts that approximately 37% of the reaction chambers in an array will contain one sequencing template, with the remaining reaction chambers containing either zero or multiple sequencing templates. In practice, achieving 37% single occupancy across an array of reaction chambers can be complicated by any number of chemical and/or mechanical variables. In some aspects, devices and methods described herein advantageously increase the percentage of single occupancy across an array of reaction chambers.

In some embodiments, devices and methods described herein are capable of achieving single occupancy of molecules of interest in an array of reaction chambers that is comparable to, approximately the same as, or greater than the amount predicted by Poisson statistics. For example, in some embodiments, devices and methods of the present disclosure may achieve single occupancy of molecules of interest between 20% and 25% of reaction chambers in an array, between 25% and 30%, between 30% and 35%, between 35% and 37%, between 37% and 40%, between 40% and 45%, between 45% and 50%, between 50% and 60%, between 60% and 70%, between 70% and 80%, between 80% and 90%, between 90% and 95%, between 95% and 99%, or between 95% and 100% of reaction chambers in an array. In some cases, the occupancy may be within 10% of the end values in one or more of these ranges.

Devices and methods described herein may allow for loading molecules of interest into reaction chambers of extremely small volumes. For example, in some embodiments, the capacity of a sample reservoir (e.g., a recessed region 2-905) in an integrated device and all reaction chambers therein is approximately $20 \times 10^{-6}$ L, with each reaction chamber having a volume of approximately $3 \times 10^{-18}$ L. In some embodiments, an integrated device contains 512,000 reaction chambers. Accordingly, in some embodiments, the total volume of all reaction chambers accounts for approximately 0.00000768% of the capacity for a suspension.

A. Crowding Agents

In some embodiments, a crowding agent may effectively exclude samples of interest (e.g., sequencing templates) from bulk solvent of a suspension. The inclusion of a crowding agent may produce a volume exclusion effect that excludes molecules of interest from the bulk volume of a suspension, which can assist in driving the molecules of interest towards and/or into reaction chambers. As a result, a greater percentage of reaction chambers are capable of receiving a successfully loaded molecule of interest. Thus, in some embodiments, crowding agents may produce a thermodynamic driving force that effectively increases the concentration of the molecule of interest at the surface of an integrated device. In some embodiments, crowding agents may decrease loading time by having a kinetic effect that accelerates the movement of the molecules of interest into the reaction chambers.

As used herein, a "crowding agent" is any compound or molecule that allows for, enhances, or facilitates sample crowding. Without wishing to be bound by any particular mechanism, it is suggested that crowding agents reduce the volume of solvent that is available for samples or other macromolecules. This excluded volume effect limits the volume accessible to samples or macromolecules as a result of non-specific interactions, such as steric repulsion, with the crowding agent. Accordingly, in some embodiments, a crowding agent may be referred to as a "volume excluder" or "volume excluding agent." In some embodiments, the crowding agent is inert with respect to other components in the same suspension. In some embodiments, the crowding agent does not interfere with reactions occurring in the same suspension.

It should be appreciated that different types of crowding agents that create a volume exclusion effect may be used as part of the sample loading techniques described herein. Some types of crowding agents may attract water, allowing molecules other than water to aggregate and/or become concentrated at a particular location, such as at a surface of an integrated device. In some instances, the crowding agent binds to and/or ties up water in a suspension to exclude a sample or macromolecule in the suspension. Another type of crowding agent may act to compact a volume of a molecule of interest, such as a sequencing template, in a suspension. Such crowding agents may allow larger sequencing templates to be loaded into the reaction chamber because the overall volume of the sequencing template is reduced. Other types of crowding agent may promote phase separation and/or exert osmotic pressure.

Including one or more crowding agents as part of a sample loading process may facilitate loading of molecules of interest into reaction chambers, including facilitating loading of molecules over longer distances and more faster than if no crowding agents were used. In this manner, a crowding agent may decrease the time required to incubate a suspension on an integrated device comprising reaction chambers before single molecule analysis, for example, of samples using the device can be performed. In some implementations, a particular crowding agent may be selected such that it stays (e.g., preferentially) in a sample reservoir as opposed to migrating into reaction chambers. In some embodiments, this promotes a thermodynamic driving force that drives the loading of samples (e.g., DNA-polymerase complex) into the reaction chambers. In some embodiments, lower viscosity crowding agents such as Ficoll or polyvinylpyrrolidone have high mobility and poor localization relative to higher viscosity agents and are not as effective as the higher viscosity agents. However, it should be appreciated that lower viscosity agents may be useful in some contexts.

In some embodiments, the crowding agent is a polysaccharide. In some embodiments, the crowding agent is a cellulose molecule. In some embodiments, the crowding agent is methyl cellulose. In some embodiments, the crowding agent is a cellulose molecule selected from the group consisting of ethyl cellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, carboxymethyl cellulose, and derivatives and combinations thereof. In some embodiments, the crowding agent is a Ficoll polymer. In some embodiments, a crowding agent, such as a cellulose crowding agent (e.g., Methocel MC of 63,000), has an average molecular weight of 50,000 to 500,000 Da (e.g., from 50 kDa to 100 kDa in some embodiments, from 100 kDa to 200 kDa in some embodiments, from 200 kDa to 300 kDa in some embodiments, from 300 kDa to 400 kDa in some embodiments, and yet from 400 t kDa to 500 kDa in some embodiments). In some cases, a crowding agent may have an average molecular weight greater than 500 kDa.

In some embodiments, the crowding agent is provided in a suspension to which samples for analysis may be or have been added. In some embodiments, concentration of the crowding agent in the suspension is between 0.6% and 0.9% by weight or equal to either of the end values. In some embodiments, concentration of the crowding agent in the suspension is between 0.9% and 1.8% by weight or equal to either of the end values. In some embodiments, concentration of the crowding agent in the suspension is between 1.8% and 2.0% by weight or equal to either of the end values. In some embodiments, concentration of the crowding agent in the suspension is between 2.0% and 2.3% by weight or equal to either of the end values. In some embodiments, concentration of the crowding agent in the suspension is about 2.3% by weight. In some embodiments, the crowding agent is present in the suspension between 0.1% by weight to 1.0% by weight, between 1.0% by weight to 5.0% by weight in some cases, between 5.0% by weight to 10.0% by weight in some cases, and yet between 10.0% by weight to 20.0% by weight in some cases. In some implementations, the concentration of the crowding agent in the suspension may have a greater value than 20% by weight. In some cases, the concentration of the crowding agent is within 10% of the expressed ranges or values above.

In some embodiments, a crowding agent is provided in the form of a gel (e.g., a hydrophilic gel) that can be placed in direct contact with a suspension (e.g., in a sample reservoir). Gels can be applied (e.g., in the form of a gel plug) without being limited by pipetting considerations and higher concentrations and viscosities of crowding agent can be used in the form of a gel. In some embodiments, the crowding agent is provided in a solid state. For example, in some embodiments, the crowding agent is provided as a film, a fibrous material, a membranous material, an adhesive material, a composite material, a laminate material, or some combination thereof.

B. Condensing Agents

As used herein, "condensing agent" refers to any natural or synthetic compound, which when combined with a sample of interest causes the sample of interest (e.g., a molecule or macromolecule) to assume a condensed structure relative to its structure in absence of the condensing agent. For example, in a given suspension, the sample of interest occupies a smaller volume in the presence of the condensing agent than the same suspension lacking the condensing agent. In this manner, a condensing agent may act to reduce the occupancy volume of the sample of interest (e.g., a molecule) in the suspension. In the context of a molecule in a suspension, a condensing agent may act to reduce the pervaded volume of the molecule of interest in the suspension. The condensing agent may interact with the molecule of interest such that the molecule adopts a compacted structure that occupies a smaller fraction of the total volume in a suspension.

In some embodiments, the condensing agent is a nucleic acid condensing agent. Nucleic acid condensing agents can compact nucleic acids by a variety of mechanisms, including, but not limited to, volume exclusion and charge screening. Assays to evaluate the capability of an agent to condense nucleic acids are known in the art, e.g., as described in WO/1996/021036, the relevant content of which is incorporated herein by reference in its entirety. In some embodiments, a nucleic acid condensing agent interacts with nucleic acids via electrostatic charge-charge interactions to induce a collapsing of the nucleic acid structure (e.g., nucleic acid condensation). In some embodiments, a condensing agent can condense a nucleic acid as a result of one or more of the following: exerting osmotic pressure to bring segments of the helical structure together (e.g., molecular crowding effect), decreasing repulsive interactions between nucleic acid segments (e.g., by neutralizing phosphate charge), and increasing attractive interactions between nucleic acid segments. In some embodiments, attractive interactions between the DNA segments can be induced by multivalent cationic charged condensing agents.

In some embodiments, a condensing agent comprises a polycation. As used herein, a polycation refers generally to a compound having a plurality of positively charged sites. In some embodiments, the polycation is polycationic when present in a suspension that includes a molecule of interest. For example, in some embodiments, conditions (e.g., pH, buffer capacity, ionic strength) in a suspension comprising a molecule of interest are such that the condensing agent is polycationic in the suspension. In some embodiments, the polycation is polycationic at physiological pH (e.g., pH≈7.4). In some embodiments, the polycation is a polymer of positively charged monomeric units, although some non-positively charged units may be present in the polymer. Examples of polycations include, in some embodiments, polyamines, such as spermine, spermidine, and putrescine. In some embodiments, the polycation comprises a polyamino acid, such as polyhistidine, polylysine, polyarginine, and polyornithine. Other basic peptides and small basic proteins are further contemplated for use as polycationic condensing agents (e.g., histones, protamines). For polycations composed of amino acids, either the L- or D-forms may be used. Basic amino acids include lysine, arginine, amino acid analogues such as ornithine and canaline, modified basic amino acids, such as homoarginine, and other modified amino acids modified to carry a positive charge, such as guanidinovalinate, and aminoethylcysteine. Additional examples of polycations include polyammoniums (e.g., Polybrene (hexadimethrine bromide)), lipids (e.g., DOTAP, DC-Chol/DOPE, DOGS/DOPE, and DOTMA/DOPE).

C. Loading Suspensions on Integrated Devices

In some aspects, the present application provides devices and methods useful for loading a suspension comprising at least one sample of interest onto a surface of an integrated device 1-102 that includes reaction chambers 1-108. Suspension loading may be conducted by any number of suitable methods. In some embodiments, the suspension containing molecules of interest, for example, is loaded by a practitioner, e.g., via a pipette, a dispenser, or any suitable fluid transfer device/system. In some embodiments, the suspension is loaded by automated means (e.g., a robotic device/system). In some embodiments, the suspension is loaded via one or more microfluidic channels.

In some embodiments, a sample of interest can be delivered to an integrated device (e.g., an integrated device comprising reaction chambers, an array) by methods that are generally used to deliver samples to an integrated device. For example, delivery methods can include suspending the sample of interest in a fluid and flowing the resulting suspension to the reaction chambers of the integrated device. This can include simply pipetting the relevant suspension onto one or more regions of the integrated device, or this can include more active flow methods, such as electro-direction or pressure-based fluid flow. In some embodiments, a suspension comprising a sample of interest is flowed into selected regions of the integrated device, e.g., where a particular molecule of interest is to be analyzed in a particular region of the integrated device. This can be accomplished by masking techniques (applying a mask to direct fluid flow), microfluidics, or by active flow methods such as electro-direction or pressure based fluid flow, including by ink-jet printing methods. In some embodiments, microfluidic flow in patterned microfluidic channels can be used for delivery of samples in suspension to reaction chambers. Regions of an integrated device can also be selective targets of delivery simply by pipetting the relevant suspension into the correct region of the integrated device.

It should be appreciated that, in some embodiments, compositions used in sample loading described herein may be introduced to a surface of an integrated device in any suitable order. For example, in some embodiments, a suspension containing samples is contacted to the surface prior to being contacted with the crowding agent and/or condensing agent. In some embodiments, the suspension may be contacted to the surface and allowed to incubate for an incubation period prior to being contacted with the crowding agent and/or condensing agent. In some embodiments, a condensing agent is present in the suspension during such an incubation period. In some embodiments, the crowding agent and/or condensing agent is introduced on the surface immediately or approximately soon after the suspension has been introduced. In some embodiments, the suspension comprises the crowding agent and/or condensing agent prior to being introduced to the surface.

D. Example Samples

Some examples of samples of interest relating to sequencing are described in this section, though the invention is not limited to only the described exemplary samples. The described apparatus and sample loading techniques may be applied to proteins, sub-micron-scale particles, biologic and non-biologic molecules. As used herein, a "sequencing template" is an example of a sample of interest and is a molecule that is the subject of an analysis (e.g., a sequencing analysis). In some embodiments, the sequencing template comprises a nucleic acid molecule. In some embodiments, the nucleic acid molecule is referred to as a "target" or "template" nucleic acid. The nucleic acid molecule may be between 1 kb and 10 kb in some embodiments, between 10 kb and 25 kb in some embodiments, between 25 kb and 50 kb in some embodiments, between 50 kb and 100 kb in some embodiments, between 100 kb and 250 kb in some embodiments, between 250 kb and 500 kb in some embodiments, or between 500 kb and 1000 kb in some embodiments. In some cases, nucleic acid molecule may have a length that is within 10% of the end values in these ranges.

In some embodiments, the nucleic acid molecule comprises at least one hybridized primer/polymerizing enzyme complex. For example, in some embodiments, the nucleic acid molecule is contacted with a sequencing primer that is complementary to a portion of the nucleic acid molecule such that the sequencing primer anneals to the nucleic acid molecule. This priming location generates a site at which a polymerizing enzyme (e.g., a DNA or RNA polymerase) may couple to the nucleic acid molecule to form a hybridized primer/polymerizing enzyme complex. Accordingly, in some embodiments, a sequencing template comprising at least one hybridized primer/polymerizing enzyme may be referred to as a "sequencing template complex."

The term "nucleic acid," as used herein, generally refers to a molecule comprising one or more nucleic acid subunits. A nucleic acid may include one or more subunits selected from adenine (A), cytosine (C), guanine (G), thymine (T), and uracil (U), or variants thereof. In some examples, a nucleic acid is deoxyribonucleic acid (DNA) or ribonucleic acid (RNA), or derivatives thereof. In some embodiments, the nucleic acid is a modified nucleic acid, including, without limitation, a locked nucleic acid (LNA), a peptide nucleic acid (PNA), a triazole-linked nucleic acid, a 2'-F-modified nucleic acid, and derivatives and analogs thereof. A nucleic acid may be single-stranded or double-stranded. In some embodiments, a nucleic acid generally refers to any polymer of nucleotides.

A nucleotide (e.g., a nucleoside polyphosphate) can comprise any of an adenine (A), cytosine (C), guanine (G), thymine (T), and uracil (U), or variants thereof. A nucleotide (e.g., a nucleoside polyphosphate) can comprise a methylated nucleobase. For example, a methylated nucleotide can be a nucleotide that comprises one or more methyl groups attached to the nucleobase (e.g., attached directly to a ring of the nucleobase, attached to a substituent of a ring of the nucleobase). Exemplary methylated nucleobases include 1-methylthymine, 1-methyluracil, 3-methyluracil, 3-methylcytosine, 5-methylcytosine, 1-methyladenine, 2-methyladenine, 7-methyladenine, N6-methyladenine, N6,N6-dimethyladenine, 1-methylguanine, 7-methylguanine, N2-methylguanine, and N2,N2-dimethylguanine.

The term "primer," as used herein, generally refers to a nucleic acid molecule (e.g., an oligonucleotide), which can include a sequence comprising A, C, G, T, and/or U, or variants or analogs thereof. A primer can be a synthetic oligonucleotide comprising DNA, RNA, PNA, or variants or analogs thereof. A primer can be designed such that its nucleotide sequence is complementary to a target or template nucleic acid, or the primer can comprise a random nucleotide sequence. In some embodiments, a primer can comprise a tail (e.g., a poly-A tail, an index adaptor, a molecular barcode, etc.). In some embodiments, a primer can comprise 5 to 15 bases, 10 to 20 bases, 15 to 25 bases, 20 to 30 bases, 25 to 35 bases, 30 to 40 bases, 35 to 45 bases, 40 to 50 bases, 45 to 55 bases, 50 to 60 bases, 55 to 65 bases, 60 to 70 bases, 65 to 75 bases, 70 to 80 bases, 75 to 85 bases, 80 to 90 bases, 85 to 95 bases, 90 to 100 bases, 95 to 105 bases, 100 to 150 bases, 125 to 175 bases, 150 to 200 bases, or more than 200 bases.

As described in the present application, sequencing can include the determination of individual subunits of a template biomolecule (e.g., nucleic acid molecule) by synthesizing another biomolecule that is complementary or analogous to the template, such as by synthesizing a nucleic acid molecule that is complementary to a template nucleic acid molecule and identifying the incorporation of nucleotides with time (e.g., sequencing by synthesis). As an alternative, sequencing can include the direct identification of individual subunits of the biomolecule.

IV. Additional Aspects of the System

An analytic system described herein may include an integrated device and an instrument configured to interface with the integrated device. The integrated device may include an array of pixels, where a pixel includes a reaction chamber and at least one photodetector. A surface of the integrated device may have a plurality of reaction chambers, where a reaction chamber is configured to receive a sample from a suspension placed on the surface of the integrated device. A suspension may contain multiple samples of a same type, and in some embodiments, different types of samples. In this regard, the phrase "sample of interest" as used herein can refer to a plurality of samples of a same type that are dispersed in a suspension, for example. Similarly, the phrase "molecule of interest" as used herein can refer to a plurality of molecules of a same type that are dispersed in a suspension. The plurality of reaction chambers may have a suitable size and shape such that at least a portion of the reaction chambers receive one sample from a suspension. In some embodiments, the number of samples within a reaction chamber may be distributed among the reaction chambers such that some reaction chambers contain one sample with others contain zero, two or more samples.

In some embodiments, a suspension may contain multiple single-stranded DNA templates, and individual reaction chambers on a surface of an integrated device may be sized and shaped to receive a sequencing template. Sequencing templates may be distributed among the reaction chambers of the integrated device such that at least a portion of the reaction chambers of the integrated device contain a sequencing template. The suspension may also contain labeled nucleotides which then enter in the reaction chamber and may allow for identification of a nucleotide as it is incorporated into a strand of DNA complementary to the single-stranded DNA template in the reaction chamber. In some embodiments, the suspension may contain sequencing templates and labeled nucleotides may be subsequently introduced to a reaction chamber as nucleotides are incorporated into a complementary strand within the reaction chamber. In this manner, timing of incorporation of nucleotides may be controlled by when labeled nucleotides are introduced to the reaction chambers of an integrated device.

Excitation light is provided from an excitation source located separate from the pixel array of the integrated device. The excitation light is directed at least in part by elements of the integrated device towards one or more pixels to illuminate an illumination region within the reaction chamber. A marker may then emit emission light when located within the illumination region and in response to being illuminated by excitation light. In some embodiments, one or more excitation sources are part of the instrument and the system where components of the instrument and the integrated device are configured to direct the excitation light towards one or more pixels.

Emission light emitted from a reaction chamber (e.g., by a fluorescent label) may then be detected by one or more photodetectors within a pixel of the integrated device. Characteristics of the detected emission light may provide an indication for identifying the marker associated with the emission light. Such characteristics may include any suitable type of characteristic, including an arrival time of photons detected by a photodetector, an amount of photons accumulated over time by a photodetector, and/or a distribution of photons across two or more photodetectors. In some embodiments, a photodetector may have a configuration that allows for the detection of one or more timing characteristics associated with emission light (e.g., fluorescence lifetime). The photodetector may detect a distribution of photon arrival times after a pulse of excitation light propagates through the integrated device, and the distribution of arrival times may provide an indication of a timing characteristic of the emission light (e.g., a proxy for fluorescence lifetime). In some embodiments, the one or more photodetectors provide an indication of the probability of emission light emitted by the marker (e.g., fluorescence intensity). In some embodiments, a plurality of photodetectors may be sized and arranged to capture a spatial distribution of the emission light. Output signals from the one or more photodetectors may then be used to distinguish a marker from among a plurality of markers, where the plurality of markers may be used to identify a sample or its structure. In some embodiments, a sample may be excited by multiple excitation energies, and emission light and/or timing characteristics of the emission light from the reaction chamber in response to the multiple excitation energies may distinguish a marker from a plurality of markers.

Figures 2, 3, 4, 5:
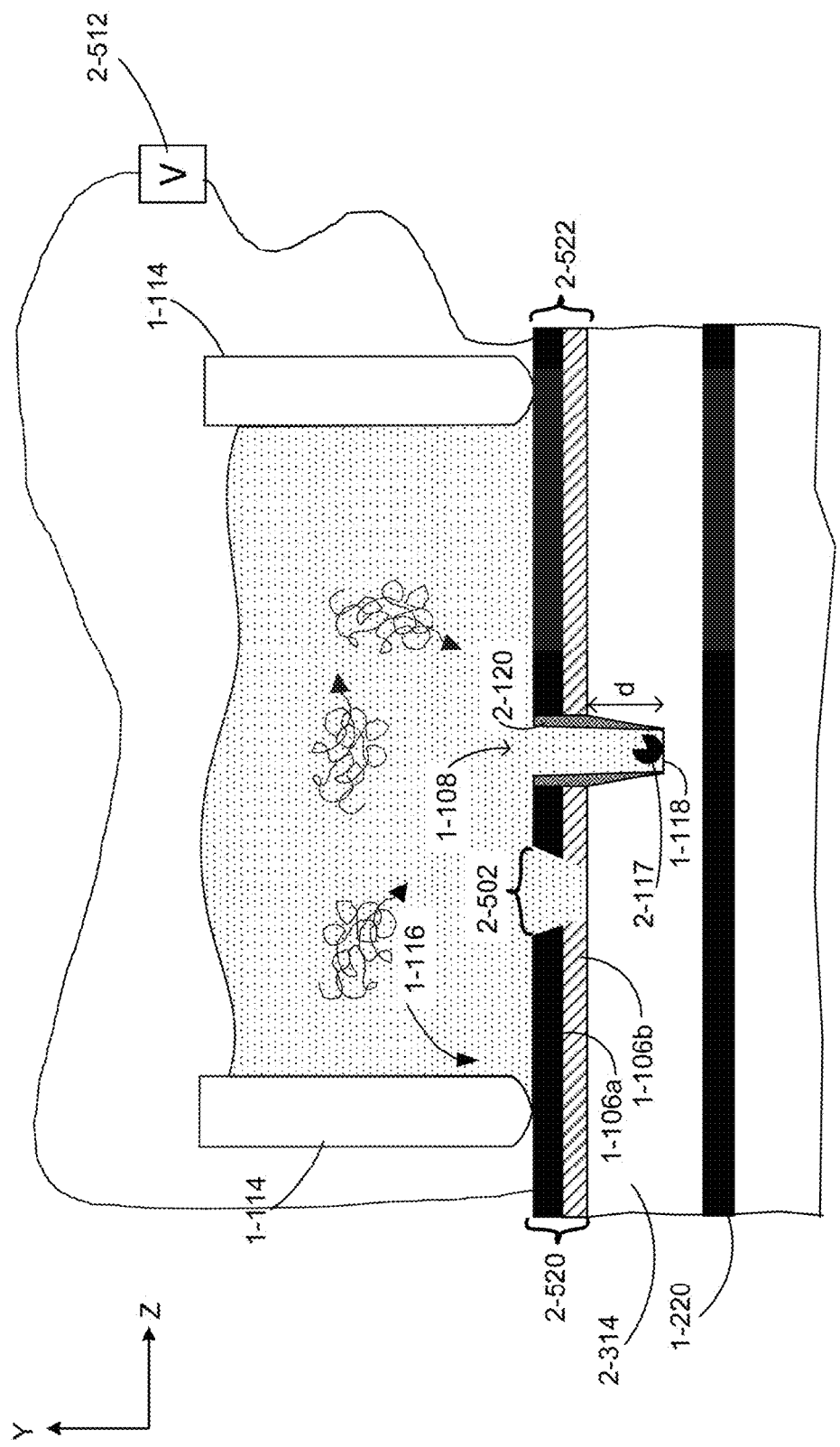

A schematic overview of the system 5-100 is illustrated in FIG. 5-1A. The system comprises both an integrated device 5-102 that interfaces with an instrument 5-104. In some embodiments, instrument 5-104 may include one or more excitation sources 5-106 integrated as part of instrument 5-104. In some embodiments, an excitation source may be external to both instrument 5-104 and integrated device 5-102, and instrument 5-104 may be configured to receive excitation light from the excitation source and direct excitation light to the integrated device. The integrated device may interface with the instrument using any suitable socket for receiving the integrated device and holding it in precise optical alignment with the excitation source. The excitation source 5-106 may be configured to provide excitation light to the integrated device 5-102. As illustrated schematically in FIG. 5-1A, the integrated device 5-102 has a plurality of pixels 5-112, where at least a portion of pixels may perform independent analysis of a sample of interest. Such pixels 5-112 may be referred to as "passive source pixels" since a pixel receives excitation light from a source 5-106 separate from the pixel, where excitation light from the source excites some or all of the pixels 5-112. Excitation source 5-106 may be any suitable light source. Examples of suitable excitation sources are described in U.S. patent application Ser. No. 14/821,688, filed Aug. 7, 2015, titled "INTEGRATED DEVICE FOR PROBING, DETECTING AND ANALYZING MOLECULES," which is incorporated by reference in its entirety. In some embodiments, excitation source 5-106 includes multiple excitation sources that are combined to deliver excitation light to integrated device 5-102. The multiple excitation sources may be configured to produce multiple excitation energies or wavelengths.

A pixel 5-112 has a reaction chamber 5-108 configured to receive a single sample of interest and a photodetector 5-110 for detecting emission light emitted from the reaction chamber in response to illuminating the sample and at least a portion of the reaction chamber 5-108 with excitation light provided by the excitation source 5-106. In some embodiments, reaction chamber 5-108 may retain the sample in proximity to a surface of integrated device 5-102, which may ease delivery of excitation light to the sample and detection of emission light from the sample or a reaction component (e.g., a labeled nucleotide).

Optical elements for coupling excitation light from excitation light source 5-106 to integrated device 5-102 and guiding excitation light to the reaction chamber 5-108 are located both on integrated device 5-102 and the instrument 5-104. Source-to-chamber optical elements may comprise one or more grating couplers located on integrated device 5-102 to couple excitation light to the integrated device and waveguides to deliver excitation light from instrument 5-104 to reaction chambers in pixels 5-112. One or more optical splitter elements may be positioned between a grating coupler and the waveguides. The optical splitter may couple excitation light from the grating coupler and deliver excitation light to at least one of the waveguides. In some embodiments, the optical splitter may have a configuration that allows for delivery of excitation light to be substantially uniform across all the waveguides such that each of the waveguides receives a substantially similar amount of excitation light. Such embodiments may improve performance of the integrated device by improving the uniformity of excitation light received by reaction chambers of the integrated device.

Reaction chamber 5-108, a portion of the excitation source-to-chamber optics, and the reaction chamber-to-photodetector optics are located on integrated device 5-102. Excitation source 5-106 and a portion of the source-to-chamber components are located in instrument 5-104. In some embodiments, a single component may play a role in both coupling excitation light to reaction chamber 5-108 and delivering emission light from reaction chamber 5-108 to photodetector 5-110. Examples of suitable components, for coupling excitation light to a reaction chamber and/or directing emission light to a photodetector, to include in an integrated device are described in U.S. patent application Ser. No. 14/821,688, filed Aug. 7, 2015, titled "INTEGRATED DEVICE FOR PROBING, DETECTING AND ANALYZING MOLECULES," and U.S. patent application Ser. No. 14/543,865, filed Nov. 17, 2014, titled "INTEGRATED DEVICE WITH EXTERNAL LIGHT SOURCE FOR PROBING, DETECTING, AND ANALYZING MOLECULES," both of which are incorporated by reference in their entirety.

Pixel 5-112 is associated with its own individual reaction chamber 5-108 and at least one photodetector 5-110. The plurality of pixels of integrated device 5-102 may be arranged to have any suitable shape, size, and/or dimensions. Integrated device 5-102 may have any suitable number of pixels. The number of pixels in integrated device 2-102 may be in the range of approximately 10,000 pixels to 1,000,000 pixels or any value or range of values within that range. In some embodiments, the pixels may be arranged in an array of 512 pixels by 512 pixels. Integrated device 5-102 may interface with instrument 5-104 in any suitable manner. In some embodiments, instrument 5-104 may have an interface that detachably couples to integrated device 5-102 such that a user may attach integrated device 5-102 to instrument 5-104 for use of integrated device 5-102 to analyze at least one sample of interest in a suspension and remove integrated device 5-102 from instrument 5-104 to allow for another integrated device to be attached. The interface of instrument 5-104 may position integrated device 5-102 to couple with circuitry of instrument 5-104 to allow for readout signals from one or more photodetectors to be transmitted to instrument 5-104. Integrated device 5-102 and instrument 5-104 may include multi-channel, high-speed communication links for handling data associated with large pixel arrays (e.g., more than 10,000 pixels).

A cross-sectional schematic of integrated device 5-102 illustrating a row of pixels 5-112 is shown in FIG. 5-1B. Integrated device 5-102 may include coupling region 5-201, routing region 5-202, and pixel region 5-203. Pixel region 5-203 may include a plurality of pixels 5-112 having reaction chambers 5-108 positioned on a surface at a location separate from coupling region 5-201, which is where excitation light (shown as the dashed arrow) couples to integrated device 5-102. Reaction chambers 5-108 may be formed through metal layer(s) 5-116. One pixel 5-112, illustrated by the dotted rectangle, is a region of integrated device 5-102 that includes a reaction chamber 5-108 and photodetector region having one or more photodetectors 5-110.

FIG. 5-1B illustrates the path of excitation (shown in dashed lines) by coupling a beam of excitation light to coupling region 5-201 and to reaction chambers 5-108. The row of reaction chambers 5-108 shown in FIG. 5-1B may be positioned to optically couple with waveguide 5-220. Excitation light may illuminate a sample located within a reaction chamber. The sample or a reaction component (e.g., fluorescent label) may reach an excited state in response to being illuminated by the excitation light. When in an excited state, the sample or reaction component may emit emission light, which may be detected by one or more photodetectors associated with the reaction chamber. FIG. 5-1B schematically illustrates the path of emission light (shown as the solid line) from a reaction chamber 5-108 to photodetector(s) 5-110 of pixel 5-112. The photodetector(s) 5-110 of pixel 5-112 may be configured and positioned to detect emission light from reaction chamber 5-108. Examples of suitable photodetectors are described in U.S. patent application Ser. No. 14/821,656, filed Aug. 7, 2015, titled "INTEGRATED DEVICE FOR TEMPORAL BINNING OF RECEIVED PHOTONS," which is incorporated by reference in its entirety. For an individual pixel 5-112, a reaction chamber 5-108 and its respective photodetector(s) 5-110 may be aligned along a common axis (along the y-direction shown in FIG. 5-1B). In this manner, the photodetector(s) may overlap with the reaction chamber within a pixel 5-112.

The directionality of the emission light from a reaction chamber 5-108 may depend on the positioning of the sample in the reaction chamber 5-108 relative to metal layer(s) 5-116 because metal layer(s) 5-116 may act to reflect emission light. In this manner, a distance between metal layer(s) 5-116 and a fluorescent marker positioned in a reaction chamber 5-108 may impact the efficiency of photodetector(s) 5-110, that are in the same pixel as the reaction chamber, to detect the light emitted by the fluorescent marker. The distance between metal layer(s) 5-116 and the bottom surface of a reaction chamber 5-106, which is proximate to where a sample may be positioned during operation, may be in the range of 100 nm to 500 nm, or any value or range of values in that range. In some embodiments the distance between metal layer(s) 5-116 and the bottom surface of a reaction chamber 5-108 is approximately 300 nm.

The distance between the sample and the photodetector(s) may also impact efficiency in detecting emission light. By decreasing the distance light has to travel between the sample and the photodetector(s), detection efficiency of emission light may be improved. In addition, smaller distances between the sample and the photodetector(s) may allow for pixels that occupy a smaller area footprint of the integrated device, which can allow for a higher number of pixels to be included in the integrated device. The distance between the bottom surface of a reaction chamber 5-108 and photodetector(s) may be in the range of 1 µm to 15 µm, or any value or range of values in that range.

Photonic structure(s) 5-230 may be positioned between reaction chambers 5-108 and photodetectors 5-110 and configured to reduce or prevent excitation light from reaching photodetectors 5-110, which may otherwise contribute to signal noise in detecting emission light. As shown in FIG. 5-1B, the one or more photonic structures 5-230 may be positioned between waveguide 5-220 and photodetectors 5-110. Photonic structure(s) 5-230 may include one or more optical rejection photonic structures including a spectral filter, a polarization filter, and a spatial filter. Photonic structure(s) 5-230 may be positioned to align with individual reaction chambers 5-108 and their respective photodetector(s) 5-110 along a common axis. Metal layers 5-240, which may act as a circuitry for integrated device 5-102, may also act as a spatial filter, in accordance with some embodiments. In such embodiments, one or more metal layers 5-240 may be positioned to block some or all excitation light from reaching photodetector(s) 5-110.

Coupling region 5-201 may include one or more optical components configured to couple excitation light from an external excitation source. Coupling region 5-201 may include grating coupler 5-216 positioned to receive some or all of a beam of excitation light. Examples of suitable grating couplers are described in U.S. patent application Ser. No. 15/844,403, filed Dec. 15, 2017, titled "OPTICAL COUPLER AND WAVEGUIDE SYSTEM," which is incorporated by reference in its entirety. Grating coupler 5-216 may couple excitation light to waveguide 5-220, which may be configured to propagate excitation light to the proximity of one or more reaction chambers 5-108. Alternatively, coupling region 5-201 may comprise other well-known structures for coupling light into a waveguide.

Components located off of the integrated device may be used to position and align the excitation source 5-106 to the integrated device. Such components may include optical components including lenses, mirrors, prisms, windows, apertures, attenuators, and/or optical fibers. Additional mechanical components may be included in the instrument to allow for control of one or more alignment components. Such mechanical components may include actuators, stepper motors, and/or knobs. Examples of suitable excitation sources and alignment mechanisms are described in U.S. patent application Ser. No. 15/161,088, filed May 20, 2016, titled "PULSED LASER AND SYSTEM," which is incorporated by reference in its entirety. Another example of a beam-steering module is described in U.S. patent application Ser. No. 15/842,720, filed Dec. 14, 2017, titled "COMPACT BEAM SHAPING AND STEERING ASSEMBLY," which is incorporated herein by reference.

A sample to be analyzed may be introduced into reaction chamber 5-108 of pixel 5-112. The sample may be a biological sample or any other suitable sample, such as a chemical sample. In some cases, the suspension may include multiple molecules of interest and the reaction chamber may be configured to isolate a single molecule. In some instances, the dimensions of the reaction chamber may act to confine a single molecule within the reaction chamber, allowing measurements to be performed on the single molecule. Excitation light may be delivered into the reaction chamber 5-108, so as to excite the sample or at least one fluorescent marker attached to the sample or otherwise associated with the sample while it is within an illumination area within the reaction chamber 5-108.

In operation, parallel analyses of samples within the reaction chambers are carried out by exciting some or all of the samples within the reaction chambers using excitation light and detecting signals with the photodetectors that are representative of emission light from the reaction chambers. Emission light from a sample or reaction component (e.g., fluorescent label) may be detected by a corresponding photodetector and converted to at least one electrical signal. The electrical signals may be transmitted along conducting lines (e.g., metal layers 5-240) in the circuitry of the integrated device, which may be connected to an instrument interfaced with the integrated device. The electrical signals may be subsequently processed and/or analyzed. Processing or analyzing of electrical signals may occur on a suitable computing device either located on or off the instrument.

Instrument 5-104 may include a user interface for controlling operation of instrument 5-104 and/or integrated device 5-102. The user interface may be configured to allow a user to input information into the instrument, such as commands and/or settings used to control the functioning of the instrument. In some embodiments, the user interface may include buttons, switches, dials, and a microphone for voice commands. The user interface may allow a user to receive feedback on the performance of the instrument and/or integrated device, such as proper alignment and/or information obtained by readout signals from the photodetectors on the integrated device. In some embodiments, the user interface may provide feedback using a speaker to provide audible feedback. In some embodiments, the user interface may include indicator lights and/or a display screen for providing visual feedback to a user.

In some embodiments, instrument 5-104 may include a computer interface configured to connect with a computing device. Computer interface may be a USB interface, a FireWire interface, or any other suitable computer interface. Computing device may be any general purpose computer, such as a laptop or desktop computer. In some embodiments, computing device may be a server (e.g., cloud-based server) accessible over a wireless network via a suitable computer interface. The computer interface may facilitate communication of information between instrument 5-104 and the computing device. Input information for controlling and/or configuring the instrument 5-104 may be provided to the computing device and transmitted to instrument 5-104 via the computer interface. Output information generated by instrument 5-104 may be received by the computing device via the computer interface. Output information may include feedback about performance of instrument 5-104, performance of integrated device 5-112, and/or data generated from the readout signals of photodetector 5-110.

In some embodiments, instrument 5-104 may include a processing device configured to analyze data received from one or more photodetectors of integrated device 5-102 and/or transmit control signals to excitation source(s) 2-106. In some embodiments, the processing device may comprise a general purpose processor, a specially-adapted processor (e.g., a central processing unit (CPU) such as one or more microprocessor or microcontroller cores, a field-programmable gate array (FPGA), an application-specific integrated circuit (ASIC), a custom integrated circuit, a digital signal processor (DSP), or a combination thereof.) In some embodiments, the processing of data from one or more photodetectors may be performed by both a processing device of instrument 5-104 and an external computing device. In other embodiments, an external computing device may be omitted and processing of data from one or more photodetectors may be performed solely by a processing device of integrated device 5-102.

A non-limiting example of a biological reaction taking place in a reaction chamber 5-330 is depicted in FIG. 5-2. In this example, sequential incorporation of nucleotides and/or nucleotide analogs into a growing strand that is complementary to a target nucleic acid is taking place in the reaction chamber. The sequential incorporation can be detected to sequence a series of nucleic acids (e.g., DNA, RNA). The reaction chamber may have a depth in the range of approximately 100 to approximately 500 nm, or any value or range of values within that range, and a diameter in the range of approximately 80 nm to approximately 200 nm. A metallization layer 5-540 (e.g., a metallization for an electrical reference potential) may be patterned above the photodetector to provide an aperture that blocks stray light from adjacent reaction chambers and other unwanted light sources. According to some embodiments, polymerase 5-520 may be located within the reaction chamber 5-330 (e.g., attached to a base of the reaction chamber). The polymerase may take up a target nucleic acid 5-510 (e.g., a portion of nucleic acid derived from DNA), and sequence a growing strand of complementary nucleic acid to produce a growing strand of DNA 5-512. Nucleotides and/or nucleotide analogs labeled with different fluorophores may be dispersed in a suspension above and within the reaction chamber.

When a labeled nucleotide and/or nucleotide analog 5-610 is incorporated into a growing strand of complementary nucleic acid, as depicted in FIG. 5-3, one or more attached fluorophores 5-630 may be repeatedly excited by pulses of optical energy coupled into the reaction chamber 5-330 from the waveguide 5-315. In some embodiments, the fluorophore or fluorophores 5-630 may be attached to one or more nucleotides and/or nucleotide analogs 5-610 with any suitable linker 5-620. An incorporation event may last for a period of time up to about 100 ms. During this time, pulses of fluorescent emission resulting from excitation of the fluorophore(s) by pulses from the mode-locked laser may be detected with a time-binning photodetector 5-322. By attaching fluorophores with different emission characteristics (e.g., fluorescent decay rates, intensity, fluorescent wavelength) to the different nucleotides (A,C,G,T), detecting and distinguishing the different emission characteristics while the strand of DNA 5-512 incorporates a nucleic acid and enables determination of the nucleotide sequence of the growing strand of DNA.

According to some embodiments, an instrument 5-104 that is configured to analyze samples based on fluorescent emission characteristics may detect differences in fluorescent lifetimes and/or intensities between different fluorescent molecules, and/or differences between lifetimes and/or intensities of the same fluorescent molecules in different environments. By way of explanation, FIG. 5-4 plots two different fluorescent emission probability curves (A and B), which may be representative of fluorescent emission from two different fluorescent molecules, for example. With reference to curve A (dashed line), after being excited by a short or ultrashort optical pulse, a probability $p_A(t)$ of a fluorescent emission from a first molecule may decay with time, as depicted. In some cases, the decrease in the probability of a photon being emitted over time may be represented by an exponential decay function $p_A(t)=P_{Ao}e^{-t/\tau_A}$, where $P_{Ao}$ is an initial emission probability and $\tau_A$ is a temporal parameter associated with the first fluorescent molecule that characterizes the emission decay probability. TA may be referred to as the "fluorescence lifetime," "emission lifetime," or "lifetime" of the first fluorescent molecule. In some cases, the value of $\tau_A$ may be altered by a local environment of the fluorescent molecule. Other fluorescent molecules may have different emission characteristics than that shown in curve A. For example, another fluorescent molecule may have a decay profile that differs from a single exponential decay, and its lifetime may be characterized by a half-life value or some other metric.

A second fluorescent molecule may have a decay profile that is exponential, but has a measurably different lifetime $\tau_B$, as depicted for curve B in FIG. 5-4. In the example shown, the lifetime for the second fluorescent molecule of curve B is shorter than the lifetime for curve A, and the probability of emission is higher sooner after excitation of the second molecule than for curve A. Different fluorescent molecules may have lifetimes or half-life values ranging from about 0.1 ns to about 20 ns, in some embodiments.

The inventors have recognized and appreciated that differences in fluorescent emission lifetimes can be used to discern between the presence or absence of different fluorescent molecules and/or to discern between different environments or conditions to which a fluorescent molecule is subjected. In some cases, discerning fluorescent molecules based on lifetime (rather than emission wavelength, for example) can simplify aspects of an instrument 5-104. As an example, wavelength-discriminating optics (such as wavelength filters, dedicated detectors for each wavelength, dedicated pulsed optical sources at different wavelengths, and/or diffractive optics) may be reduced in number or eliminated when discerning fluorescent molecules based on lifetime. In some cases, a single pulsed optical source operating at a single characteristic wavelength may be used to excite different fluorescent molecules that emit within a same wavelength region of the optical spectrum but have measurably different lifetimes. An analytic system that uses a single pulsed optical source, rather than multiple sources operating at different wavelengths, to excite and discern different fluorescent molecules emitting in a same wavelength region can be less complex to operate and maintain, more compact, and may be manufactured at lower cost.

Although analytic systems based on fluorescent lifetime analysis may have certain benefits, the amount of information obtained by an analytic system and/or detection accuracy may be increased by allowing for additional detection techniques. For example, some analytic systems 5-160 may additionally be configured to discern one or more properties of a sample based on fluorescent wavelength and/or fluorescent intensity.

Referring again to FIG. 5-4, according to some embodiments, different fluorescent lifetimes may be distinguished with a photodetector that is configured to time-bin fluorescent emission events following excitation of a fluorescent molecule. The time binning may occur during a single charge-accumulation cycle for the photodetector. A charge-accumulation cycle is an interval between read-out events during which photo-generated carriers are accumulated in bins of the time-binning photodetector. The concept of determining fluorescent lifetime by time-binning of emission events is introduced graphically in FIG. 5-5. At time $t_e$ just prior to $t_1$, a fluorescent molecule or ensemble of fluorescent molecules of a same type (e.g., the type corresponding to curve B of FIG. 5-4) is (are) excited by a short or ultrashort optical pulse. For a large ensemble of molecules, the intensity of emission may have a time profile similar to curve B, as depicted in FIG. 5-5.

For a single molecule or a small number of molecules, however, the emission of fluorescent photons occurs according to the statistics of curve B in FIG. 5-4, for this example. A time-binning photodetector 5-322 may accumulate carriers generated from emission events into discrete time bins (three indicated in FIG. 5-5) that are temporally resolved with respect to the excitation time of the fluorescent molecule(s). When a large number of emission events are summed, carriers accumulated in the time bins may approximate the decaying intensity curve shown in FIG. 5-5, and the binned signals can be used to distinguish between different fluorescent molecules or different environments in which a fluorescent molecule is located.

Figures 2, 3, 4, 5, 6:
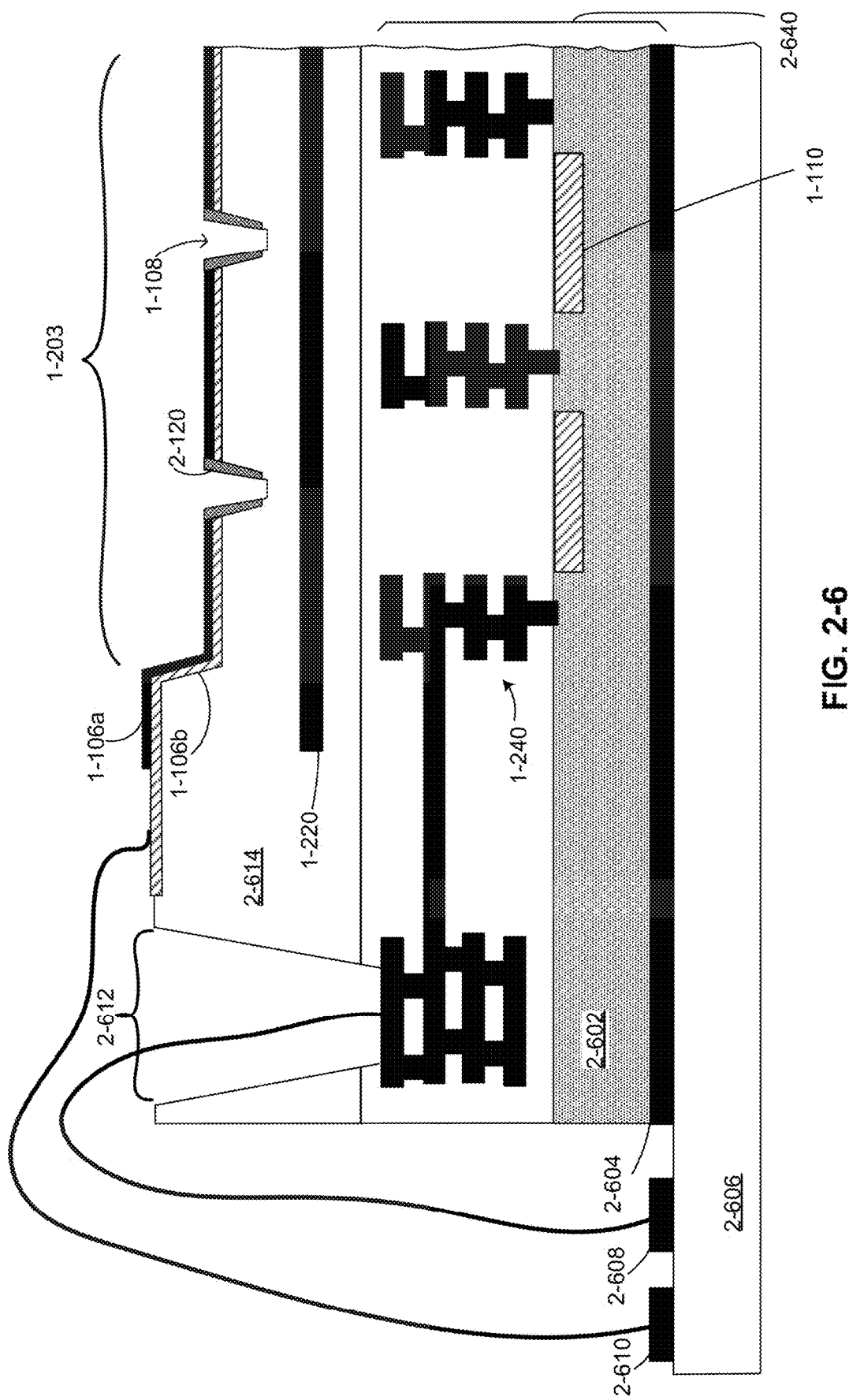
Figures 2, 3, 4, 5, 6, 7:
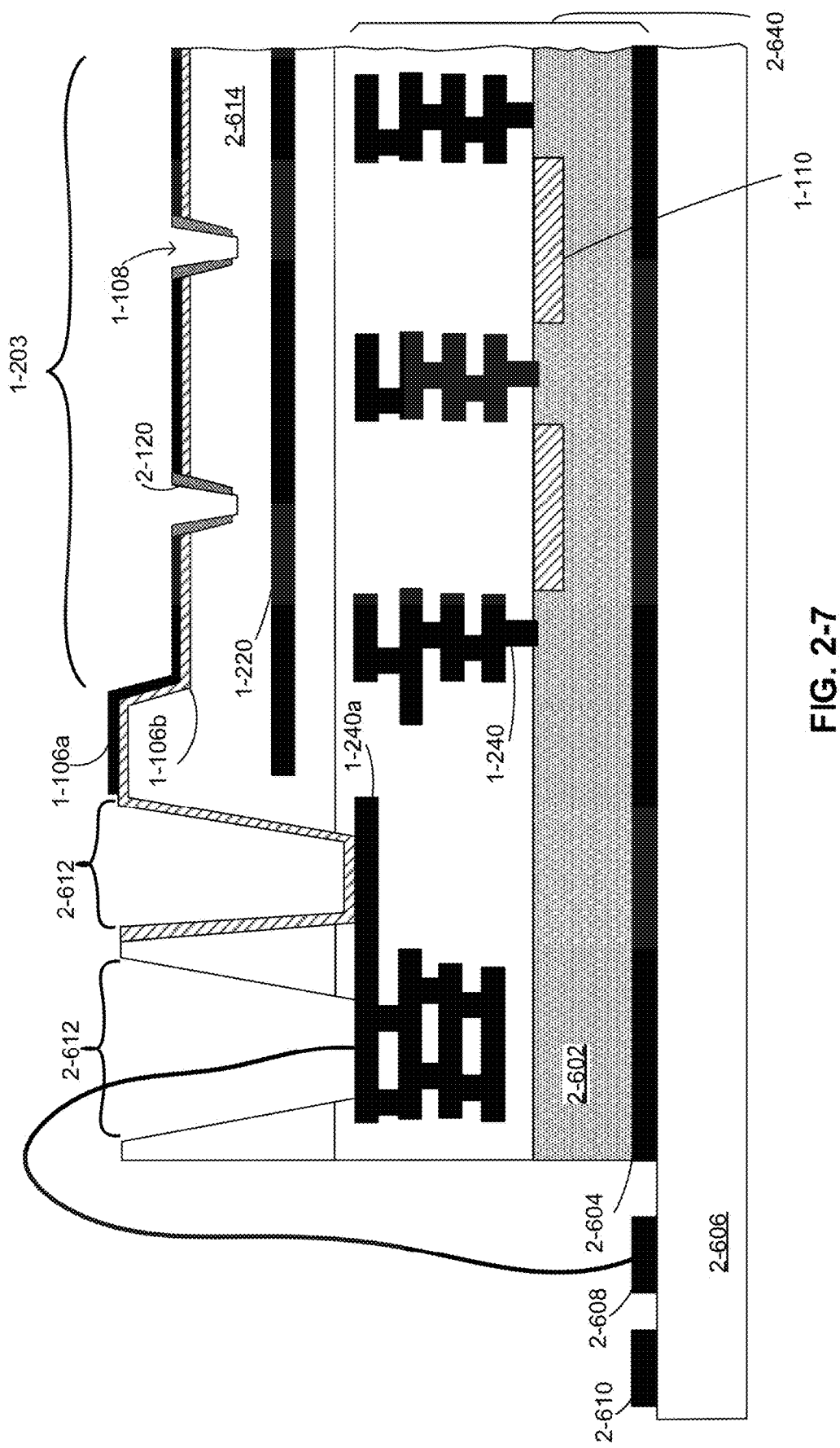
Figures 2, 3, 4, 5, 6, 7, 8:
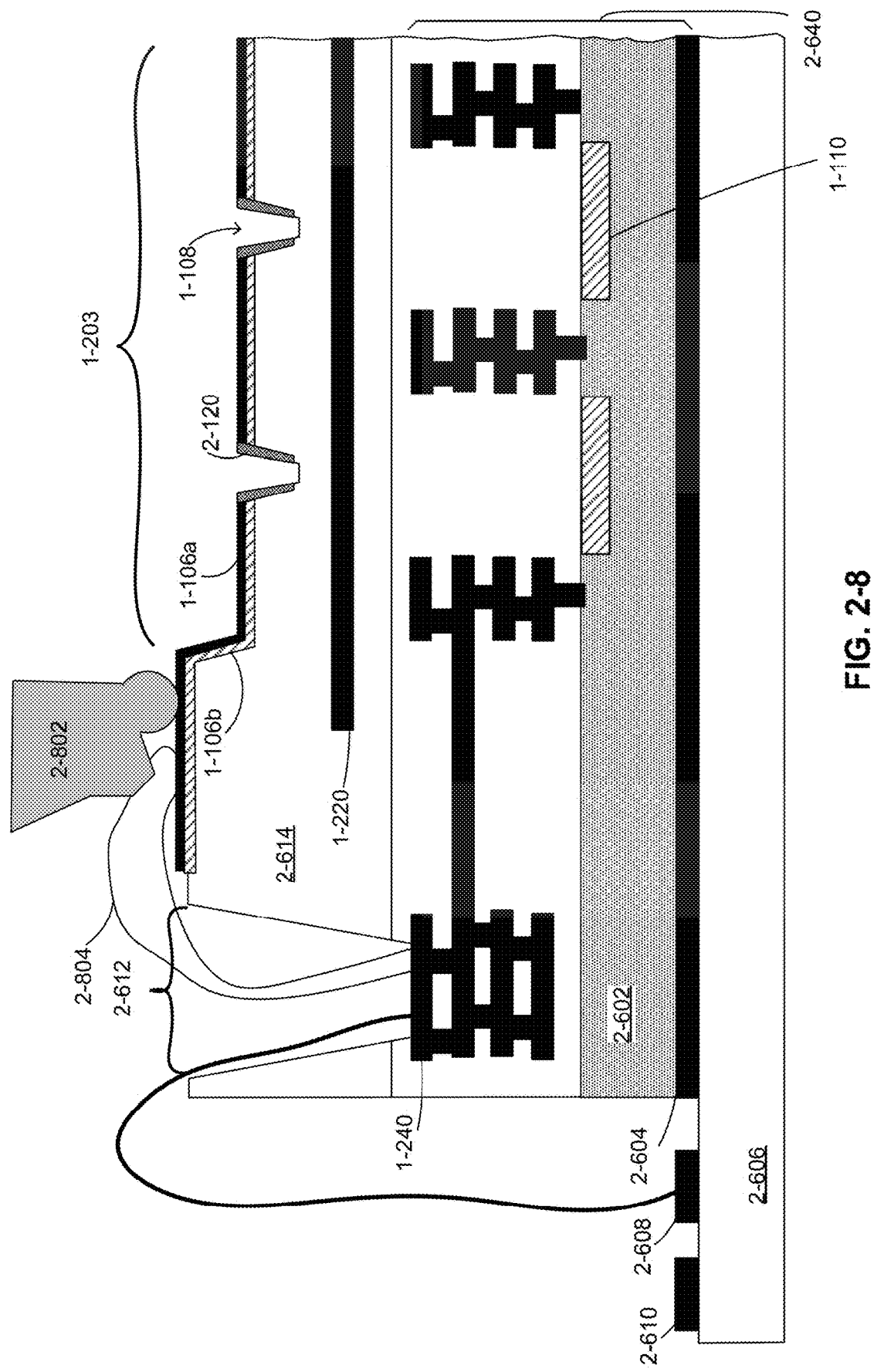
Figures 2, 3, 4, 5, 6, 7, 8, 9:
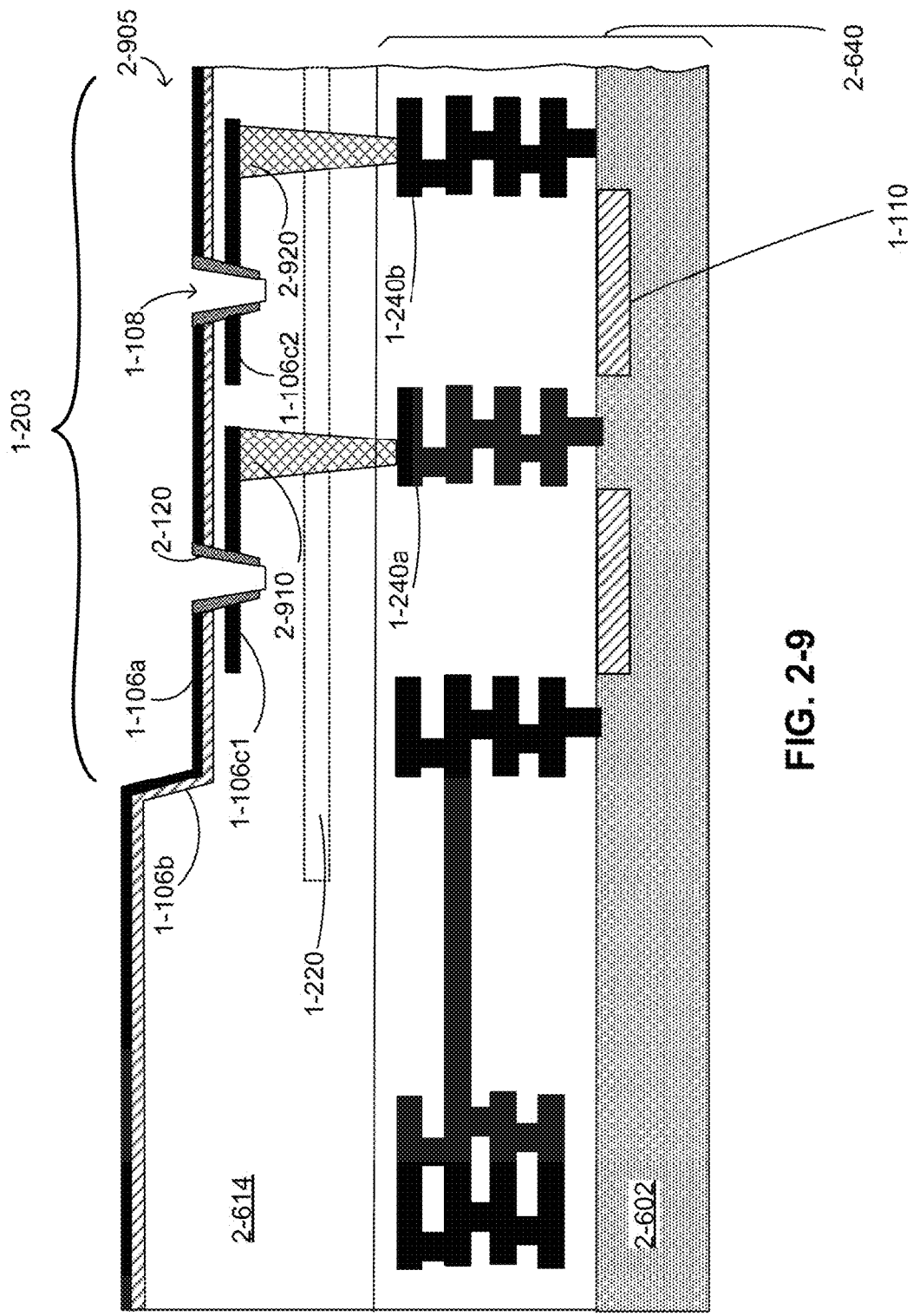
Figures 1A, 5:
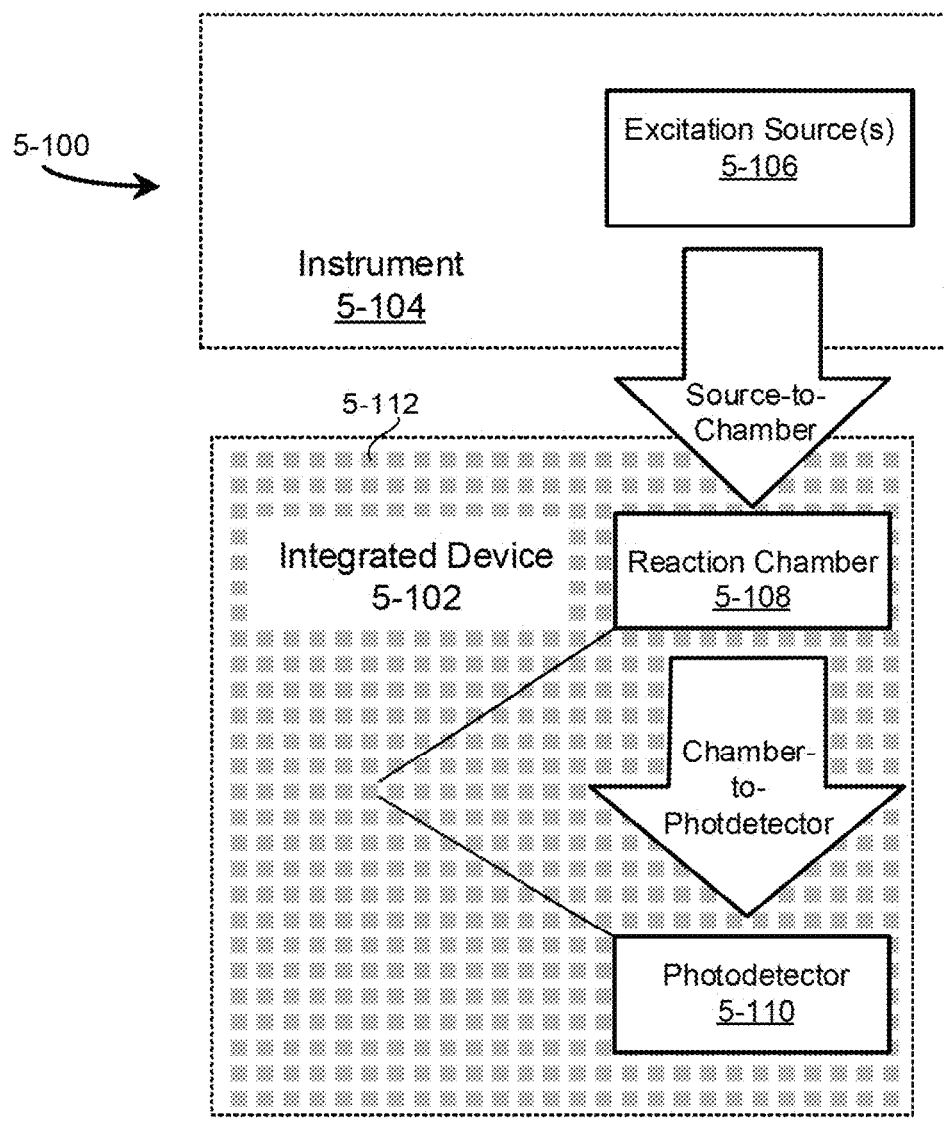
Figures 1B, 5:
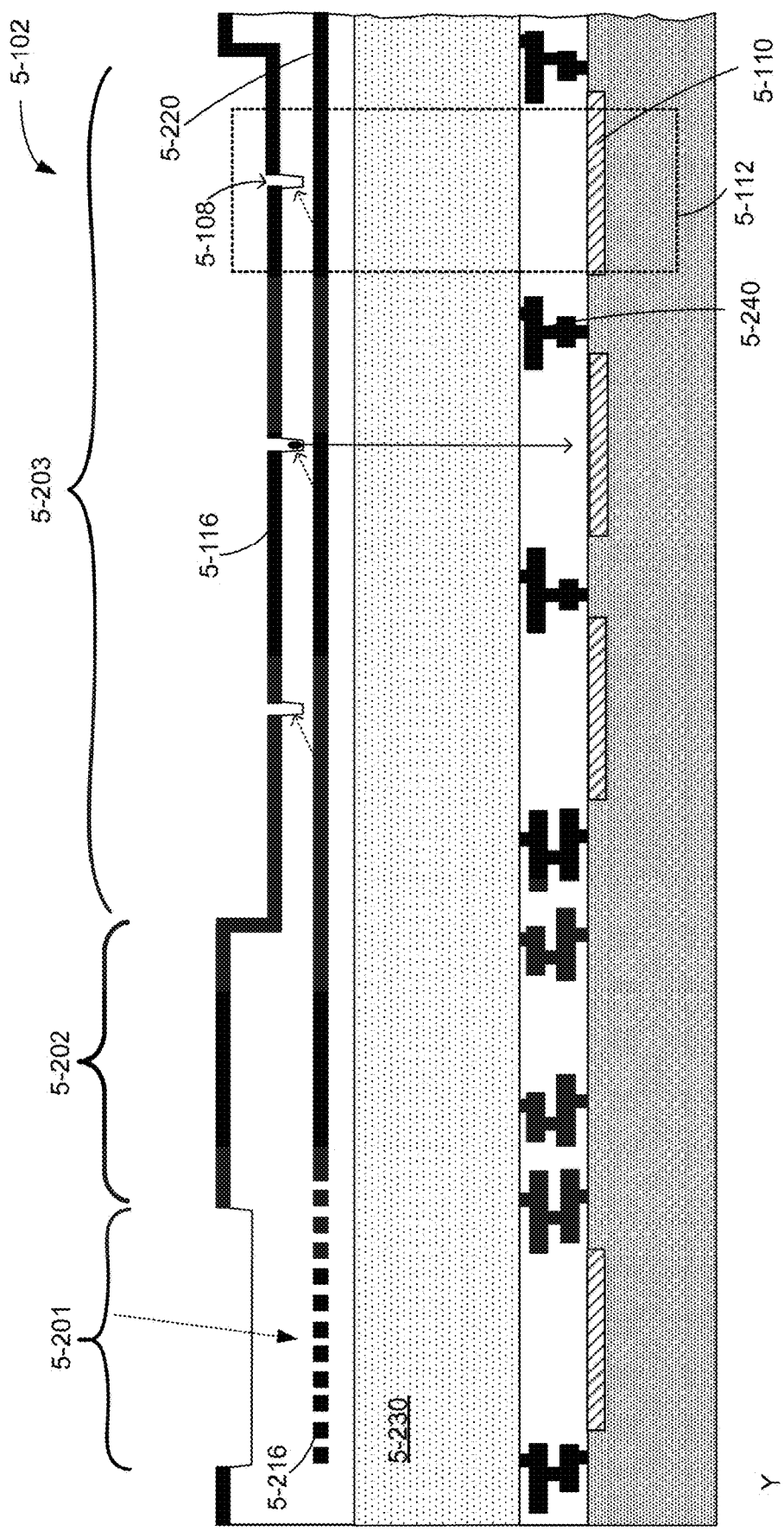
Figures 2, 5:
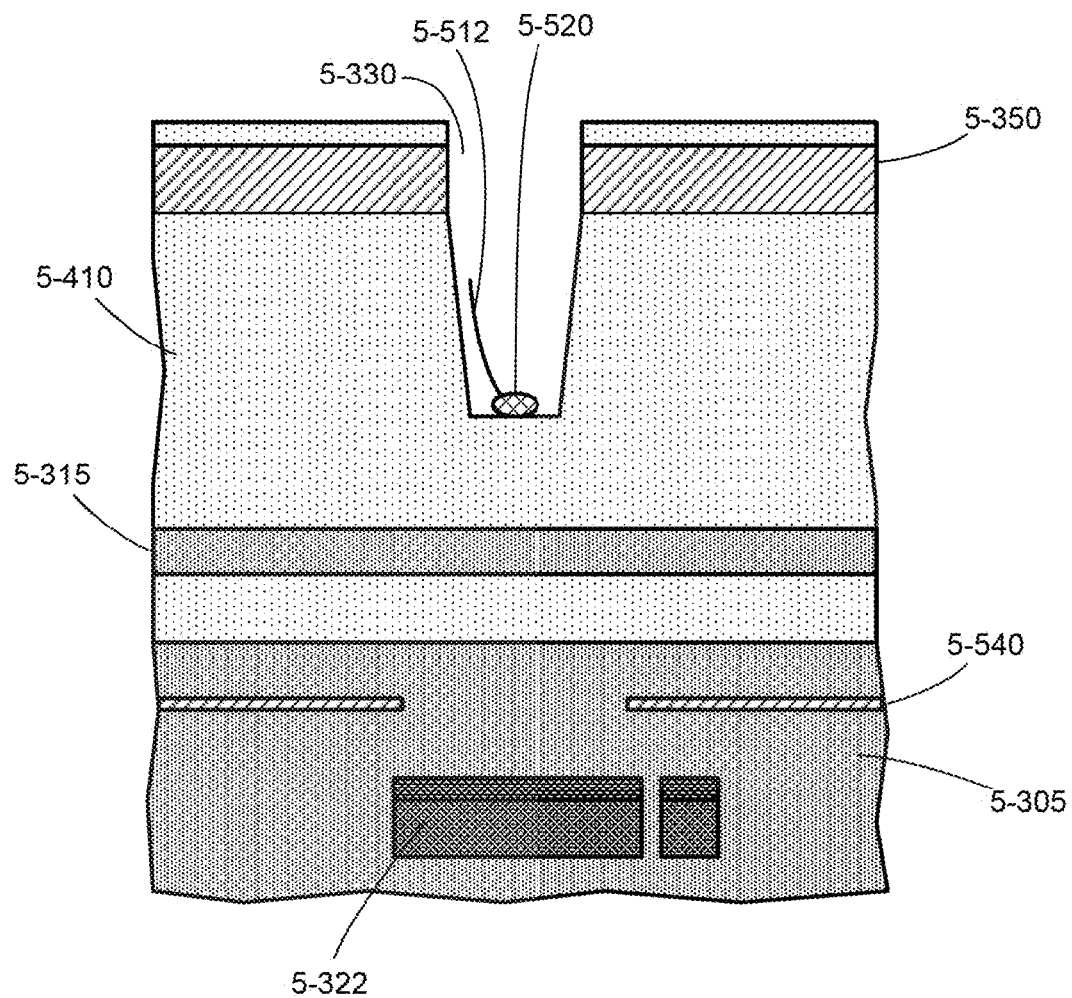
Figures 3, 5:
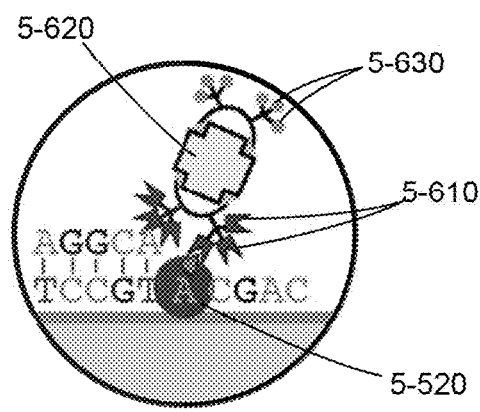
Figures 4, 5:
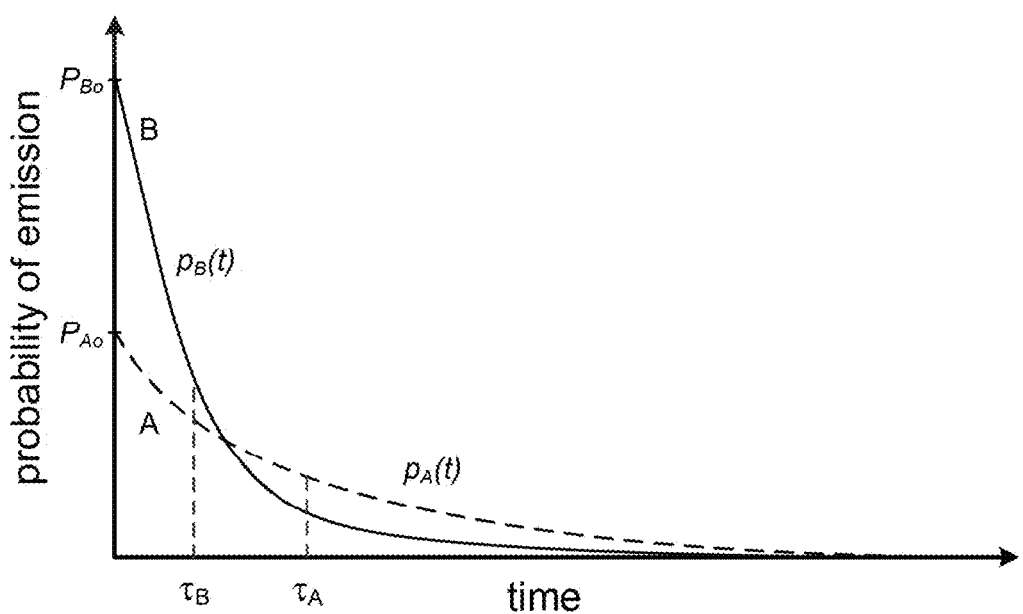
Figure 5:
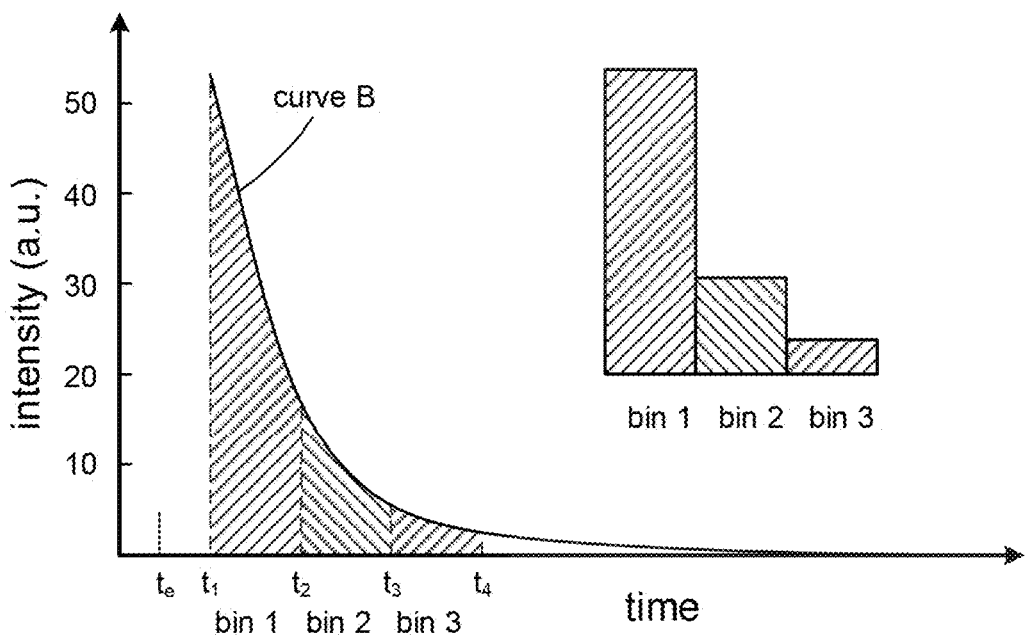
Figures 5, 6, 6A:
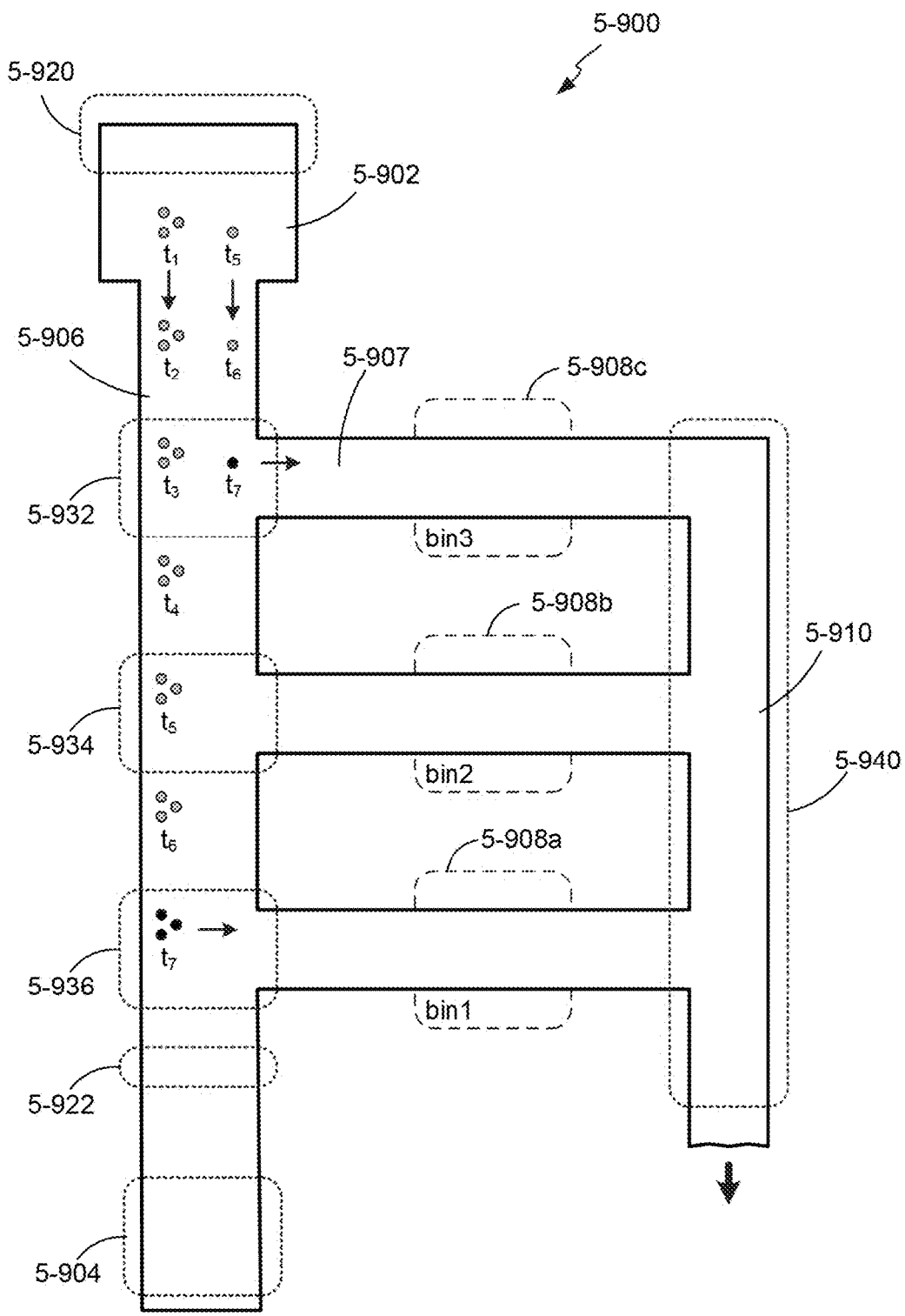

Examples of a time-binning photodetector are described in U.S. patent application Ser. No. 14/821,656, filed Aug. 7, 2015, titled "INTEGRATED DEVICE FOR TEMPORAL BINNING OF RECEIVED PHOTONS," which is incorporated herein by reference. For explanation purposes, a non-limiting embodiment of a time-binning photodetector is depicted in FIG. 5-6A. A single time-binning photodetector 5-900 may comprise a photon-absorption/carrier-generation region 5-902, a carrier travel/capture region 5-906, and carrier storage region having one or more charge carrier storage regions 5-908a, 5-908b, 5-908c, which may correspond to time bins. The carrier travel/capture region may be connected to the charge carrier storage regions by carrier-transport channels 5-907. Only three carrier-storage bins are shown, but there may be more or less. In some embodiments, a single time-binning photodetector 5-900 includes at least two charge carrier storage regions. There may be a read-out channel 5-910 connected to the charge carrier storage regions. The photon-absorption/carrier-generation region 5-902, carrier travel/capture region 5-906, charge carrier storage regions 5-908a, 5-908b, 5-908c, and read-out channel 5-910 may be formed by doping the semiconductor locally and/or forming adjacent insulating regions to provide photodetection capability and confine carriers. A time-binning photodetector 5-900 may include a drain 5-904 formed to connect with carrier travel/capture region 5-906. Drain 5-904 may be configured to discard charge carriers at particular times. By removing photogenerated charge carriers in this manner, unwanted charge carriers produced in response to excitation light may be discarded. A time-binning photodetector 5-900 may include a plurality of electrodes 5-920, 5-922, 5-932, 5-934, 5-936, 5-940 formed on the substrate that are configured to generate electric fields in the device for transporting charge carriers through the photodetector. The plurality of electrodes may establish a potential gradient such that charge carriers travel toward drain 5-904.

In operation, fluorescent photons may be received at the photon-absorption/carrier-generation region 5-902 at different times and generate carriers. For example, at approximately time $t_1$ three fluorescent photons may generate three carrier electrons in a depletion region of the photon-absorption/carrier-generation region 5-902. An electric field in the device (due to doping and/or an externally applied bias to electrodes 5-920 and 5-922, and optionally or alternatively to 5-932, 5-934, 5-936) may move the carriers to the carrier travel/capture region 5-906. In the carrier travel/capture region, distance of travel translates to a time after excitation of the fluorescent molecules. At a later time $t_5$, another fluorescent photon may be received in the photon-absorption/carrier-generation region 5-902 and generate an additional carrier. At this time, the first three carriers have traveled to a position in the carrier travel/capture region 5-906 adjacent to the second storage bin 5-908b. At a later time $t_7$, an electrical bias may be applied between electrodes 5-932, 5-934, 5-936 and electrode 5-940 to laterally transport carriers from the carrier travel/capture region 5-906 to the storage bins. The first three carriers may then be transported to and retained in the first bin 5-908a and the later-generated carrier may be transported to and retained in the third bin 5-908c. In some implementations, the time intervals corresponding to each storage bin are at the sub-nanosecond time scale, though longer time scales may be used in some embodiments (e.g., in embodiments where fluorophores have longer decay times).

The process of generating and time-binning charge carriers after an excitation event (e.g., excitation pulse from a pulsed optical source) may occur once after a single excitation pulse or be repeated multiple times after multiple excitation pulses during a single charge-accumulation cycle for the photodetector 5-900. After charge accumulation is complete, carriers may be read out of the storage bins via the read-out channel 5-910. For example, an appropriate biasing sequence may be applied to at least electrode 5-940 and a downstream electrode (not shown) to remove carriers from the storage bins 5-908a, 5-908b, 5-908c.

Time-binning photodetector 5-900 may be configured to discard charge carriers produced from photons of excitation light, or other unwanted light. The timing of the raising of one or more potential barriers within the carrier travel/capture region 5-906 may be timed such that photogenerated carriers produced by unwanted light, including excitation light, travels towards drain 5-904 and not towards charge carrier storage regions 5-908a, 5-908b, 5-908c. The timing of applying a voltage to an electrode, such as electrode 5-922, to raise a potential barrier may occur after a period of time such that some or all of the charge carriers generated during the period of time travel towards drain 5-904 and are not directed to charge carrier storage regions 5-908a, 5-908b, 5-908c. Subsequent charge carriers generated, after the period of time, may be selectively directed to charge carrier storage regions 5-908a, 5-908b, 5-908c. In some embodiments, the excitation light is a pulse of excitation light, and time-binning photodetector 5-900 may be configured to discard at least some of the charge carriers produced from photons of an excitation light pulse over a first period of time. After the first period of time, time-binning photodetector 5-900 may selectively direct, over a second period of time, one or more charge carriers produced by incident photons into respective charge carrier storage regions based upon times at which the charge carriers are produced.

After a number of excitation events, the accumulated signal in each electron-storage bin may be read out to provide a histogram having corresponding bins that represent the fluorescent emission decay rate, for example. Such a process is illustrated in FIG. 5-7A and FIG. 5-7B. The histogram's bins may indicate a number of photons detected during each time interval after excitation of the fluorophore(s) in a reaction chamber. In some embodiments, signals for the bins will be accumulated following a large number of excitation pulses, as depicted in FIG. 5-7A. The excitation pulses may occur at times $t_{e1}, t_{e2}, t_{e3}, \ldots t_{eN}$ which are separated by the pulse interval time T. There may be between $10^5$ and $10^7$ excitation pulses applied to the reaction chamber during an accumulation of signals in the electron-storage bins. In some embodiments, one bin (bin 0) may be configured to detect an amplitude of excitation light delivered with each optical pulse, and be used as a reference signal (e.g., to normalize data).

Figures 5, 6, 6B:
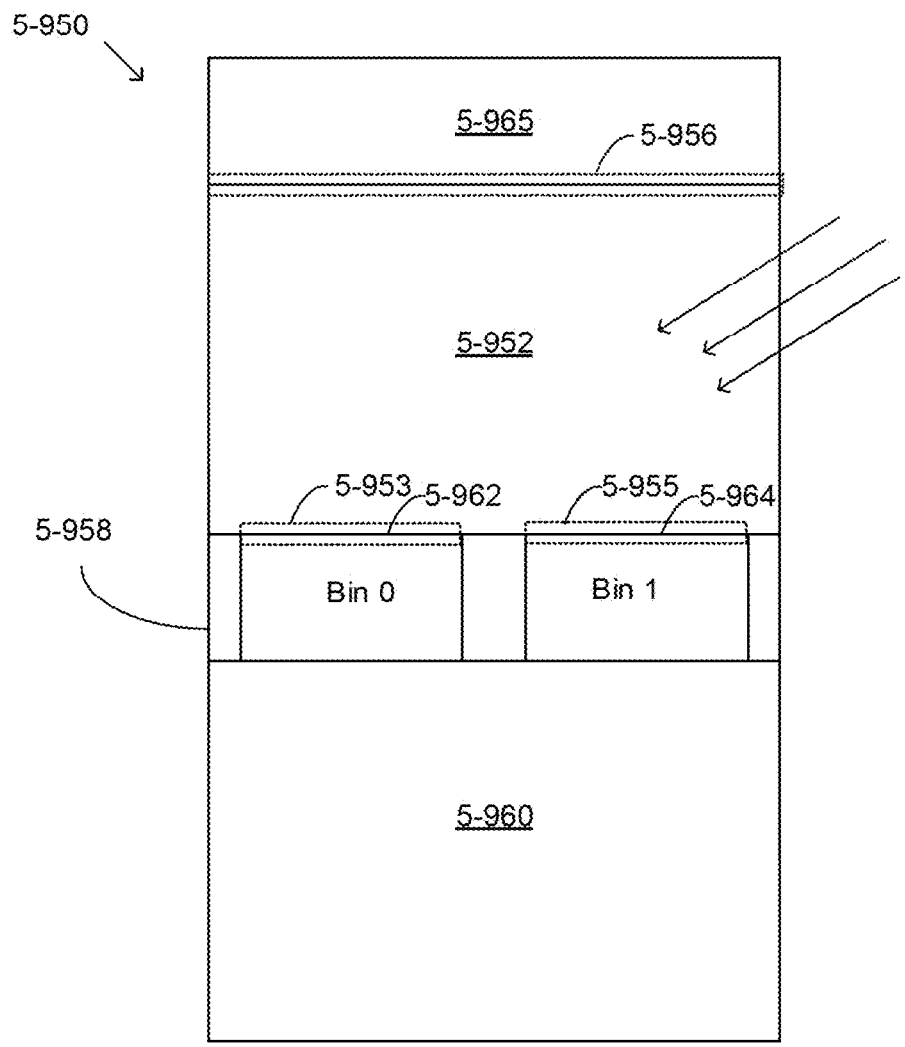
Figures 5, 6, 7, 7A:
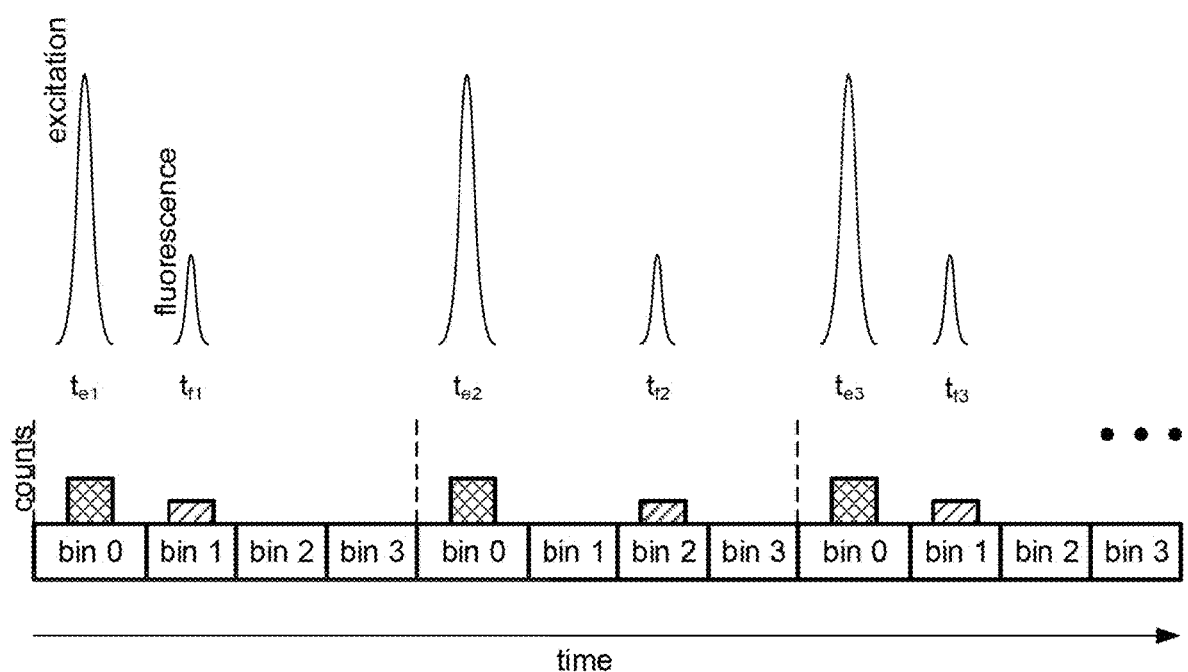
Figures 5, 6, 7, 7B:
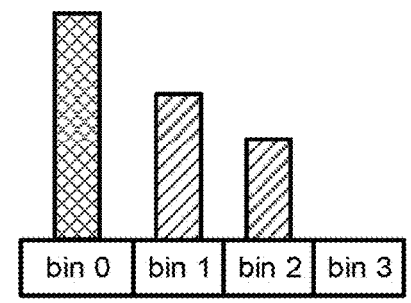
Figures 5, 6, 7, 8, 8A:
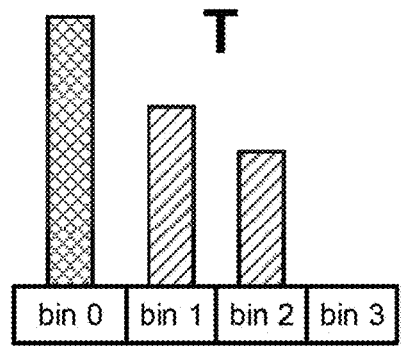
Figures 5, 6, 7, 8, 8B:
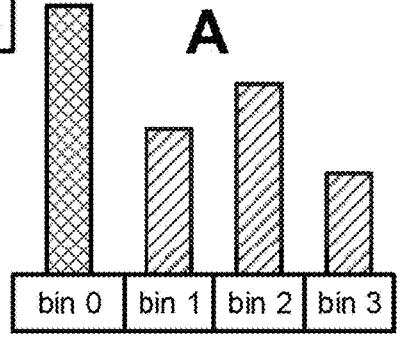
Figures 5, 6, 7, 8, 8C:
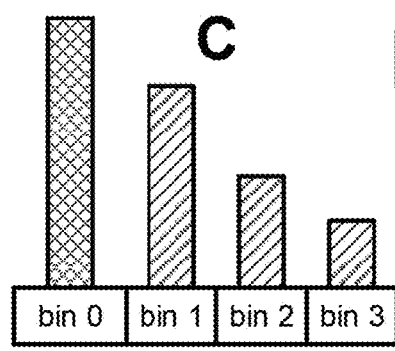
Figures 5, 6, 7, 8, 8D:
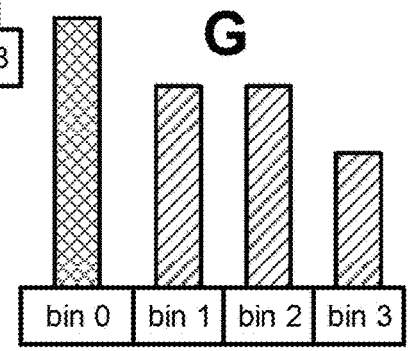

In some embodiments, a time-binning photodetector may generate charge carriers in a photon absorption/carrier generation region and directly transfer charge carriers to a charge carrier storage bin in a charge carrier storage region. In such embodiments, the time-binning photodetector may not include a carrier travel/capture region. Such a time-binning photodetector may be referred to as a "direct binning pixel." Examples of a time-binning photodetectors, including direct binning pixels, are described in U.S. patent application Ser. No. 15/852,571, filed Dec. 22, 2017, titled "INTEGRATED PHOTODETECTOR WITH DIRECT BINNING PIXEL," which is incorporated herein by reference. For explanation purposes, a non-limiting embodiment of a time-binning photodetector is depicted in FIG. 5-6B. As shown in FIG. 5-6B, time-binning photodetector 5-950 includes photon absorption/carrier generation region 5-952, bins of charge carrier storage region 5-958, and readout circuitry 5-960 that reads out signals from the bins of charge carrier storage region 5-958. The bin to which a charge carrier is transferred is based on the time of arrival of a photon in photon absorption/carrier generation region 5-952 that produces the charge carrier. FIG. 5-6B shows an example of time-binning photodetector having two bins in charge carrier storage region 5-958: bin 0 and bin 1. In some instances, bin 0 may aggregate charge carriers received in one period following a trigger event (e.g., a pulse of excitation light), and bin 1 may aggregate charge carriers received in a later time period with respect to a trigger event. However, charge storage region 5-958 may have any number of bins, such as one bin, three bins, four bins, or more. Time-binning photodetector 5-950 may include electrodes 5-953, 5-955, and 5-956, which may be configured to apply voltages to establish potential gradients to direct charge carriers. Time-binning photodetector 5-950 may include rejection region 5-965, which may act as a drain or otherwise be configured to discard charge carriers produced in photon absorption/carrier generation region 5-952. A period of time when charge carriers are rejected by rejection region 5-965 may be timed to occur during a trigger event, such as an excitation light pulse.

Since an excitation light pulse may produce a number of unwanted charge carriers in photon absorption/carrier generation region 5-952, a potential gradient may be established in pixel 5-950 to drain such charge carriers to rejection region 5-965 during a rejection period. As an example, rejection region 5-965 may include a high potential diffusion area where electrons are drained to a supply voltage. Rejection region 5-965 may include an electrode 5-956 that charge couples region 5-952 directly to rejection region 5-965. The voltage of the electrode 5-956 may be varied to establish a desired potential gradient in photon absorption/carrier generation region 5-952. During a rejection period, the voltage of the electrode 5-956 may be set to a level that draws carriers from the photon absorption/carrier generation region 5-952 into the electrode 5-956, and out to the supply voltage. For example, the voltage of the electrode 5-956 may be set to a positive voltage to attract electrons, such that they are drawn away from the photon absorption/carrier generation region 5-952 to rejection region 5-965. Rejection region 5-965 may be considered a "lateral rejection region" because it allows transferring carriers laterally from region 5-952 to a drain.

Following the rejection period, a photogenerated charge carrier produced in photon absorption/carrier generation region 5-952 may be time-binned. Individual charge carriers may be directed to a bin based on their time of arrival. To do so, the electrical potential between photon absorption/carrier generation region 5-952 and charge carrier storage region 5-958 may be changed in respective time periods to establish a potential gradient that causes the photogenerated charge carriers to be directed to respective time bins. For example, during a first time period a barrier 5-962 formed by electrode 5-953 may be lowered, and a potential gradient may be established from photon absorption/carrier generation region 5-952 to bin 0, such that a carrier generated during this period is transferred to bin 0. Then, during a second time period, a barrier 5-964 formed by electrode 5-955 may be lowered, and a potential gradient may be established from photon absorption/carrier generation region 5-952 to bin 1, such that a carrier generated during this later period is transferred to bin 1.

In some implementations, only a single photon on average may be emitted from a fluorophore following an excitation event, as depicted in FIG. 5-7A. After a first excitation event at time $t_{e1}$, the emitted photon at time $t_{f1}$ may occur within a first time interval, so that the resulting electron signal is accumulated in the first electron-storage bin (contributes to bin 1). In a subsequent excitation event at time $t_{e2}$, the emitted photon at time $t_{f2}$ may occur within a second time interval, so that the resulting electron signal contributes to bin 2.

After a large number of excitation events and signal accumulations, the electron-storage bins of the time-binning photodetector 5-322 may be read out to provide a multi-valued signal (e.g., a histogram of two or more values, an N-dimensional vector, etc.) for a reaction chamber. The signal values for each bin may depend upon the decay rate of the fluorophore. For example and referring again to FIG. 5-4, a fluorophore having a decay curve B will have a higher ratio of signal in bin 1 to bin 2 than a fluorophore having a decay curve A. The values from the bins may be analyzed and compared against calibration values, and/or each other, to determine the particular fluorophore, which in turn identifies the nucleotide or nucleotide analog (or any other molecule or sample of interest) linked to the fluorophore when in the reaction chamber.

To further aid in understanding the signal analysis, the accumulated, multi-bin values may be plotted as a histogram, as depicted in FIG. 5-7B for example, or may be recorded as a vector or location in N-dimensional space. Calibration runs may be performed separately to acquire calibration values for the multi-valued signals (e.g., calibration histograms) for four different fluorophores linked to the four nucleotides or nucleotide analogs. As an example, the calibration histograms may appear as depicted in FIG. 5-8A (fluorescent label associated with the T nucleotide), FIG. 5-8B (fluorescent label associated with the A nucleotide), FIG. 5-8C (fluorescent label associated with the C nucleotide), and FIG. 5-8D (fluorescent label associated with the G nucleotide). A comparison of the measured multi-valued signal (corresponding to the histogram of FIG. 5-7B) to the calibration multi-valued signals may determine the identity "T" (FIG. 5-8A) of the nucleotide or nucleotide analog being incorporated into the growing strand of DNA.

In some implementations, fluorescent intensity may be used additionally or alternatively to distinguish between different fluorophores. For example, some fluorophores may emit at significantly different intensities or have a significant difference in their probabilities of excitation (e.g., at least a difference of about 35%) even though their decay rates may be similar. By referencing binned signals (bins 1-3) to measured excitation light bin 0, it may be possible to distinguish different fluorophores based on intensity levels.

In some embodiments, different numbers of fluorophores of the same type may be linked to different nucleotides or nucleotide analogs, so that the nucleotides may be identified based on fluorophore intensity. For example, two fluorophores may be linked to a first nucleotide (e.g., "C") or nucleotide analog and four or more fluorophores may be linked to a second nucleotide (e.g., "T") or nucleotide analog. Because of the different numbers of fluorophores, there may be different excitation and fluorophore emission probabilities associated with the different nucleotides. For example, there may be more emission events for the "T" nucleotide or nucleotide analog during a signal accumulation interval, so that the apparent intensity of the bins is significantly higher than for the "C" nucleotide or nucleotide analog.

The inventors have recognized and appreciated that distinguishing nucleotides or any other biological or chemical samples based on fluorophore decay rates and/or fluorophore intensities enables a simplification of the optical excitation and detection systems in an instrument 5-104. For example, optical excitation may be performed with a single-wavelength source (e.g., a source producing one characteristic wavelength rather than multiple sources or a source operating at multiple different characteristic wavelengths). Additionally, wavelength discriminating optics and filters may not be needed in the detection system. Also, a single photodetector may be used for each reaction chamber to detect emission from different fluorophores.

The phrase "characteristic wavelength" or "wavelength" is used to refer to a central or predominant wavelength within a limited bandwidth of radiation (e.g., a central or peak wavelength within a 20 nm bandwidth output by a pulsed optical source). In some cases, "characteristic wavelength" or "wavelength" may be used to refer to a peak wavelength within a total bandwidth of radiation output by a source.

The inventors have recognized and appreciated that fluorophores having emission wavelengths in a range between about 560 nm and about 900 nm can provide adequate amounts of fluorescence to be detected by a time-binning photodetector (which may be fabricated on a silicon wafer using CMOS processes). These fluorophores can be linked to biological molecules of interest such as nucleotides or nucleotide analogs. Fluorescent emission in this wavelength range may be detected with higher responsivity in a silicon-based photodetector than fluorescence at longer wavelengths. Additionally, fluorophores and associated linkers in this wavelength range may not interfere with incorporation of the nucleotides or nucleotide analogs into growing strands of DNA. The inventors have also recognized and appreciated that fluorophores having emission wavelengths in a range between about 560 nm and about 660 nm may be optically excited with a single-wavelength source. An example fluorophore in this range is Alexa Fluor 647, available from Thermo Fisher Scientific Inc. of Waltham, Mass. The inventors have also recognized and appreciated that excitation light at shorter wavelengths (e.g., between about 500 nm and about 650 nm) may be required to excite fluorophores that emit at wavelengths between about 560 nm and about 900 nm. In some embodiments, the time-binning photodetectors may efficiently detect longer-wavelength emission from the samples or associated components in the reaction chamber, e.g., by incorporating other materials, such as Ge, into the photodetectors active region.

In some embodiments, a sample may be labeled with one or more markers, and emission associated with the markers is discernable by the instrument. For example, the photodetector may be configured to convert photons from the emission light into electrons to form an electrical signal that may be used to discern a lifetime that is dependent on the emission light from a specific marker. By using markers with different lifetimes to label samples, specific samples may be identified based on the resulting electrical signal detected by the photodetector.

A suspension may contain multiple types of molecules and different luminescent markers may uniquely associate with a molecule type. During or after excitation, the luminescent marker may emit emission light. One or more properties of the emission light may be used to identify one or more types of molecules in the suspension. Properties of the emission light used to distinguish among types of molecules may include a fluorescence lifetime value, intensity, and/or emission wavelength. A photodetector may detect photons, including photons of emission light, and provide electrical signals indicative of one or more of these properties. In some embodiments, electrical signals from a photodetector may provide information about a distribution of photon arrival times across one or more time intervals. The distribution of photon arrival times may correspond to when a photon is detected after a pulse of excitation light is emitted by an excitation source. A value for a time interval may correspond to a number of photons detected during the time interval. Relative values across multiple time intervals may provide an indication of a temporal characteristic of the emission light (e.g., lifetime). Analyzing a sample may include distinguishing among markers by comparing values for two or more different time intervals within a distribution. In some embodiments, an indication of the intensity may be provided by determining a number of photons across all time bins in a distribution.

The described embodiments can be implemented in various configurations. Example configurations include configurations (1)-(32) and methods (33)-(53) below.

(1) An integrated device comprising a reaction chamber formed through a surface of the integrated device; and at least one electrically conductive layer forming at least one electrode arranged adjacent to the reaction chamber, wherein the at least one electrode, when biased, produces at least one electric field that assists loading a sample into the reaction chamber.

(2) The integrated device of configuration (1), wherein a maximum dimension of the reaction chamber is less than one micron.

(3) The integrated device of configuration (1) or (2), wherein the at least one electrode is arranged to produce an electric field that has an increased intensity in a first region within 500 nm of an opening to the reaction chamber compared to a second region outside the first region.

(4) The integrated device of any one of configurations (1)-(3), wherein the electric field assists loading a sample from a suspension placed in contact with the surface over the reaction chamber.

(5) The integrated device of any one of configurations (1)-(4), wherein the reaction chamber is configured to hold only one sample for analysis of the sample.

(6) The integrated device of any one of configurations (1)-(5), wherein a bottom of the reaction chamber terminates within one micron from an optical waveguide.

(7) The integrated device of any one of configurations (1)-(6), wherein a first electrically conductive layer of the at least one electrically conductive layer is patterned to form two electrodes adjacent to the reaction chamber, wherein the two electrodes, when biased, produce an electric field that is mainly oriented laterally.

(8) The integrated device of any one of configurations (1)-(7), further comprising: a semiconductor region in a substrate below the reaction chamber; a photodetector formed in the semiconductor region; and a conductive interconnect connected to the photodetector, wherein the conductive interconnect is a first electrically conductive layer of the at least one electrically conductive layer.

(9) The integrated device of any one of configurations (1)-(8), wherein the surface comprises a surface of a first electrically conductive layer of the at least one electrically conductive layer.

(10) The integrated device of any one of configurations (1)-(9), wherein the reaction chamber extends through one or more electrically conductive layers of the at least one electrically conductive layer.

(11) The integrated device of any one of configurations (1)-(10), further comprising electrically conductive material formed on a sidewall of the reaction chamber and electrically coupled to a first electrically conductive layer of the at least one electrically conductive layer.

(12) The integrated device of any one of configurations (1)-(11), further comprising: a dielectric layer formed between a first electrically conductive layer and a second electrically conductive layer of the at least one electrically conductive layer; and an opening in the dielectric layer that overlaps with the reaction chamber, wherein a dimension of the opening in the dielectric layer is smaller than a dimension of an opening of the reaction chamber at the surface.

(13) The integrated device of any one of configurations (1)-(12), wherein the at least one electrically conductive layer includes a first layer comprising aluminum and/or titanium in contact with a second layer comprising titanium nitride.

(14) The integrated device of any one of configurations (1)-(13), wherein a distance between a bottom surface of the reaction chamber and a first electrically conductive layer of the at least one electrically conductive layer is less than 400 nm.

(15) The integrated device of any one of configurations (1)-(14), wherein the at least one electrically conductive layer comprises: a first electrically conductive layer located at the surface of the integrated device; and a second electrically conductive layer located below the surface and separated from the first electrically conductive layer by dielectric material, wherein the reaction chamber extends through the first electrically conductive layer and the second electrically conductive layer.

(16) The integrated device of configuration (15), wherein the second electrically conductive layer extends no more than three microns in a lateral direction from the reaction chamber, excluding any conductive interconnect connected to the second electrically conductive layer.

(17) The integrated device of any one of configurations (1)-(16), further comprising a conductive via formed vertically and adjacent to the reaction chamber, wherein the conductive via connects a first electrically conductive layer of the at least one electrically conductive layer to conductive interconnect below the reaction chamber.

(18) The integrated device of any one of configurations (1)-(17), wherein the reaction chamber is one of a plurality of reaction chambers arranged on the surface of the integrated device and having a same structure as the reaction chamber and wherein the at least one electrically conductive layer further forms at least one electrode arranged adjacent to each reaction chamber of the plurality of reaction chambers.

(19) The integrated device of configuration (18), further comprising bias circuitry formed on the integrated device and arranged to provide a same bias to a first electrode at each reaction chamber of the plurality of reaction chambers.

(20) The integrated device of configuration (18), further comprising bias circuitry formed on the integrated device and arranged to provide a bias to a first electrode formed from a first electrically conductive layer of the at least one electrically conductive layer at each reaction chamber in a first group of reaction chambers independently of a first electrode formed from the first electrically conductive layer at each reaction chamber in a second group of reaction chambers.

(21) The integrated device of configuration (18), further comprising bias circuitry formed on the integrated device and arranged to provide a bias to a first electrode formed from a first electrically conductive layer of the at least one electrically conductive layer at a reaction chamber of the plurality of reaction chambers independently of a first electrode formed from the electrically conductive layer at any other reaction chamber of the plurality of reaction chambers.

(22) The integrated device of any one of configurations (1)-(21), further comprising bias circuitry formed on the integrated device and arranged to provide a first bias to a first electrode of the at least one electrode and a second electrode to produce a first electric field and a second electric field different from the first electric field that assist in loading the sample into the reaction chamber.

(23) The integrated device of any one of configurations (1)-(22), further comprising a sample reservoir having a fluid seal with the surface and configured to retain a suspension comprising a plurality of the samples.

(24) The integrated device of configuration (23), further comprising an external electrode configured to contact the suspension in the sample reservoir.

(25) An apparatus for analyzing samples, the apparatus comprising an integrated device having: a reaction chamber formed through a surface of the integrated device; and at least one electrically conductive layer forming at least one electrode arranged adjacent to the reaction chamber, wherein the at least one electrode, when biased, produces at least one electric field that assists loading a sample into the reaction chamber.

(26) The apparatus of configuration (25), wherein a maximum dimension of the reaction chamber is less than one micron and the reaction chamber is configured to hold one sample for analysis of the sample.

(27) The apparatus of configuration (25) or (26), further comprising bias circuitry configured to produce at least one bias and apply the at least one bias to the at least one electrically conductive layer.

(28) The apparatus of configuration (27), wherein a first bias of the at least one bias comprises a periodic waveform.

(29) The apparatus of configuration (27), wherein a first bias of the at least one bias comprises a combination of two periodic waveforms.

(30) The apparatus of any one of configurations (27)-(29), further comprising: a photodetector located adjacent to the reaction chamber; and feedback circuitry arranged to change the first bias in response to the photodetector detecting that the sample has been loaded in the reaction chamber.

(31) The apparatus of any one of configurations (27)-(30), further comprising: a sample reservoir having a fluid seal with the surface and configured to retain a suspension comprising a plurality of the samples; and an external electrode configured to contact the suspension in the sample reservoir, wherein the bias circuitry is further configured to apply a second bias of the at least one bias to the external electrode.

(32) The apparatus of configuration (31), wherein the bias circuitry is further configured to apply the first bias during a first time interval and to apply the second bias during a second time interval that is different from the first time interval.

At least some of the above configurations (1) through (32) may be used in practicing the following method embodiments.

(33) A method for loading a sample of interest in an integrated device, the method comprising: receiving a suspension that includes the sample of interest onto a surface of the integrated device, wherein the suspension covers a reaction chamber formed into the surface; applying an electrical signal between a first electrode and a second electrode; and generating an electric field that operates to assist loading, into the reaction chamber, the sample of interest.

(34) The method of (33), wherein generating the electric field comprises generating the electric field that has an increased intensity in a first region within 500 nm of an opening to the reaction chamber compared to a second region outside the first region.

(35) The method of (33) or (34), wherein the first electrode is located adjacent to the reaction chamber and the reaction chamber has a maximum dimension of less than one micron.

(36) The method of (33) or (34), wherein the first electrode is external to the integrated device and the reaction chamber has a maximum dimension of less than one micron.

(37) The method of any one of (33) through (36), wherein the electric field acts on the sample of interest differently from other components in the suspension.

(38) The method of any one of (33) through (37), wherein applying the electrical signal comprises: applying a first electrical signal to move the sample of interest towards the surface of the integrated device from the suspension; and applying a second electrical signal to move the sample of interest within the reaction chamber.

(39) The method of any one of (33) through (38), wherein applying the electrical signal comprises applying an electrical signal that is a combination of two periodic waveforms.

(40) The method of any one of (33) through (39), further comprising applying an additional electrical signal to the first electrode that reduces or impedes loading, into the reaction chamber, a second sample of interest.

(41) The method of any one of (33) through (40), further comprising applying an additional electrical signal to the first electrode that moves a portion of the sample of interest out of the reaction chamber.

(42) The method of any one of (33) through (41), further comprising applying a second electrical signal between a third electrode and the first electrode that is different from the electrical signal applied between the first electrode and second electrode.

(43) The method of any one of (33) through (42), further comprising introducing into the suspension a crowding agent configured to increase the concentration of the sample of interest proximate to the surface of the integrated device.

(44) The method of (43), wherein the crowding agent is a polysaccharide.

(45) The method of (44), wherein the polysaccharide is a cellulose compound selected from the group consisting of methyl cellulose, ethyl cellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, and carboxymethyl cellulose.

(46) The method of any one of (33) through (45), further comprising introducing into the suspension a condensing agent configured to reduce the pervaded volume of the sample of interest in the suspension.

(47) The method of (46), wherein the condensing agent comprises a polycation that is polycationic in the suspension, and the polycation is selected from spermine, spermidine, polylysine, polyarginine, polyhistidine, polyornithine, putrescine, and protamine.

(48) The method of any one of (33) through (47), wherein the sample of interest comprises a nucleic acid molecule.

(49) The method of (48), wherein the nucleic acid molecule is between about 1 kb to about 10 kb, between about 10 kb to about 25 kb, between about 25 kb to about 50 kb, between about 50 kb to about 100 kb, between about 100 kb to about 250 kb, between about 250 kb to about 500 kb, or between about 500 kb to about 1000 kb.

(50) A method of forming an integrated device comprising: forming at least one electrically conductive layer over a region of dielectric material, wherein the dielectric material includes at least one waveguide; forming a reaction chamber through the at least one electrically conductive layer; and forming at least one electrode configured to generate, when biased, an electric field that operates to assist loading a sample of interest into the reaction chamber.

(51) The method of (50), wherein the reaction chamber has a maximum dimension less than one micron.

(52) The method of (50) or (51), wherein forming at least one electrically conductive layer comprises forming a conductive layer over a semiconductor region that that is part of an integrated circuit in the semiconductor region.

(53) The method of (52), further comprising forming a photodetector arranged to detect emission light from the reaction chamber, wherein the photodetector is part of the integrated circuit in the semiconductor region.

IV. Conclusion

Having thus described several aspects and embodiments of the technology of this application, it is to be appreciated that various alterations, modifications, and improvements will readily occur to those of ordinary skill in the art. Such alterations, modifications, and improvements are intended to be within the spirit and scope of the technology described in the application. It is, therefore, to be understood that the foregoing embodiments are presented by way of example only and that, within the scope of the appended claims and equivalents thereto, inventive embodiments may be practiced otherwise than as specifically described. In addition, any combination of two or more features, systems, articles, materials, kits, and/or methods described herein, if such features, systems, articles, materials, kits, and/or methods are not mutually inconsistent, is included within the scope of the present disclosure.

Also, as described, some aspects may be embodied as one or more methods. The acts performed as part of the method may be ordered in any suitable way. Accordingly, embodiments may be constructed in which acts are performed in an order different than illustrated, which may include performing some acts simultaneously, even though shown as sequential acts in illustrative embodiments.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified.

In the claims, as well as in the specification above, all transitional phrases such as "comprising," "including," "carrying," "having," "containing," "involving," "holding," "composed of," and the like are to be understood to be open-ended, i.e., to mean including but not limited to. The transitional phrases "consisting of" and "consisting essentially of" shall be closed or semi-closed transitional phrases, respectively.

What is claimed is:

1. A method for loading a sample of interest in an integrated device, the method comprising:
   receiving a suspension that includes the sample of interest onto a surface of the integrated device, wherein the suspension covers a reaction chamber formed into the surface;
   applying an electrical signal between a first electrode and a second electrode; and
   generating an electric field that operates to assist loading, into the reaction chamber, the sample of interest.

2. The method of claim 1, wherein generating the electric field comprises generating the electric field that has an increased intensity in a first region within 500 nm of an opening to the reaction chamber compared to a second region outside the first region.

3. The method of claim 1, wherein the first electrode is located adjacent to the reaction chamber and the reaction chamber has a maximum dimension of less than one micron.

4. The method of claim 1, wherein the first electrode is external to the integrated device and the reaction chamber has a maximum dimension of less than one micron.

5. The method of claim 1, wherein the electric field acts on the sample of interest differently from other components in the suspension.

6. The method of claim 1, wherein applying the electrical signal comprises:
applying a first electrical signal to move the sample of interest towards the surface of the integrated device from the suspension; and
applying a second electrical signal to move the sample of interest within the reaction chamber.

7. The method of claim 1, wherein applying the electrical signal comprises applying an electrical signal that is a combination of two periodic waveforms.

8. The method of claim 1, further comprising applying an additional electrical signal to the first electrode that reduces or impedes loading, into the reaction chamber, a second sample of interest.

9. The method of claim 1, further comprising applying an additional electrical signal to the first electrode that moves a portion of the sample of interest out of the reaction chamber.

10. The method of claim 1, further comprising applying a second electrical signal between a third electrode and the first electrode that is different from the electrical signal applied between the first electrode and second electrode.

11. The method of claim 1, further comprising introducing into the suspension a crowding agent configured to increase the concentration of the sample of interest proximate to the surface of the integrated device.

12. The method of claim 11, wherein the crowding agent is a polysaccharide.

13. The method of claim 12, wherein the polysaccharide is a cellulose compound selected from the group consisting of methyl cellulose, ethyl cellulose, ethyl methyl cellulose, hydroxyethyl cellulose, hydroxypropyl cellulose, hydroxyethyl methyl cellulose, hydroxypropyl methyl cellulose, ethyl hydroxyethyl cellulose, and carboxymethyl cellulose.

14. The method of claim 1, further comprising introducing into the suspension a condensing agent configured to reduce the pervaded volume of the sample of interest in the suspension.

15. The method of claim 14, wherein the condensing agent comprises a polycation that is polycationic in the suspension, and the polycation is selected from spermine, spermidine, polylysine, polyarginine, polyhistidine, polyornithine, putrescine, and protamine.

16. The method of claim 1, wherein the sample of interest comprises a nucleic acid molecule.

17. The method of claim 16, wherein the nucleic acid molecule is between about 1 kb to about 10 kb, between about 10 kb to about 25 kb, between about 25 kb to about 50 kb, between about 50 kb to about 100 kb, between about 100 kb to about 250 kb, between about 250 kb to about 500 kb, or between about 500 kb to about 1000 kb.

* * * * *